(12) United States Patent
Chrivia et al.

(10) Patent No.: US 6,365,372 B1
(45) Date of Patent: Apr. 2, 2002

(54) SNF2 RELATED CBP ACTIVATOR PROTEIN (SRCAP)

(75) Inventors: John Chrivia, Kirkwood; Peter Yaciuk, Webster Groves, both of MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 09/579,181

(22) Filed: May 25, 2000

Related U.S. Application Data

(60) Provisional application No. 60/136,620, filed on May 27, 1999.

(51) Int. Cl.⁷ .......................... C12P 21/06; C12N 15/00; C07H 21/02; C07K 1/00; C07K 16/00
(52) U.S. Cl. ................. 435/69.1; 435/320; 536/23.1; 530/350; 530/389
(58) Field of Search ..................... 536/23.1; 435/69.1, 435/320; 530/350, 389

(56) References Cited

PUBLICATIONS

Identification of a Novel SNF2/SW12 Protein Family Member, SRCAP, Which Interacts with CREB–binding Protein by Holly Johnston et al., Journal of Biological Chemistry, vol. 274, No. 23, Jun. 4, 1999, pp. 16370–16376.

Characterization of Human Activating Transcription Factor 4, a Transcriptional Activator That Interacts with Multiple Domains of cAMP–responsive Element–binding Protein (CREB)–binding Protein (CBP) by Liang and Hai, The Journal of Biological Chemistry, vol. 272, No. 38, Sep. 19, 1997, pp. 24088–24095.

NCBI Nucleotide—GenBank—Human mRNA for KIAA0309.

*Primary Examiner*—Hankyel T. Park
(74) *Attorney, Agent, or Firm*—Thompson Coburn LLP

(57) ABSTRACT

A protein, SRCAP, is provided. The protein is capable of co-activating CREB binding protein (CBP) mediated transcription, as well as activating transcription without CBP. SRCAP is a Snf2 family member. As such, it has ATPase activity. Fragments of SRCAP are also provided, as are polynucleotides encoding SRCAP and its fragments. Antibodies that bind to SRCAP are also provided. These compositions are useful for enhancing transcription in cells and patients. The compositions are also useful for reducing transcription in cells and patients.

30 Claims, 21 Drawing Sheets

|  | BOX I |  | BOX Ia |  | BOX II |  |
|---|---|---|---|---|---|---|
| SRCAP | GILADEMGLGKT | 453 | LIIVPTSVMLNW | 485 | WRYLILDEAQNIKN | 555 |
| P113 | GILADDMGLGKT | 301 | LIICPLSVLSNW | 484 | WLRVILDEGHAIRN | 588 |
| Hip116 | GILADDMGLGKT | 301 | LVICPLSVLSNW | 490 | WLRVILDEGHAIRN | 564 |
| Snf2 | GILADEMGLGKT | 799 | LIIVPLSTLSNW | 813 | WVHMIIDEGHRMKN | 901 |
| Iswi | GILADEMGLGKT | 160 | IVIVPKSTLQNW | 192 | WRYLVLDEAHRIKN | 263 |
| Chd1 | CILADEMGLGKT | 511 | LLVVPLSTLTSW | 543 | WAFIGVDEAHRLKN | 619 |
| Rad16 | GVLADEMGMGKT | 217 | LVVAPTVALMQW | 245 | FYRVILDEAHNIKD | 329 |
| Mot1 | GILCDDMGLGKT | 1304 | LIICPLSLTGHW | 1347 | YNYCVLDEGHIIKN | 1415 |
| Hsnf2a | GILADEMGLGKT | 752 | LIIVPLSTLSNW | 784 | WKYMILDEGHRMKN | 854 |

|  | BOX III |  | BOX IV |  |
|---|---|---|---|---|
| SRCAP | RLLLTGTPLQNSLMEIWSLMHFL | 594 | FLLRRVKVDVEK | 650 |
| P113 | RWVLTGTPIQNSLKDIWSLLSFL | 593 | ITLRRITKTSKIK | 645 |
| Hip116 | RWVLTGTPIQNSLKDIWSLLSFL | 603 | ITLRRITKTSKIK | 651 |
| Snf2 | RLLITGTPLQNNLPEIWALLNFV | 941 | FLLRRLKKDVEK | 1001 |
| Iswi | RLLITGTPLQNNLHEIWALLNFL | 302 | FLLRRLKAEVEK | 350 |
| Chd1 | RLLITGTPLQNSLKELWSLLHFI | 658 | FLLRRVKKDVEK | 702 |
| Rad16 | RWCLSGTPLQNRIGEMYSLIRFL | 368 | IMLRRITKVERAD | 452 |
| Mot1 | RLLITGTPIQNNVLEIWSLFDPL | 1454 | FMLRRLKEDVLS | 1514 |
| Hsnf2a | RLLLTGTPLQNNLKELWALLNFL | 894 | FLLRRLKKEVES | 952 |

FIGURE 2B(i.)

|  | BOX V | BOX VI | |
|---|---|---|---|
| SRCAP | FILSTRSGGVGLNLTGADTVVFYDSDWNPTMDAQAQDRCHRIGQTRDVHIYRL | | 1907 |
| P113 | STV.LKAGGVGLNLCARSRVFLMDPAWNPAAEDQCFDRCHRLGQKQEVIITKF | | 953 |
| Hip116 | MLLSLKAGGVGLNLSAASRVFLMDPAWNPAAEDQCFDRCHRLGQKQEVIITKF | | 960 |
| Snf2 | FILSTRAGGLGLNLATADTVIIFDTDWNPHQDLQAQDRAHRIGQNEVRILRL | | 1211 |
| Iswi | FMLSTRAGGLGINLATADVVIIYDSDWNPQMDLQAMDRAHRIGQKKQVRVFRL | | 555 |
| Chd1 | FLLSTRAGGLGINLASADTVVIFDSDWNPQMDLQAQARAHRIGQKKQVNIYRL | | 910 |
| Rad16 | FLVSLKAGGVALNLCEASQVFILDPWWNPSVEWQSGDRVHRIGQYRPVKITRF | | 744 |
| Mot1 | LLLTKVGGLGLNLTGADTVIFVEHDWNPMNDLQAMDRAHRIGQKKVVNIYRI | | 1756 |
| Hsnf2a | FLLSTRAGGLGLNLQAADTVVIFDSDWNPHQDLQAQDRAHRIGQQNEVRVLRL | | 1170 |

FIGURE 2B(ii.)

SNF2 RELATED CBP ACTIVATOR PROTEIN (SRCAP)

This application claims the benefit of U.S. Provisional Application No. 60/136,620, filed May 27, 1999, incorporated in its entirety herein by reference.

This invention was made with Government support under National Institutes of Health Grant No. DK52231. The Government has certain rights in the invention.

BACKGROUND OF THE INVENTION

(1) Field of the Invention

The present invention generally relates to regulation of transcription factors. More specifically, the invention relates to a novel SNF2/SWI2 protein family member, SRCAP, that is capable of activating transcription directly as well as interacting with CREB binding protein (CBP) to enhance the ability of CBP to activate transcription.

(2) Description of the Related Art

Transcription factors are well known as proteins that bind to regulatory regions of genes and other proteins to modulate transcription of the genes. Examples of transcription factors relevant to this invention include CREB, c-jun, c-myb, MyoD, E2F1, YY1, TBP, TFIIB, and RNAP II. The action of these transcription factors is affected by co-activators, notably CREB binding protein (CBP).

CBP is a histone acetyltransferase capable of acetylating not only histones but also several transcription factors such as GATA-1 and p53 (Boyes et al., 1998, Nature 396, 594–598; Hung et al., 1999, Cell Biol. 19, 3496–3505; Webster et al., 1999, Mol. Cell. Biol. 19, 3485–3495). CBP also binds to several proteins that also finction as histone acetyltransferases (P/CAF, p/CIP and the p160 co-activators such as SRC-1).

Precisely how CBP interacts with these co-activators and other cellular factors to activate transcription has not been completely elucidated. The notion that CBP interacts with a specific subset of factors at different promoters was first suggested by the work of Korzus et al., 1998, Science 279, 703–707. These authors showed that CBP in conjunction with P/CIP, SRC-1 and P/CAF was required for activation of transcription of a RARE reporter gene by the retinoic acid receptor, whereas only CBP, P/CAF and p/CIP were needed for activation of a CRE reporter gene by CREB and only CBP and P/CAF are required for transcription of a GAS-reporter gene by STAT-1. In addition the HAT activity of each of these co-activators was not needed at each promoter. For example, with the RARE- reporter gene, despite the fact that the pCIP-P/CAF-SRC-1-CBP complex was needed for activation of transcription, only the HAT activity of P/CAF was needed, whereas transcription of the CRE-reporter by the CBP-P/CAF-pCIP complex required the HAT activity of CBP not p/CAF. Thus, the specific transcription factors which CBP binds determine not only the requirement for specific co-activators but whether their HAT activity is also needed. The requirement for a specific HAT function may also be altered depending on what signaling pathways activate transcription. Xu et al. (1998, Nature 395, 301–306) have reported that forskolin activation of Pitl mediated transcription requires the HAT finction of CBP whereas insulin activation of Pitl mediated transcription does not.

Why different HAT activities are needed is unclear but CBP, P/CAF and p/CIP have been shown to have different substrate specificities (Perissi et al., 1999, Proc. Natl. Acad. Sci. U.S.A. 96, 3652–3657) suggesting they acetylate a different subset of proteins. The possibility that substrate specificity of these proteins may be regulated is illustrated by the work of Perissi et al. (Id.) who reported that binding of p/CIP to CBP changes the substrate specificity of CBP. Repression of the HAT activity of CBP by the adenoviral 12S E1A protein has been reported by several laboratories and occurs through E1A contacts with the HAT domain of CBP (Charkravati et al., 1999, Cell 96, 393–403, reviewed in Goldman et al., 1997, Recent Prob. Horm. Res. 52, 103–120). In contrast to these findings, recent work by Ait-Si Ali et al. (1998, Nature 396, 184–186) indicates that in some circumstances E1A can stimulate the HAT activity of CBP.

The activity of several kinases has been shown to regulate CBP function. The NGF stimulated kinase, $p42/44^{MAPK}$, activates CBP mediated transcription by a phosphorylation event which is blocked by the MAPK inhibitor PD 98059. p42/44 MAPK directly associates with CBP and can phosphorylate CBP in vitro (Liu et al., 1999, Neuroreport 10, 1239–1243). Studies have also demonstrated the cyclin E-cyclin dependent kinase 2 (cdk2) complex binds CBP and mediates hyperphosphorylation of CBP at the G1/S boundary (Ait-Si Ali et al., supra). Inhibition of cyclin E-Cdk2 by the cyclin dependent kinase inhibitor p21, results in the activation of NF-kB mediated transcription (Perlins et al., 1997, Science 275, 523–527). The binding of the kinase $pp90^{RSK}$ to CBP has different effects depending on the signaling pathway. $pp90^{RSK}$-CBP interaction is needed for insulin stimulated transcription, and blocks the ability of CBP to function as a co-activator for cAMP-mediated transcription. The activity of $pp90^{RSK}$ can be mimicked by a kinase defective mutant, indicating association of $pp90^{RSK}$ with CBP is enough to alter its finction (Nakajima et al., 1996, Cell 86,465–474). Other studies have also demonstrated that protein kinase A and CAM kinase II and IV positively modulate the ability of specific domains within CBP to activate transcription. However, the precise mechanism by which this occurs has not been delineated (Swope et al., 1996, J. Biol. Chem 271, 28138–28145, Liu et al., 1998, J. Biol. Chem. 273, 25541–25544).

CBP interacts with several general transcription factors. Swope et al. (Id.) demonstrated that TBP binds in vitro to the N-terminal end of CBP and Abrahams et al. (1993, Oncogene 8, 1639–1647) and Dallis et al. (1997, J. Virol. 71, 1726–1731) have shown that TBP binds CBP in vivo. TFIIB binds to the C-terminal end of CBP and this binding is blocked by the adenoviral protein E1A (Felzien et al., 1999, Mol. Cell. Biol. 19,4261–4266). Deletion of the TBP binding domain from CBP prevents it from acting as a co-activator for CREB whereas deletion of the TFIIB binding site has no effect (Swope et al., Id.). CBP also binds RNA helicase A and this association appears to be required for the interaction of CBP with RNA polymerase II Nakajima et al., 1997, Cell 90, 1107–1112).

Phosphorylation of CREB in the KID domain enhances its ability to activate transcription and is mediated by a number of kinases (CAM kinase H and IV and protein kinase A) in response to biological stimuli such as neuronal signals or increased levels of intracellular cAMP (Gonzalez et al., 1991, Mol. Cell. Biol. 11, 1306–1312; Fiol et al., 1994, J. Biol. Chem. 269, 32187–32193; Sun et al., 1994, Genes Develop 8, 2527–2539). Specific iphosphorylation of serine 133 within CREB promotes association with CBP but studies by Sun and Maurer (1995, J. Biol. Chem. 270, 7041–7044) indicate this phosphorylation is not sufficient for activation of transcription. Other studies have found that phosphorylation of CREB on serines 129 and 142 modulate the ability of CREB to activate transcription (Fiol et al., supra; Sun and Maurer, supra) suggesting they change the way in which CREB and CBP interact perhaps alters the function of CBP (e.g. the HAT activity or binding of other proteins). The ability of CREB to activate transcription is also blocked by the MAPK inhibitor PD 98059 (Seternes et al., 1999, *Mol. Endocrinol.* 13, 1071–1083). Although the mechanism by which this occurs has not been completely elucidated other studies indicate that PD 98059 completely inhibits the ability of CBP to activate transcription (Liu et al., 1998, *J. Biol. Chem.* 273, 25541–25544).

Structure-finction studies by Swope et al. (1996, *J. Biol. Chem* 271, 28138–28145) indicated that deletion of amino acids 272–460 from the amino terminal end of CBP prevent it from acting as a co-activator for CREB. A $CBP_{227-460}$ peptide containing this deleted region also functions as a strong transcriptional activator when expressed as a Gal chimera (Gal-$CBP_{227-460}$). In addition, overexpression of a $CBP_{1-460}$ peptide squelches the ability of full length CBP to function as a CREB co-activator. Collectively, these studies suggest that a factor binding to the amino terminal end of CBP is essential for it to function as a co-activator for CREB. These studies also indicate that CBP contains several regions which are involved in the activation of transcription and which function as transcriptional activators when expressed as gal-CBP chimeras (Id.). Various binding studies have identified a number of co-activators, general transcription factors, kinases, and transcription factors that contact these regions of CBP. A partial list is shown in FIG. 1, where identification of the CBP domain that interacts with SRCAP is newly disclosed herein. See also Goldman et al., 1997, *Recent Progress in Hornone Research* 52, 103–1221.

A growing body of literature now illustrates the importance of CBP. The most compelling evidence for the importance of CBP has come from naturally occurring and artificially developed mutations. CBP appears to be critical in the development of the CNS, since a mutation in CBP has been associated with mental retardation in humans (Rubinstein-Taybi syndrome) (Petrij et al., 1995, *Nature* 376, 348–351). This hypothesis is strengthened by the finding that transgenic mice bearing similar CBP mutations have clinical features associated with Rubinstein-Taybi syndrome including: deficiency in long term memory, growth retardation, cardiac anomalies and skeletal abnormalities, and defects in hematopoiesis and vasculo-angiogenesis (Oike et al., 1999, *Blood* 93, 2771–2779; Oike et al., 1999, *Genetics* 8, 387–396). Mutations of CBP have also been found in a subset of patients with acute myeloid leukemia that have a t(8; 16)(p 11: p 13) chromosomal translocation which fuses CBP to the acetyltransferase MOZ (Burrow et al., 1996, *Nature Genetics* 383, 99–103).

The observation that mutations in CBP cause many distinct physiological defects is not surprising, since CBP serves as a co-activator for a wide variety of transcription factors. For example, CBP interacts with estrogen, progesterone, retinoic acid, vitamin D, glucocorticoid, and PPARγ receptors (reviewed in Mckenna et al., 1999, *Endocrine Reviews* 20, 321–344), which are important for sexual maturation, bone development, lipid metabolism and regulation of energy metabolism. CBP interacts with transcription factors that direct pancreatic islet morphogenesis (NeuroDI/BETA2, Sharma et al., 1999, *Mol. Cell. Biol.* 19, 704–713) and liver development (HNF4, Dell et al., 1999, *J. Biol. Chem.* 274, 9013–9021). CBP also serves as a co-activator for a number of transcription factors activated by growth factors such CREB, jun, fos, smad proteins and NF-kappaB, as well as a number of constitutively active transcription factors such as c-myb, NF-1 C, GATA-1 and p53 (Dai et al., 1996, *Genes and Develop.* 10, 524540; Chaudry et al., 1999, *J. Biol. Chem.* 274, 7072– 7081; Hung et al., 1999, *Cell Biol* 19, 3496–3505; Lambert et al., 1998, *J. Biol. Chem.* 273, 33048–33053).

Competition or "cross talk" between transcription factors for the limiting amount of CBP present in the cell has been reported to be a control mechanism for cellular response to different signaling pathways. For example, competition between NF-kappaB and the tumor suppressor p53 for CBP determines whether p53 mediated apoptosis occurs (Webster et al., 1999, *Mol. Cell. Biol.* 19, 3485–3495). Competition between GR and NF-kappaB has also been reported as a control mechanism for glucocorticoid mediated repression of NF-kappaB-mediated inflammation (Sheppard et al., 1998, *J. Biol. Chem.* 273, 29291–29294). In LNcAP cells, overexpression of the androgen receptor can block AP-1 mediated transcription (Fronsdal et al., 1999, *J. Biol. Chem.* 273, 31583–31859).

CBP is critical for the functioning of several viruses that impact human health. This includes human T cell lymphotrophic virus (HTLV-1), which recruits CBP to viral promoters through interaction of the viral protein TAX with CREB (Kwok et at., 1996). CBP also interacts directly with the viral transactivator protein Tat of human immunodeficiency virus type I (mHV-1) (Hottiger and Nabel, 1998, *J. Virol.* 72, 8252–8256). In humans, adenoviruses cause several diseases including: acute follicular conjunctivitis, pharyngoconjunctivial fever, epidermic keratoconjunctivitis, acute hemorrhagic cystitis, cervicitis, infantile diarrhea, and respiratory tract infections in children. Immune compromised individuals such as those who have undergone bone or organ transplant or who have AIDS are particularly susceptible to adenoviral caused diseases (reviewed in Chapter 65 of Zinsser, 1992, Microbiology, $20^{th}$ Ed., Joklik et al., Eds., Appleton and Lange). CBP interacts with several isoforms of the adenoviral protein EIA to mediate repression or activation of transcription (Felzien et al., 1999, *Mol. Cell. Biol.* 19,42616). CBP also functions as a co-activator for the zta protein of Epstein-Barr virus (Zerby et al., 1999, *Moll. Cell. Biol.* 19, 1617–1626). Epstein-Barr virus infections have been associated with fatal lymphoproliferation in immune deficient patients and the development of Burkitt's lymphoma (reviewed in Zinsser Microbiology, 1992, supra). CBP has also been indirectly implicated in the transcriptional regulation of other viruses through interaction with CREB. For example, CREB binds to the enhancer of the IE1/2 gene of human cytomegalovirus (Lang et al., 1992, *Nucl. Acids Res.* 20, 3287–3295), an important pathogen in immunosuppressed patients such as transplant recipients and AIDS patients (Drew, 1988, *J. Infect. Dis.* 158, 449456). CREB also binds the hepatitis B virus (HBV) enhancer element when complexed with the HBV protein, pX (Maguire et al., 1991, *Science* 252, 842–844). A possible role of CBP in some forms of cancer is suggested by the observation that CBP is part of a multi-subunit complex with the breast cancer tumor suppressor BRCA1 and RNA polymerase II (Neish et al., 1998, *Nucl. Acids Res.* 26, 847–853). In some forms of acute myeloid leukemia a t(7;11)(p15: p15) translocation results in the NUP98-HOXA9 fusion protein, which is a strong transcriptional activator that uses CBP as a co-activator (Kasper et al., 1999).

CREB and, therefore, CBP have been implicated as possible effectors of a number of physiological responses in the central nervous system. In rats, acute morphine treatment increases the level of activated CREB in the locus coeruleus. This effect is attenuated with chronic treatment. Acute morphine withdrawal increases the level of activated CREB. Thus, regulation of genes by CREB may contribute to changes leading to addiction (Guitart et al, 1992, *J. Neurochem.* 58, 1168–1171). Furthermore, the level of phosphorylated CREB increases in the suprachiamatic nuclei in response to light, suggesting it may be important for the entrainment of the pacemaker that controls hormonal and behavioral cycles (Ginty et al., 1993, *Science* 260, 238–241). In aplysia, the regimented application of serotonin to sensory neurons can be used to induce long-term memory. Analogs of cAMP are able to elicit some of the same responses suggesting CREB is involved. This hypothesis is supported by the finding that serotonin induces the phosphorylation of CREB (Kaang et al., 1993, *Neuron* 10, 427–435) and that microinjection of the oligonucleotides containing the binding site for CREB blocks serotonin induced long term memory (Dash et al., 1990, *Nature* 345, 718–721). Mice containing deletions in certain forms of CREB also appear to have defects in learning (Bourtchuladze et al., 1994, *Cell* 79, 59–68). Several lines of experiments also indicate CREB is involved in mediating the long-term effects of activity dependent plasticity at glutamatergic neurons (reviewed in Ghosh and Greenberg, 1995, *Science* 268, 239–247). A role of CBP is suggested by the recent studies by Hu et al. (1999, *Neuron* 22, 1–22), which indicate activation of glutamatergic neurons leads to an increase in the ability of CBP to activate transcription. This appears to be mediated by CaM kinases II and IV activated in response to increased calcium levels following depolarization and leads to phosphorylation of CBP (Hu et al., Id.).

Based on the importance of CBP in activating transcription, it would be desirable to identify other proteins that serve as transcriptional co-activators with CBP.

SUMMARY OF THE INVENTION

Accordingly, the inventors have succeeded in discovering a protein, called SRCAP, for Snf2 Related CBP Activator Protein, that is a transcriptional co-activator for CREB binding protein (CBP). SRCAP is unlike all other known CBP co-activators in that it also is a Snf2 family member, and, as such, has ATPase activity. SRCAP also is capable of activating transcription without CBP and is also capable of interacting with DEAD box helicases, adenoviral DBP protein, β-actin and nuclear receptors. SRCAP is also capable of DNA binding. Among the compositions also provided herein are fragments of SRCAP, polynucleotides encoding SRCAP or SRCAP fragments, complements of the SRCAP polynucleotides or fragments, and antibodies that specifically bind to SRCAP. These compositions are useful for, e.g., enhancing or suppressing CBP mediated transcriptional co-activation, and treatment of diseases involving inappropriate transcriptional activation that can be mediated by SRCAP or by CBP.

Thus, some embodiments of the present invention is directed to an isolated and purified SRCAP polypeptide. The polypeptide comprises the amino acid sequence of SEQ ID NO:2, or a conservatively substituted variant thereof, and wherein the polypeptide has ATPase activity and is capable of activating transcription. An example of a SRCAP polypeptide is provided as SEQ ID NO:2.

The present invention is also directed to an isolated and purified naturally occurring polypeptide comprising an amino acid sequence that has at least about 80% sequence homology to SEQ ID NO:2, wherein the polypeptide has ATPase activity and is capable of activating transcription. In preferred embodiments, the amino acid sequence that has at least about 90% sequence homology to SEQ ID NO:2.

In additional embodiments, the invention is directed to a polypeptide comprising at least 15 contiguous amino acids of any of the SRCAP polypeptides described above. In certain aspects, the polypeptide has at least one of the following SRCAP activities: ATPase, CREB binding protein (CBP) interaction and transcriptional co-activation, transcriptional activation without CBP, and DNA binding.

The present invention is also directed to a SRCAP chimera having a part of one of the above SRCAP polypeptides covalently attached to an amino acid sequence from a naturally occurring protein that is not a SRCAP. In preferred embodiments, the protein that is not SRCAP is a GAL4.

The present invention is further directed to a polynucleotide comprising a nucleic acid encoding any of the above-described SRCAP polypeptides. An example is SEQ ID NO:11. Complementary sequences to any of these polynucleotides are also provided, as are sequences that are capable of selectively hybridizing to the above sequences, as well as fragments of any of the polynucleotide sequences, where the fragment is at least 45 nucleotides long. These polynucleotides can be part of a vector used, e.g., to replicate the polynucleotide or express the encoded polypeptide. The vectors can also be used to create recombinant cells comprising any of the invention polynucleotides, and/or encoding any of the invention polypeptides.

The cells can be, e.g., an *E. coli* cell or any other appropriate cell, including a mammalian cell. The cell can also be part of a living animal, including a mammal.

The above polynucleotides can also be capable of hybridizing to a SRCAP mRNA and, as such, can serve as an antisense agent. Ribozymes capable of specifically cleaving any of the invention polynucleotides is also provided, as are polynucleotides encoding any of the previously described chimeras.

In additional embodiments, the present invention is also directed to antibodies that specifically bind to any of the above described polypeptides. In a preferred embodiment, the antibody binds to amino acids 2733–2971 of SEQ ID NO:11.

Additionally, the present invention is directed to a method of activating transcription in a cell. The method comprises treating the cell with any appropriate polypeptide, polynucleotide, or antibody of the invention. In preferred embodiments, the cell is in a mammal, which includes humans. In some aspects, the method further comprises implanting the cell into a mammal after treating the cell.

The present invention is also directed to methods of detecting a SRCAP in a sample. The methods comprise treating the sample with one of the above-described antibodies, then determining whether the antibody specifically binds to a component of the sample. In these methods, specific binding indicates the presence of SRCAP in the sample. The sample can be from a mammal, including humans. In preferred embodiments, the determining step is by ELISA, RIA, or methods that include an electrophoresis step, such as western blot. For these methods, the sample can also be an intact tissue such as a tissue section.

In additional embodiments, the present invention is directed to a method of detecting any of the invention polynucleotides in a sample. The method comprises treating the sample with a second polynucleotide that specifically hybridizes with the polynucleotide of interest, then determining if the second polynucleotide specifically hybridized with a component of the sample. In some embodiments, the treating step is by a Southern hybridization method or a northern hybridization method.

The present invention is also directed to an additional method of detecting any of the invention polynucleotides in a sample. The method comprises treating the sample with a second polynucleotide that specifically hybridizes with the polynucleotide of interest, then performing a polymerase amplification method such as PCR or RT/PCR.

The present invention is further directed to methods of enhancing CREB binding protein (CBP)-mediated activation of transcription in a cell. The methods comprise treating the cell with one of the polypeptide, polynucleotide, or antibody compositions described above. As with previous methods, the cell can be part of a mammal, including a human.

The present invention is still further directed to a method for identifying a compound that modulates SRCAP protein function. The method comprises determining whether the candidate modulator compound alters the interaction of the SRCAP with CBP.

Additionally, the invention is directed to methods for identifing a compound that modulates SRCAP function. The methods comprise assessing the activity of SRCAP as an ATPase, in CBP interaction and transcriptional co-activation, in transcriptional activation without CBP, or in DNA binding in the presence of the candidate modulator compound.

In additional embodiments, the present invention is directed to a method for treating a patient having a disease involving a function affected by SRCAP protein. The method comprises administering an invention polypeptide or polynucleotide to the patient. In preferred embodiments, the patient is a mammal, including humans. Preferred functions are insufficient transcription of a gene selected from the group consisting of a gene mediated by CBP co-activation, a DEAD box RNA dependent helicase, an adenoviral DBP protein, β-actin and a nuclear receptor.

In further embodiments, the present invention is directed to a method for treating a patient having a disease mediated by SRCAP-activated transcription. The method comprises administering to the patient a compound that decreases SRCAP activity in the patient. Preferred compounds here are antibodies, antisense polynucleotides or ribozymes. In preferred embodiments, the disease is a virus infection, for example infection with adenovirus, HCV, HTLV-1, HIV-1, Epstein-Barr virus, cytomegalovirus or hepatitis B virus.

BRIEF DESCRIPTION OF THE DRAWINGS

FIG. 2B shows a comparison of SRCAP conserved ATPase domains to other Snf2 related genes. The position of the amino acids at the C-terminal side of each conserved domain is indicated.

FIG. 5 is two graphs that demonstrate that SRCAP functions as an ATPase. The ability of SRCAP to function as an ATPase was assessed by measuring the ability of immunoprecipitated SRCAP to hydrolyze ATP.

In FIG. 10A, in vitro translated $^{35}$S-methionine labeled CMV-SRCAP was subjected to pull-down analysis with His-NS5A or His-NMP-1 (negative control) fusion protein. Ten percent of the input protein (in vitro translated CMV-SRCAP) was loaded in the gel for comparison. The image was edited from the same x-ray film. In FIG. 10B, in vivo coimmunoprecipitation of endogenous SRCAP with HCV NS5A is demonstrated. HepG2 cells were transfected with NS5A expression plasmid or empty vector plasmid. Cells were lysed after 48 h. Vector transfected (lane 1) and NS5A transfected (lane 2) cell lysates were immunoprecipitated with a monoclonal antibody to SRCAP. Immunoprecipitates were separated by SDS-7.5% PAGE and immunoblotted with a rabbit antibody to NS5A. A secondary antibody conjugate (anti-rabbit IgG/horseradish peroxidase, Amersham) was used for detection of the peroxidase signal by chemiluminescence (ECL). The molecular weight of the NS5A band was also ascertained from the migration of standard protein molecular weight markers. The same blot was reprobed with SRCAP specific antibody for detection of endogenous SRCAP (lanes 1 and 2).

DESCRIPTION OF THE PREFERRED EMBODIMENTS

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

The present invention is directed to the identification and use of a newly discovered protein, SRCAP, or Snf2 Related CBP Activator Protein, which affects transcription. SRCAP interacts with CREB binding protein (CBP) amino acids 227–460 to enhance the ability of CBP to activate transcription. SRCAP is also able to activate transcription without CBP.

SRCAP is a Snf2 family member. The Snf2 family consists of a number of proteins with diverse functions including remodeling chromatin, regulation of transcription, and DNA repair (Reviewed in Cote, et al., 1994, *Science* 265, 53–60). Some Snf2 family members serve as part of chromatin remodeling complexes such as the yeast SWI/SNF assembly, which reorganize chromatin structure during transcription activation (Travers, 1999, *Cell* 96, 311–314). This reorganization facilitates the access of DNA binding proteins. In this context, Snf2 family members are also called SWI2/SNF2. SWI2/SNF2 family members include Drosophila Brm, yeast Sth1, and human BRG1 and hBrm.

A common feature of the Snf2 family of proteins is the presence of a highly conserved domain called the Snf2 domain, which functions as an ATPase (Laurent et al., 1993, *Genes Dev.* 7, 583–591). This ATPase domain consists of seven highly conserved motifs interspersed with variable spacers of non-conserved sequences. As shown by the comparison of the ATPase motifs of various Snf2 family members in FIG. 2B, the SRCAP ATPase domain is clearly a Snf2 domain.

Figure 2A:
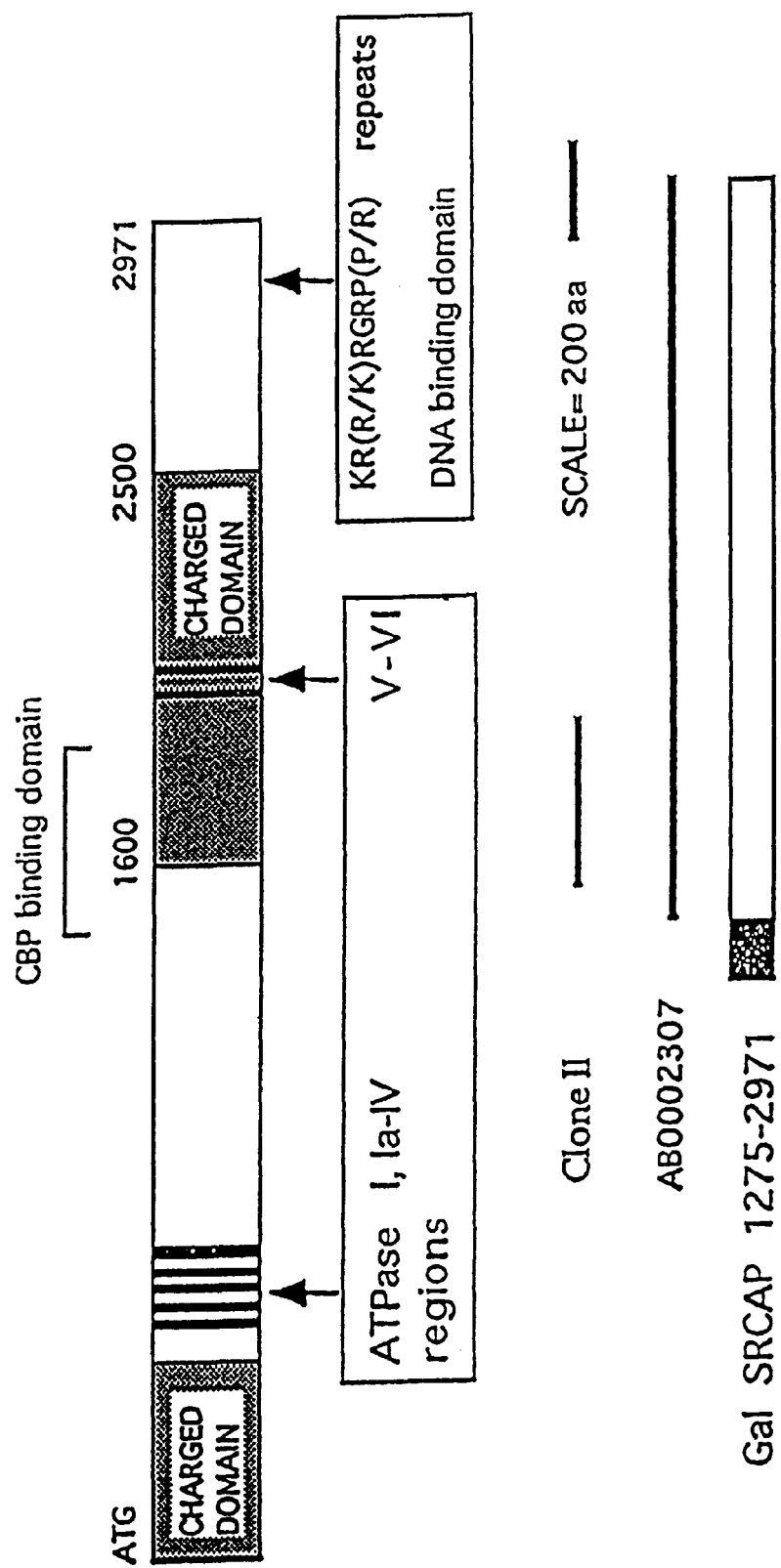
FIG. 2A is a schematic of the SRCAP gene, where domains identified within the 2971 amino acid SRCAP are indicated including: two highly charged domains, the putative DNA binding domain, the CBP binding domain, and the position of the regions which make up the conserved ATPase domains (I, Ia-VI). The position of clone 11 identified by the yeast two hybrid screen as interacting with CBP and the position of the AB0002307 cDNA are also shown.

Thus, in some embodiments, the present invention is directed to a SRCAP protein. SRCAP can be distinguished from any other known proteins by its ability to act as a CBP co-activator in combination with its ATPase activity. SRCAP is also capable of mediating transcription without CBP. SRCAP can be identified. e.g., by two-hybrid analysis of a cDNA library for encoded polypeptides that interact with CBP. See, e.g., Example 1, where a SRCAP is identified from a HeLa cell library using yeast and mammalian two-hybrid systems. An open reading frame (orf) derived from HeLa cell SRCAP cDNA encodes the 3118 amino acid SEQ ID NO:1; the 2971 amino acid SEQ ID NO:2 is the amino acid sequence encoded by the same cDNA, starting from the presumptive initiator ATG, which is the first ATG in the open reading frame that occurs in the context of the consensus Kozak sequence (Kozak, 1989, *J. Cell Biol.* 108, 229–241). As shown in FIG. 2A, the conserved ATPase domain is created by combining seven discontinuous regions. These regions are termed Box I, covering the 12 amino acids 442–453 (GILADEMGLGKT; SEQ ID NO:3); Box 1A, covering the 12 amino acids 474–485 (LIIVTSVMLNW; SEQ ID NO:4); Box II, covering the 14 amino acids 542–555 (WRYLILDEAQNIKN; SEQ ID NO:5); Box III, covering the 23 amino acids 572–594 (RLLLTGTPLQNSLMELWSLMHFL; SEQ ID NO:6); Box IV, covering the 12 amino acids 639–650 (FLLRRVKVDVEK; SEQ ID NO:7); Box V, covering the 29 amino acids 1855–1883 (FILSTRSGGVGLNLTGADTVVFYDSDWNP; SEQ ID NO:8); and Box VI, covering the 22 amino acids 1886–1883 (DAQAQDRCHRIGQTRDVHIYRL;SEQ ID NO:9)(FIG. 2B). These conserved boxes combine to create an ATPase in SRCAP that is similar to the ATPase in other Snf2 family members. However, there are differences between the SRCAP ATPase and at least one other Snf2 family member ATPase. For example, the SRCAP ATPase activity is apparently not stimulated by DNA, as opposed to the ATPase activity of recombinant yeast Snf2, which is stimulated five-fold by DNA (Laurent et al., 1993, *Genes Dev.* 7, 583–591). However, it is believed that substitutions can be made in the SRCAP ATPase conserved sequences to replace any of the ATPase amino acids with amino acids in equivalent positions (as in FIG. 2B) from any other Snf2 family member, while still retaining ATPase activity. Also, it is believed any or all of these conserved regions can be replaced in whole or in part with the equivalent regions of any other Snf2 family member, while still retaining ATPase activity. For example, the ATPase of yeast Snf2 can replace the SRCAP ATPase to create a SRCAP with an ATPase that is stimulated by DNA.

Other regions of SRCAP, as identified herein, are functionally important The approximately first (N-terminal) 400 amino acids, as well as the amino acids about 1600–2500 are highly charged, being made up of clusters of acidic and basic residues (FIG. 2A). These highly charged regions are important for activating transcription. Based on mammalian two-hybrid studies using hybrid clones encoding various fragments of the SRCAP cDNA, the first highly charged region is necessary for direct CREB activation, whereas the second highly charged region is necessary for CBP co-activation of transcription. In addition, the C-terminal domain of SRCAP contains four copies of the motif KR(R/K)RGRP(P/R) (FIG. 2A), which is found in several DNA binding proteins, for example the chromosomal proteins D1 and HMG-1, where it apparently mediates the binding of these proteins to A-T rich regions by contacts in the minor groove of DNA (Ashley et al., 1989, *J. Biol. Chem.* 264, 8394–8401; Churchill et al., 1991, *TIBS* 16, 92–97). A similar motif is found in the C-terminal end of human homologs of yeast Snf2 (hSnf2α and β) and within the DNA binding domain of the Snf2 family protein CHD 1 (Chiba et al., 1994, *Nucleic Acids Res.* 22, 1815–1820; Stokes et al., 1995, *Mol. Cell. Biol.* 15, 2745–2753). An additional area of SRCAP that is functionally important is a region within amino acids 1380–1699. This area interacts with CBP, allowing SRCAP to serve as a co-activator of CBP-mediated transcription. In addition, the areas within amino acids 1–1186 and 2316–2971 are at least two additional domains involved in activation of transcription without the help of CBP (see Example 3).

Reference to SRCAP herein should be construed to include Snf2 family members of any origin that are substantially homologous and biologically equivalent to human SRCAP characterized and described herein. Such proteins may be naturally occurring or have modifications that do not occur in any naturally occurring protein. Included are naturally occurring SRCAPs from any mammal or other vertebrates. A search of yeast and Drosophila genomic databases did not find sequences that were homologous to the SRCAP human cDNA sequence. Thus, it is believed that SRCAP is not present in insects or fungi. However, GenBank has sequences for bovine SRCAP (Accession No. AW660374) and mouse SRCAP (AZ079669). Therefore, SRCAP would be expected to be present in all mammals, and perhaps other vertebrates.

The term "substantially homologous" as used above means that the degree of sequence identity between SRCAP orthologs from human, mouse, or any other species, is greater than that between paralogs such as human SRCAP and human Snf2 or between any other two different Snf2 family members. To determine percent homology between two sequences, the two sequences are first aligned. A common method for aligning sequences is by the Clustal method (Higgins et al., 1992, *Cabios* 8, 189–191), as used for example in the Lasergene biocomputing software (DNASTAR, INC, Madison Wis.). Percent homology is then determined by calculating the number of identical amino acids in the aligned sequences is divided by the total number of amino acids in the reference sequence. Any sequence homologies discussed herein is determined after alignment by the Clustal method.

The term "biologically equivalent" as used above means that the SRCAP compositions of the present invention are capable of ATPase activity and co-activation of CBP, although they may not necessarily perform these functions to the same degree as the human SRCAP identified herein. While human SRCAP exemplified herein contains functions other than ATPase activity and co-activation of CBP (e.g., DNA binding, transcriptional activation without CBP), it is anticipated that some SRCAP variants, either naturally occurring or man made, could be deficient in these functions.

Based on the homology that exists between human SRCAP as identified herein and bovine and mouse SRCAPs given in GenBank as Accession Nos. AW660374 and AZ079669, respectively, as well as the homology between particular Snf2 family members of different species (Woodage et al., 1997, *Proc. Natl. Acad. Sci. USA* 94, 11472–11477), it is expected that the non-conserved regions of human SRCAP would have at least about 90% homology to the non-conserved sequences of SRCAP of other mammalian species, and at least about 80% homology among the non-conserved sequences of SRCAP from any species. However, the SRCAP proteins from other species can be identified not only by homology to other SRCAPs, but also by the ability of the protein to serve as a transcriptional co-activator with CRP along with its ATPase activity.

The present invention additionally includes the identification and use of the various portions of SRCAP having an identifiable finction (i.e., ATPase, CBP interaction and transcriptional co-activation, transcriptional activation without CBP, and DNA binding). Thus, each of these functions, either with or without any of the other functions, can be utilized, e.g., in chimeras with other Snf2 family members to create novel Snf2 family members, or in two-hybrid interaction studies.

It is recognized that naturally occurring SRCAP can be modified, wherein certain substitutions can be made in the amino acid sequence while still substantially retaining SRCAP biological activity. Thus, conservatively substituted SRCAPs, or portions thereof, which are biologically equivalent to naturally occurring SRCAPs or portions are also within the scope of the present invention. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

Certain non-conservative amino acid substitutions of SRCAP or SRCAP portions can also be identified as providing polypeptides with biological equivalence to naturally occurring SRCAP. For example, substitution of an amino acid residue in a SRCAP ATPase with a non-conservative amino acid at the same position in the ATPase of another Snf2 family member would be expected to provide a functional ATPase.

Naturally occurring SRCAPs can be discovered from any mammalian or other vertebrate species by known methods, for example by identifying polynucleotide sequences (genomic, mRNA, or cDNA) from that species that are capable of selective hybridization with a known SRCAP polynucleotide or fragment. By selective hybridization or specific hybridization it is meant that a polynucleotide preferentially hybridizes to a target polynucleotide. A polynucleotide that specifically hybridizes to a reference sequence can be of any length, for example, about 15 nucleotides up to about 100 nucleotides or up to about 1000 nucleotides or up to about 10,000 nucleotides or even greater. Specific hybridization to identify other mammalian or other vertebrate SRCAPs is preferably done under moderate or high stringency conditions which, as well understood by those skilled in the art, can readily be determined by adjusting several factors during hybridization and during the washing procedure, including temperature, ionic strength, length of hybridization or washing times, and concentration of formamide (see for example, Sambrook, Fritsch and Maniatis., *Molecular Cloning a Laboratory Manual*, 2d Ed., Vols. 1–3, Cold Spring Harbor Laboratory Press, Plainview N.Y., 1989). However, as is known, hybridization conditions may be adjusted without undue experimentation depending various factors including the length of the SRCAP probe, the region of the SRCAP gene where the probe was obtained, and the expected homology of the SRCAP gene being sought.

As previously discussed, any of the functional portions of SRCAP (e.g., ATPase, CBP interaction and transcriptional co-activation, transcriptional activation without CBP, and DNA binding) can be utilized with other polypeptides to form chimeras that confer the SRCAP function. Nonlimiting examples of such chimeras include: a SRCAP with a Snf2 ATPase to confer the ability of the Snf2 ATPase to be stimulated by DNA; an Snf2 with its ATPase replaced with a SRCAP ATPase to eliminate the ability of the Snf2 to be stimulated by DNA; and a chimera of a portion of SRCAP with the activation domain of the yeast transcriptional activator protein GAL4, for use in determining whether particular proteins interact with that portion of SRCAP in two-hybrid systems, as described in Chien et al., 1991, *Proc. Natl. Acad. Sci. USA* 88:9578–9582, and in Examples 1–3 herein. Several particular SRCAP chimeras are also identified in the Examples. The latter chimera is especially useful for determining whether any particular polypeptide interacts with SRCAP. Nonlimiting examples of polypeptides that could be tested in this way are transcription factors, other co-activators, and hormones.

Fragments of SRCAP are also encompassed by the present invention. Such fragments may be of any length but preferably retain at least one of the biological functions of SRCAP or are antigenic. The minimum length of such biologically active or antigenic fragments can readily be determined by those skilled in the art using known techniques. Preferably, the minimum length of fragments of SRCAP is at least 8 amino acids, more preferably, at least 10 amino acids, still more preferably at least 12 amino acids, even still more preferably at least 15 amino acids and most preferably, at least 20 amino acids or greater.

Antigenic fragments of SRCAP are capable of eliciting SRCAP-specific antibodies when administered to a host animal. Included are smaller fragments that require conjugation to a carrier molecule to be immunogenic. Typically, antigenic fragments will be at least 5 or 6 amino acids in length and may be any length up to the full length of SRCAP. Preferably an antigenic fragment is 8, more preferably 10, still more preferably 12 amino acids in length, even still more preferably 15 amino acids in length and most preferably 20 amino acids or more in length. A preferred SRCAP fragment for producing anti-SRCAP antibodies is SRCAP amino acids 2733–2971 of SEQ ID NO:2, which is the C-terminal end of the translated GenBank cDNA sequence AB0002307, described in Example 1.

Methods for preparation of SRCAP or a fragment thereof include, but are not limited to chemical synthesis, recombinant DNA techniques or isolation from biological samples. SRCAP can be prepared by any of these methods without undue experimentation. Chemical synthesis of a peptide can be performed, for example, by the classical Merrifeld method of solid phase peptide synthesis (Merrifeld, *J Am Chem Soc* 85:2149, 1963) or the FMOC strategy on a Rapid Automated Multiple Peptide Synthesis system (DuPont Company, Wilmington, DE) (Caprino and Han, *J Org Chem*37:3404, 1972).

The present invention is also directed to polynucleotides encoding the above-described SRCAP, modified SRCAP, or SRCAP fragments, or chimeras comprising a portion of SRCAP. Included here are polynucleotides that are double stranded or single stranded, DNA or RNA, and coding strand or complementary strand. An example is SEQ ID NO:10, which is a cDNA open reading frame encoding human SRCAP, and which encodes SEQ ID NO:1. Another example is SEQ ID NO:11, which is the cDNA of SEQ ID NO:10 truncated to begin at the initiator ATG codon, and which encodes SEQ ID NO:2. However, due to the degeneracy of the genetic code, any particular SRCAP polypeptide or fragment, or any chimera comprising portions of SRCAP, can be encoded by numerous polynucleotide sequences, which can be readily identified by the skilled artisan. For various applications such as gene therapy or antisense treatment, any or all of the nucleotides of the polynucleotides can also be substituted with non-naturally occurring nucleotides to produce a nucleic acid mimic, as is known in the art (see, e.g., Nielsen, 2000, *Pharmacol. Toxicol.* 86, 3–7).

Included in the polynucleotides of the invention are fragments of a SRCAP gene coding region or the complement, for example fragments of SEQ ID NO:10. These fragments can be used, e.g., as probes, primers (including PCR primers), antisense agents and for other purposes that would be known to the skilled artisan. They can be as short as 10 nucleotides long. More preferably, they are at least 20 nucleotides long, even more preferably at least 45 nucleotides long.

The present invention extends to the preparation of antisense nucleotides and ribozymes that may be tested for the ability to interfere with any particular SRCAP function. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. Reviews of antisense technology include: Baertschi, 1994, *Mol. Cell. Endocrinol.* 101, R15–R24 (1994); Crooke et al., 1996, *Annu. Rev. Pharmacol. Toxicol.* 36, 107–129 (1996); Alama et al., 1997, *Pharmacol. Res.* 36, 171–178. In the cell, they hybridize to that mRNA, forming a double stranded DNA:RNA or RNA:RNA molecule. The cell will not translate an mRNA in this double-stranded form. Therefore, antisense nucleic acids interfere with the expression of mRNA into protein. Oligomers of about fifteen nucleotides and molecules that hybridize to the AUG initiation codon are particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al. 1988, *J. Exp. Med.* 168,1237). Preferably, synthetic antisense nucleotides contain phosphoester analogs, such as phosphorothiolates, or thioesters, rather than natural phosphoester bonds. These unnatural phosphoester bond analogs are more resistant to degradation, increasing the stability, and therefore the efficacy, of the antisense nucleic acids.

In the genetic antisense approach, expression of the wild-type allele is suppressed because of expression of antisense RNA. This technique has been used to inhibit TK synthesis in tissue culture and to produce phenotypes of the Kruppel mutation in Drosophila, and the Shiverer mutation in mice (Izant et al., 1984, *Cell* 36,1007–1015; Green et al., 1986, *Annu. Rev. Biochem.* 55, 569–597; Katsuki et al., 1988, *Science* 241, 593–595). An important advantage of this approach is that only a small portion of the gene need be expressed for effective inhibition of expression of the entire cognate mRNA. The antisense transgene can be placed under control of its own promoter or another promoter expressed in the correct cell type, and placed upstream of a polyA site such as the SV40 polyA site.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it. Recent reviews include Shippy et al., 1999, *Mol. Biotechnol.* 12, 117–129 (1999); Schmidt, 1999, *Mol. Cells* 9, 459–463; Phylactou et al., *Meth. Enzymol.* 313, 485–506 (2000); Oketani et al., *J. Hepatol.* 31, 628–634 (1999). Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Another aspect of the invention relates to (e.g. expression) vectors suitable for the replication of the above polynucleotides, in particular a DNA or RNA polynucleotide, and including antisense and ribozymes. The vectors may be, for example, plasmid, virus or phage vectors provided with an origin of replication, optionally a promoter for the expression of the polynucleotide and optionally a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA, or used to transfect or transform a host cell. The vector may also be adapted to be used in vivo, for example in a method of gene therapy.

Preferably, the DNA in the vector is operably linked to a control sequence that is capable of providing for the expression of the coding sequence by a host cell. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. Such vectors may be transformed or transfected into a suitable host cell to provide for expression of a polypeptide of the invention.

Another aspect of the invention relates to recombinant cells transformed or transfected with the above-described vectors. This may be for the replication and expression of a polynucleotide according to the invention, including the sequence of SEQ ID NO:10 or 11, or a fragment thereof. The cells can be chosen to be compatible with the vector without undue experimentation, and may for example be bacterial, yeast, insect or mammalian. The cells can also be a part of a living animal, for example a vertebrate or mammal.

An additional aspect of the invention provides a process for preparing a SRCAP polypeptide which comprises cultivating a host cell transformed or transfected with an expression vector as described above under conditions providing for expression (by the vector) of a coding sequence encoding the polypeptide, and recovering the expressed polypeptide.

SRCAP or SRCAP fragments may be used as an immunogen to generate antibodies that recognize HCV. Such antibodies include but are not limited to polyclonal, monoclonal, chimeric, single chain, Fab fragments, and products of a Fab expression library. Various procedures known in the art may be used for the production of polyclonal antibodies to HCV.

For the production of antibodies, various host animals, including but not limited to rabbits, mice, rats, sheep, goats, etc, can be immunized, preferably by injection with the SRCAP or SRCAP fragment. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

Polyclonal antibodies can be prepared by immunizing rabbits or other animals by injecting antigen followed by subsequent boosts at appropriate intervals. The animals are bled and sera assayed against purified SRCAP usually by ELISA or by bioassay based upon the ability to block the action of SRCAP. When using avian species, e.g. chicken, turkey and the like, the antibody can be isolated from the yolk of the egg.

For preparation of monoclonal antibodies directed toward SRCAP, any technique that provides for the production of antibody molecules by continuous cell lines in culture may be used. These include but are not limited to the hybridoma technique originally developed by Kohler and Milstein (1975, *Nature* 256, 495–497), as well as the trioma technique, the human B-cell hybridoma technique (Kozbor et al., 1983, *Immunology Today* 4, 72; Cote et al., 1983, *Proc. Natl. Acad Sci. U.S.A.* 80, 2026–2030), and the EBV-hybridoma technique to produce human monoclonal antibodies (Cole et al., 1985, in *Monoclonal Antibodies and Cancer Therapy,* Alan R. Liss, Inc., pp. 77–96). In an additional embodiment of the invention, monoclonal antibodies can be produced in germ-free animals (International Patent Publication No. WO 89/12690, published 28 December 1989). Also, chimeric antibodies (Morrison et al., 1984, *J. Bacteriol.* 159,870; Neuberger et al., 1984, *Nature* 312, 604–608; Takeda et al., 1985, *Nature* 314, 452454) can be made, e.g., by splicing the genes from a mouse antibody molecule specific for SRCAP together with genes from a human antibody molecule of appropriate biological activity. Such human or humanized chimeric antibodies are preferred for use in therapy of human diseases or disorders (described infra), since the human or humanized antibodies are much less likely than xenogenic antibodies to induce an immune response, in particular an allergic response, themselves.

Single chain antibodies (U.S. Pat. Nos. 5,476,786 and 5,132,405 to Huston; U.S. Pat. No. 4,946,778) can also be produced that are SRCAP-specific. An additional embodiment of the invention utilizes the techniques described for the construction of Fab expression libraries (Huse et al., 1989, *Science* 246, 1275–1281) to allow rapid and easy identification of monoclonal Fab fragments with the desired specificity.

Antibody fragments that contain the idiotype of the antibody molecule can also be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

When short SRCAP fragments such as oligopeptides (defined herein as a polypeptide less than about 25 amino acids long) or short polypeptides are selected as candidates for the production of an antibody to SRCAP, it is preferred that the fragments are from hydrophilic regions of SRCAP, which are likely to be exposed in the mature protein. As is well known, when a small (e.g., <10,000 MW or about 75 amino acids) SRCAP fragment is used as an antigen, an immune response can be better elicited by immunizing with a conjugate of the fragment with an immunogenic carrier molecule such as bovine serum albumin or keyhole limpet hemocyanin.

Antibodies can be raised against SRCAP fragments that include one or more of the conserved regions (e.g., an ATPase box) such that the antibody can cross-react with other Snf2 family members. Alternatively, the antibodies can be raised against unique fragments of SRCAP in order to produce antibodies that do not cross-react with other proteins.

The polypeptide, polynucleotide and antibody compositions described above, including SRCAP, SRCAP fragments, modified SRCAP, chimeras comprising SRCAP portions, polynucleotides encoding and complementary to these polypeptides, antisense and ribozyme polynucleotides, vectors and host cells comprising the various polynucleotides, and antibodies reacting to the polypeptides, are variously useful for diagnostic and therapeutic purposes.

Due to the biological importance of SRCAP, it would be useful to be able to determine whether the SRCAP protein or mRNA is present in a sample. Preferably, the determination would be quantitative. Such methods are provided by the present invention.

SRCAP protein can be identified and/or quantified using an antibody. As previously discussed, the antibody is preferably prepared against a hydrophilic portion of SRCAP. The antibody is also preferably specific for SRCAP, such that no other protein in the sample of interest would be expected to cross-react with the antibody. However, antibodies directed against a region that is conserved between SRCAP and other proteins, such as the ATPase, would be useful in generating antibodies for identifying that group of proteins. For example, an antibody against the SRCAP ATPase would be expected to cross-react with other Snf2 family members, and would be useful for determining the presence of Snf2 family members in general.

Thus, the present invention provides immunoassay methods of detecting SRCAP in a sample. The method comprises treating the sample with an antibody that binds to the SRCAP, then determining whether the antibody specifically binds to a component in the sample, where specific binding indicates the presence of SRCAP. The sample can be derived from tissue or fluid, such as blood or urine. When it is desired to detect SRCAP in a tissue, the tissue is preferably first prepared, e.g., by grinding, etc., in order for substantially all of the SRCAP from the tissue to be available for antibody binding.

The method is not narrowly limited to any particular immunoassay, and may be readily adapted to, e.g., western blotting, immunodiffusion, immunoelectrophoresis, ELISA, radioimmunoassay (RIA), or fluorescence polarization immunoassay. See, e.g., *Basic and Clinical Immunology*, Sites and Terr, eds., Appleton & Lange, Norwalk, Conn. pp 217–262, 1991. These assays can also be utilized in protein microarrays to simultaneously analyze for many proteins including SRCAP (Leuking et al., 1999, *Anal Biochem* 270, 103–11). Qualitative and quantitative adaptations of any of these assays for use in detecting SRCAP can be devised without undue experimentation.

Several of the above methods can also be utilized to localize SRCAP in tissue sections, by methods well known in the art.

The present method also provides assays for determining the presence of SRCAP mRNA in a sample. To detect the presence of mRNA encoding SRCAP, a sample is obtained, e.g., from a patient or from cells in culture. The sample can be, e.g., from blood or from a tissue biopsy sample. The sample is preferably treated to extract the mRNA contained therein. The resulting mRNA from the sample may also be subjected to gel electrophoresis or other size separation techniques.

In some embodiments, the mRNA of the sample is contacted with a polynucleotide probe to form hybrid duplexes. The probe, which is complementary to a portion of the SRCAP mRNA, may be as short as ten nucleotides long. However, in preferred embodiments, the probe is at least 100 nucleotides long. The probes can be made by any method known in the art, for example by nick translation, random primer, or PCR methods. Preferably, the probe is labeled with any useful detectable label known in the art, including radioactive labels such as $^{32}$p, fluorescent labels such as 5'-tetramethylrhodamine, or fluorescein dyes, or hapten labels such as digoxigenin. The label allows detection of the duplex resulting from the hybridization of the labeled probe with SRCAP mRNA. In these hybridization methods, the mRNA is usually immobilized, e.g., on a membrane, before treatment with the probe, such as in dot blot or northern blot methods, which are well known in the art. These assays can also be utilized in microarrays to simultaneously analyze for many mRNAs including SRCAP mRNA (Bowtell et al., 1999, *Nat Genet* 21, 25–32).

High stringency conditions can be used in order to prevent false positives, that is hybridization to non-SRCAP nucleotide sequences. When using sequences that are not perfectly complementary to an SRCAP-encoding polynucleotide or a fragment thereof, less stringent conditions could be used; however, this would be a less preferred approach because of the likelihood of false positives.

Alternatively, to detect mRNA encoding SRCAP, a polymerase amplification method such as polymerase chain reaction (PCR) or reverse transcriptase/polymerase chain reaction (RT/PCR) can be used. See, e.g., Example 2. The PCR and RT/PCR methods are well known in the art, and are preferred over the previously described hybridization methods when small samples are used or when greater sensitivity is desired.

A SRCAP target sequence in the reverse transcribed cDNA can be amplified and detected using any other known methodology such as ligase chain reaction methods, including gap LCR (G-LCR) and other variations, or self-sustained sequence replication (3SR) and its various modifications. In addition, the SRCAP mRNA can be detected directly by asymmetric gap LCR (AG-LCR). See, e.g., Leckie et al., "Infectious Disease Testing by Ligase Chain Reaction" in *Molecular Biology and Biotechnology*, R. A. Myers, ed., pp. 463–466, VCH Publishers, 1995.

As is well known, the above methods can be adapted, without undue experimentation, for the detection of various other polynucleotides of the present invention, for example SRCAP cDNAs or fragments of the SRCAP gene in genomic DNA. Such methods are useful, e.g., in various molecular biological methods such as cloning or subcloning efforts.

In other embodiments, the present invention is directed to methods for identifying a compound that modulates SRCAP protein finction. The method comprises assessing the activity of SRCAP as a transcriptional activator, a modulator of CBP fiction, or an ATPase in the presence of the candidate modulator. Preferably, the SRCAP activity in the presence of the candidate modulator is compared with SRCAP activity in the absence of the modulator. The various activities of SRCAP can be determined by any method known in the art. Several of these methods are utilized in the Examples, for example, methods for determining SRCAP activity as a transcriptional activator; methods for determining modulation of CBP function; and methods for measuring ATPase activity.

The polypeptide, polynucleotide, and antibody compositions of the present invention can variously be administered to a mammalian or other vertebrate patient, including humans, for therapeutic purposes. For these purposes, the compositions preferably also comprise a pharmaceutically acceptable carrier or diluent. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. The formulations may conveniently be presented in unit dosage form and may be prepared by any of the methods well known in the art of pharmacy. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then, if necessary, shaping the product.

The polypeptides, polynucleotides, and antibodies of the present invention can also be linked or conjugated with agents that provide desirable pharmaceutical or pharmacodynamic properties. For example, they can be coupled to any substance known in the art to promote penetration or transport across the blood-brain barrier such as an antibody to the transferring receptor, and administered by intravenous injection. (See for example, Friden et al., *Science* 259:373–377, 1993). Furthermore, these compositions can be stably linked to a polymer such as polyethylene glycol to obtain desirable properties of solubility, stability, half-life and other pharmaceutically advantageous properties. (See for example Davis et al. *Enzyme Eng* 4:169–73, 1978; Burnham, *Am J Hosp Pharm* 51:210–218, 1994).

For nonparenteral administration, the compositions can also include absorption enhancers that increase the pore size of the mucosal membrane. Such absorption enhancers include sodium deoxycholate, sodium glycocholate, dimethyl-β-cyclodextrin, lauroyl-1-lysophosphatidylcholine and other substances having structural similarities to the phospholipid domains of the mucosal membrane.

Such excipients are those substances usually and customarily employed to formulate dosages for parenteral administration in either unit dosage or multi-dose form or for direct infusion into the cerebrospinal fluid by continuous or periodic infusion.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that the composition be administered to cells in the central nervous system, administration can be with one or more agents capable of promoting penetration of SRCAP across the blood-brain barrier.

Dose administration can be repeated depending upon the pharmacokinetic parameters of the dosage formulation and the route of administration used.

It is also contemplated that certain formulations containing SRCAP are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifiing and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface-active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art based on the activity of SRCAP for a particular cell type in vitro. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In some embodiments of this invention, SRCAP may be therapeutically administered by implanting into patients vectors or cells capable of producing a biologically-active form of SRCAP or a precursor of SRCAP, i.e. a molecule that can be readily converted to a biological-active form of SRCAP by the body. In one approach cells that secrete SRCAP may be encapsulated into semipermeable membranes for implantation into a patient. The cells can be cells that normally express SRCAP or a precursor of SRCAP or the cells can be transformed to express SRCAP or a precursor thereof. It is preferred that the cell be of human origin and that the SRCAP be human SRCAP when the patient is human. However, the formulations and methods herein can be used for veterinary as well as human applications and the term "patient" as used herein is intended to include human and veterinary patients.

Some embodiments of the invention are directed to methods of modulating transcription in a cell. The methods comprise treating the cell with an amount of a polypeptide, polynucleotide, or antibody composition of the invention sufficient to modulate transcription of the cell. The cell can be a cell in culture (in vitro) or within a living mammal or other vertebrate, including humans (in vivo). Ex vivo applications are also envisioned, where cells are removed from a mammal or other vertebrate, treated with the invention composition, then reimplanted in the vertebrate.

The method is useful for modulating transcription of any gene that is directly or indirectly affected by transcription factors or co-activators with which SRCAP interacts. Non-limiting examples of such transcription factors or co-activators include CBP and the transcription factors and co-activators affected by CBP (see Example 1), DEAD box RNA dependent helicases (see Example 3), adenoviral DBP protein, β-actin, and glucocorticoid receptor (GR) and other nuclear receptors (see Example 3). However, the method encompasses any transcription factor or co-activator affected by SRCAP, whether now known or later discovered.

Figure 1:
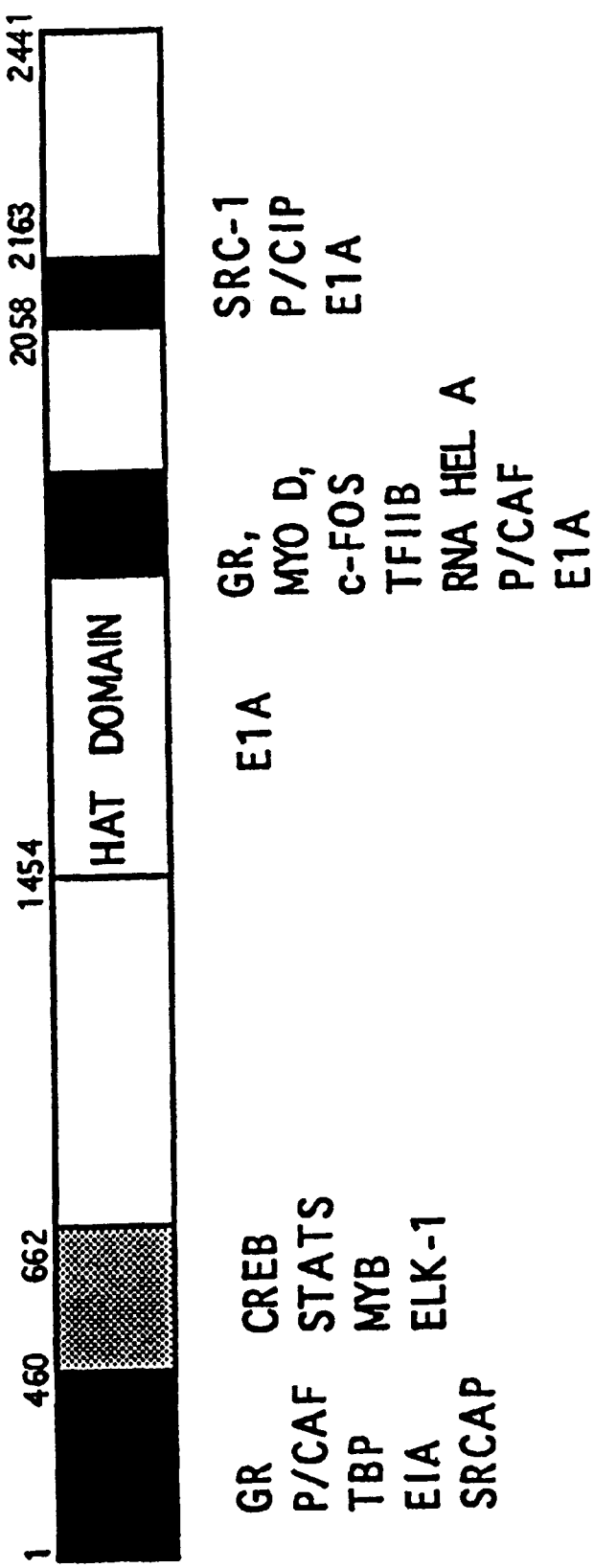
FIG. 1 depicts domains within CBP that bind to other proteins. The discovery of the SRCAP binding domain is part of the present invention.

The co-activation of CBP by SRCAP is significant because of the large number of transcription factors for which CBP is a co-activator. As discussed in the Background of the Invention section and illustrated in FIG. 1, CBP interacts with, for example, GR, P/CAF, p/CIP, CREB, STATs, TATA-binding protein (TBP), TFIIB, RNA helicase A, estrogen receptor, progesterone receptor, retinoic acid receptor, vitamin D receptor, glucocorticoid receptor, PPARγ receptor, jun, fos, smad, c-myb, NF-1 C, GATA-1, and p53. Based on these interactions and other known effects of CBP, SRCAP interaction with CBP would be expected to affect a wide variety of systems, including central nervous system development, potentially alleviating the deleterious effects of Rubinstein-Taybi syndrome; acute myeloid leukemia; sexual maturation; bone development; lipid metabolism; regulation of energy metabolism; pancreatic islet morphogenesis; liver development; p53 mediated apoptosis; glucocorticoid mediated repression of NF-kappaB-mediated inflammation; various central nervous system disorders such as addiction; hormonal and behavioral cycles; memory; and long-term effects of activity dependent plasticity at glutamatergic neurons. It would be expected that selective targeting of any of the above particular effects can be achieved by various methods, including the treatment of only specific organs or cell types. Such specific treatment can include the use of targeting methods such as those that utilize viral or microorganism tropism to particular organs or cell types, or targeted binding proteins, for example chimeras of SRCAP and monoclonal antibodies to target specific sites where the antibodies bind.

SRCAP would also be expected to affect several aspects of virus infection. Examples include the interaction of the HTILV-1 protein TAX with CREB; the interaction of CBP with the HIV-1 Tat protein; various effects of adenovirus infection due to the interaction of CBP with the adenovirus E1A protein; various effects of Epstein-Barr virus due to the interaction of CBP with the viral zta protein; various effects of cytomegalovirus due to the interaction of CREB with the enhancer of the viral IE1/2 gene; various effects of hepatitis B virus (HBV) due to the interaction of CREB with the viral protein pX; and various effects of hepatitis C virus due to the interaction of SRCAP with the viral protein NS5A (see Example 2).

The methods of modulating transcription in a cell described herein can be directed toward the reduction of transcription or the enhancement of transcription. Transcription can be enhanced in a target cell by treating the cell with various polypeptide compositions, including SRCAP and SRCAP fragments that, e.g., interact with CBP (fragments comprising $SRCAP_{1380-1699}$) or activate transcription in the absence of CBP (fragments comprising $SRCAP_{1-1186}$ or $SRCAP_{2316-2371}$). The SRCAP or SRCAP fragments can be administered to the cell by way of treatment with the polypeptides themselves, by therapeutic methods well known in the art; alternatively, the fragments can be administered through the translation of a polynucleotide that is administered as a gene therapy agent. The polynucleotides can be delivered through a DNA or RNA virus, or by direct treatment with a polynucleotide (Ilan et al., 1999, Sem. Liver Disease 19, 49–59; Widera et al., 2000, J. Immunol. 164, 4635–4640; Hewson, 2000, Mol. Med. Today 6,28–35; Allen et al., 2000, J. Immunol. 164, 4968–4978; Mahato, 1999, J. Drug Target 7, 249–268).

Various treatments with the invention compositions can also reduce transcription affected by SRCAP, e.g., by reducing SRCAP levels in the cell. For example, transcription can be reduced in a target cell by treating the cell with an antisense SRCAP polynucleotide or a ribozyme, as is known in the art. Additionally, treatment of the cell with an anti-SRCAP antibody would be expected to reduce transcription. The above treatments to reduce SRCAP levels would be useful for, e.g., reducing the effects of the various viruses that depend on CBP co-activation of viral transcription, and reducing the effects of hepatitis C virus on cell growth regulation (see Example 2).

The present invention also provides methods of treating a patient having a disease involving a function affected by SRCAP. The methods comprise treating a cell of the patient with an amount of a polypeptide, polynucleotide, or antibody composition of the invention sufficient to modulate transcription of the cell. As described supra in the context of the cell treatment methods, the treatment can be directed toward increasing the presence of SRCAP (e.g., by SRCAP or SRCAP fragment polypeptide or polynucleotide) or decreasing the presence of SRCAP (e.g., by antisense, ribozyme or antibody treatment). In particular embodiments, the function is insufficient transcription of a gene selected from the group consisting of a gene mediated by CBP co-activation, a DEAD box RNA dependent helicase (see Example 3), adenoviral DBP protein, β-actin, and a nuclear receptor. An example of a nuclear receptor is the glucocorticoid receptor (GR). In these embodiments, the cell is treated with a SRCAP polypeptide or SRCAP polynucleotide, or fragments thereof. In other embodiments, the function is undesired effects caused by HCV NS5A, HTLV-1 TAX protein, HIV-1 Tat protein, adenovirus EIA protein, Epstein-Barr virus zta protein, cytomegalovirus IE1/2 enhancer, hepatitis B virus (HBV) pX protein. As previously discussed, when reduction of transcription is desired, the cell may be treated with SRCAP antisense or ribozyme preparations, or with anti-SRCAP antibodies.

In additional embodiments, the present invention is directed to a method of treating a patient having a disease involving insufficient activity of a SRCAP protein. The method comprises administering a SRCAP protein or derivative or fragment thereof to the patient or administering a SRCAP polynucleotide or derivative or fragment thereof to the patient. In preferred aspects, the disease causes insufficient transcription of a gene selected from the group consisting of a gene mediated by CBP co-activation, a DEAD box RNA dependent helicase, adenoviral DBP protein, β-actin, and a nuclear receptor.

The present invention is also directed to compositions useful for studying the effects of SRCAP. These compositions comprise transgenic cells or non-human animals that express a recombinant SRCAP gene or fragment. The SRCAP gene or fragment could encode a SRCAP having substantially wild-type SRCAP activity, e.g., to study the effect of expression of increased amount of SRCAP. Alternatively, the SRCAP gene or fragment could encode a mutant nonfunctional SRCAP or a SRCAP fragment encoding only one or a few of the SRCAP activities (e.g., only the CBP co-activating portion), or could comprise an antisense or ribozyme inhibitor. The SRCAP gene or fragment could also be part of a chimera that has functions other than those of SRCAP.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example describes the identification and initial characterization of SRCAP.
Experimental procedures
Plasmids-To generate the plasmids $pGal-CBP_{227-410}$, $pGal-CBP_{280-460}$ and $pGal-CBP_{227-460}$, PCR was used to generate a cDNA fragment encoding CBP amino acids 227–460, 280–460, and 227–410 which contain a 5' XbaI and 3' BamHI sites. These were subcloned into the plasmid pRSV Gal$_{1-147}$ (Swope et al., 1996, *J. Biol. Chem.* 271, 28138–28145) digested with XbaI and BamHI. To generate the plasmid pVP16, PCR was used to generate a cDNA fragment which encoded a Methionine followed by amino acids 412 to 491 of VP16 (Dalrymple et al., 1985, *Nucl. Acid. Res.* 13, 7865–7879) and which contained a 5' XbaI site and a 3' EcoRI site. This was subdloned into the plasmid pcDNA 3.1 (Invitrogen) digested with XbaI and EcoRI. The plasmid pVP16-clone 11 was generated by subdloning the clone 11 cDNA insert obtained by EcoRI and BamHI digestion of the pGAD clone 11, into EcoRI and BamHI digested pVP16. The pAS1 CBP$_{227-460}$, plasmid was made using PCR to generate a cDNA fragment encoding amino acids 227–460 of CBP which contained EcoRI restriction sites at the ends. This was subcloned into the EcoRI site of the plasmid, pAS1. The plasmid pAS1 and the HeLa pGAD library were a gift of Paul MacDonald, St Louis University, St. Louis Mo. The pGal-VP16 chimera was a gift of R. Maurer, Oregon Health Sciences University, Portland, Oreg. The pGal SRCAP$_{1275-2971}$ plasmid was generated by subcloning the cDNA insert encoding SRCAP amino acids 1275–2971 obtained by NheI and BamHI digestion of the plasmid SRCAP$_{1275-2971}$ (described below) into pRSV Gal$_{1-147}$ digested with XbaI and BamHI.

Library Screen—*S. cerevisiae* reporter host strain HF7c was co-transfected with the plasmid pASI CBP$_{227-460}$ and the pGAD-HeLa library using a yeast transfection kit (Clonetech) and grown as described in Fields, S., 1993 (Methods: A companion to Meth. Enzymol. 5, 116–124) in the presence of 10 mM 3-amino-1,2,4-triazole. The plasmid corresponding to clone 11 was isolated and sequenced by the dideoxy sequencing method. The cDNA corresponding to the AB0002307 sequence was generated by PCR. Briefly, complimentary PCR primers located at the beginning of the AB0002307 sequence and spaced about 1 kb apart were used to screen a human SKN plasmid library (Gift S. Amara, Vollum Institute, Portland, Oreg.). These primers were designed to introduce restriction enzyme sites that allow assembly of the full length AB0002307 cDNA without introducing changes in the amino sequences. The 5'-most primer also encoded an initiator methionine and a consensus Kozak sequence. Following restriction digestion, the cDNA fragments were subcloned into the plasmid pcDNA 3.1 and named SRCAP$_{1275-2971}$. The clone 11 cDNA was used to screen a cDNA plasmid library by homology. Using this approach a series of overlapping cDNAs were obtained that extended the SRCAP coding sequences to 9144 bp. The sequences of all the clones were confirmed on both strands using an ABI automated DNA sequencer and the composite sequence has been deposited in the GenBank (accession NM 006662).

Transfections—HeLa cells were maintained in Dulbecco's modified Eagle medium (DMEM) supplemented with 10% fetal bovine serum (FBS), 100 mg/ml penicillin and 100 mg/ml streptomycin and were seeded at 1×10$^5$ cells per 3.5 cm dish 18 hours prior to transfection. Each transfection utilized 200–300 ng of the pGAL-CAT reporter (pGAIL4/E1b TATA) plasmid (Swope et al., supra) and the indicated plasmids. The Lipofectamine transfection method was used according to the manufacturer's directions (Gibco BRL). Cells were harvested 48 hours after transfection and assayed for CAT activity using the phase-extraction method (Swope et al., supra). Results were normalized to protein levels as determined by Bradford assay.

Immunoprecipitation—For the labeling studies, A549 or 293 cells were incubated for one hour with methioninelcysteine-deficient DMEM, 10% FBS dialyzed against PBS (phosphate buffered saline), and penicillin/streptomycin, then metabolically labeled overnight in 1 ml deficient DMEM and 0.25 mCi $^{35}$[S]-methionine/cysteine (EPRESS Label-NEN), Labeled cells were lysed in 1 ml p300 lysis buffer (Yaciuk et al., 1991, *Mol. Cell. Biol* 11, 5389–5397) and the supernatant incubated with protein A sepharose beads and a monoclonal antibody raised to the C-terminal end of AB0002307 (SRCAP amino acids 2733–2971). Immune complexes were washed extensively, then boiled two minutes in 20 µl 2×Laemmli buffer and analyzed by SDS-PAGE. Radiolabeled proteins were visualized using a PhosphorImager. For the ATPase activity studies, nuclei of A459 cells were prepared by the method of Digram et al. (1983, *Nucleic Acids Res.* 11, 1475–1489). The nuclei were incubated in p300 lysis buffer, centrifuged and SRCAP immunoprecipitated by addition of anti-AB0002307 monoclonal antibody and protein A beads to the supernatant. In parallel experiments, control "mock" immunoprecipitations were performed by addition of protein A sepharose beads alone.

ATPase assay- Protein A beads containing the SRCAP protein were further washed with 1.0 M NaCl, 10 mM Na$_2$PO$_4$, pH 8, 0.5% Triton X100 to remove non-specifically bound proteins and followed by a final wash in ATPase buffer consisting of 20 mM Tris, pH 7.9, 0.1% Tween-20, 30 mM NaCl, 5 mM MgCl$_2$, 0.5 mM DTT and 0.5 mg/ml BSA. The Km for ATP hydrolysis was determined as described by Cote et al. (20). Briefly, 2–3 µl of SRCAP-protein A beads were incubated in 20 µl of ATPase buffer containing various amounts of cold A?T (10–300 µl) and 1 µCi P-γ-ATP (3000 Ci/mmole). Following a 20 minute incubation at 30° C. the unhydrolyzed ATP was removed by the addition of 150 µl of 10 mM phosphoric acid containing 5% activated charcoal (Sigma). The mixture was vortexed, centrifuged to pellet the charcoal and the supernatant removed to a new tube. An additional 150 µl of the phosphoric acid/charcoal solution was added and the mixture vortexed, centifuged and the $^{32}$Pi in the supernatant counted. Specific Pi released was determined by subtracting the non-specific counts obtained from the mock immunoprecipitated protein A beads. To ensure the ATPase assay was within the linear range, various amounts of SRCAP-protein A beads (1–6 µl) were assayed as described in 100 µM cold ATP and 1 µCi $^{32}$P-γ-ATP.

Results

Figure 3:
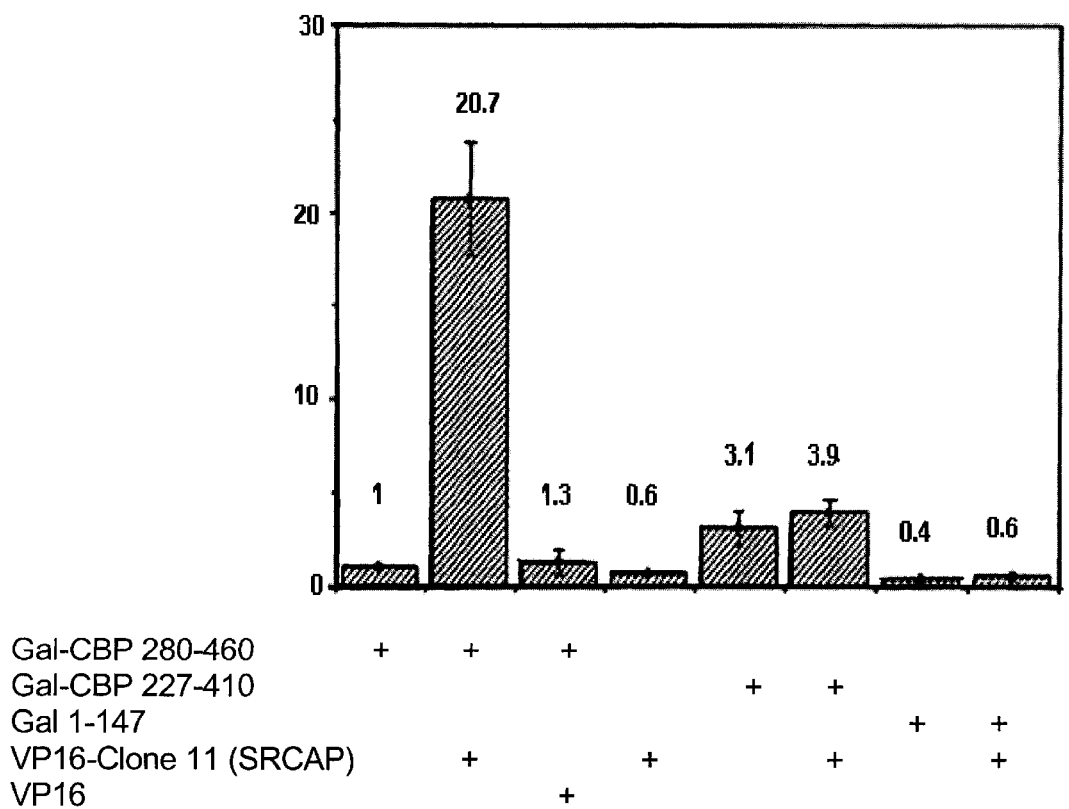
FIG. 3 is a graph of measurements of the interaction of CBP with SRCAP in HeLa cells. The interaction of CBP and SRCAP cDNA (encoded by clone 11) was assessed using a mammalian two hybrid assay. HeLa cells were transfected with 300 ng of reporter gene pGAL-CAT and 600 ng of either pGal-CBP$_{280-460}$, pGal-CBP$_{227-410}$, or pGal$_{1-147}$ and 600 ng of either pVP16, pVP16-clone 11, or pcDNA 3.1. The relative CAT enzymatic activity was determined by dividing CAT enzymatic activity of each sample by the transcriptional activity induced by the Gal-CBP$_{280-460}$ chimera. Values are the means and S.E. from three separate experiments in which each point was performed in triplicate.

A yeast two hybrid screen was employed to identify cDNA clones encoding proteins that contact CBP amino acids 227–460. In the initial screen an excess of fifty clones were obtained and these were further analyzed by DNA sequencing. This analysis indicated that clone 11 shared sequence identity with an uncharacterized cDNA reported in GenBank (AB0002307) (FIG. 2A). A BLAST search with the AB0002307 sequences indicated it shared homology with two of the seven domains (V and VI) found within the ATPase domain conserved in proteins of the Snf2 gene family (FIG. 2A). Because of this homology we decided to test whether the protein encoded by clone 11 interacted with CBP in mammalian cells. For this assay, we constructed a plasmid encoding a VP16-clone 11 chimera and co-transfected it with the plasmid encoding the Gal-CBP 227 460 chimera. In these studies, the VP16-clone 11 chimera consistently increased about 1.5-fold the ability of the Gal-CBP$_{227-460}$ chimera to activate transcription of the reporter gene pGal-CAT (data not shown). We reasoned that the small 1.5 fold activation of transcription observed occurred because the Gal-CBP$_{227-460}$ chimera is a very strong transcriptional activator. To circumvent this problem, we tested the interaction of the VP 16-clone 11 chimera with the Gal-CBP$_{227}$410 and Gal-CBPP$_{280-460}$ chimeras that contain small deletions that reduce but do not eliminate their ability to activate transcription. As shown in FIG. 3, co-transfection of the plasmids encoding the VP 1 6-clone 11 chimera with the plasmid encoding Gal-CBP$_{280-460}$ activates transcription about 20-fold compared to that seen with the Gal-CBP$_{280-460}$ chimera alone. Co-transfection of the plasmid encoding Gal-CBP$_{280-460}$ with the plasmid encoding only the VP16 activation domain did not activate transcription, indicating that contact of the VP 16-clone chimera with CBP is mediated by the clone 11 portion. The VP 16-clone 11 chimera failed to activate transcription of the more active Gal-CBP$_{227-410}$ chimera or Gal$_{1-147}$ indicating that transcriptional activation is not due to a non-specific effect.

Studies were also conducted to delineate the borders of the minimal SRCAP binding domain within CBP. For these studies, a mammalian cell assay was developed by determining whether a portion of SRCAP (amino acids 1380–1699), which was identified by the yeast hybrid screening to interact with CBP (see Example 1) also contacted CBP in mammalian cells (FIG. 3). In these studies, HeLa cells were co-transfected with a plasmid encoding a VP16-SRCAP$_{1380-1699}$ chimera and plasmids encoding either a Gal-CBP$_{280-460}$ chimera or a Gal-CBP$_{227-410}$ chimera along with a reporter gene (Gal-CAT) containing the binding site for Gal4. If interaction between the SRCAP moiety of the VP16-SRCAP$_{1380-1699}$ chimera occurred with the CBP portion of either of these Gal-CBP chimeras, we would expect to see an increase in transcriptional activity. As shown in FIG. 3, the VP16-SRCAP$_{1380-1699}$ chimera increased the transcription mediated by the Gal-CBP$_{280-460}$ chimera about 20-fold. In contrast, the VP16-SRCAP$_{1380-1699}$ chimera failed to activate transcription of the Gal-CBP$_{227-410}$ chimera indicating that the SRCAP binding domain of CBP resides within amino acids 280–460.

Figure 4:
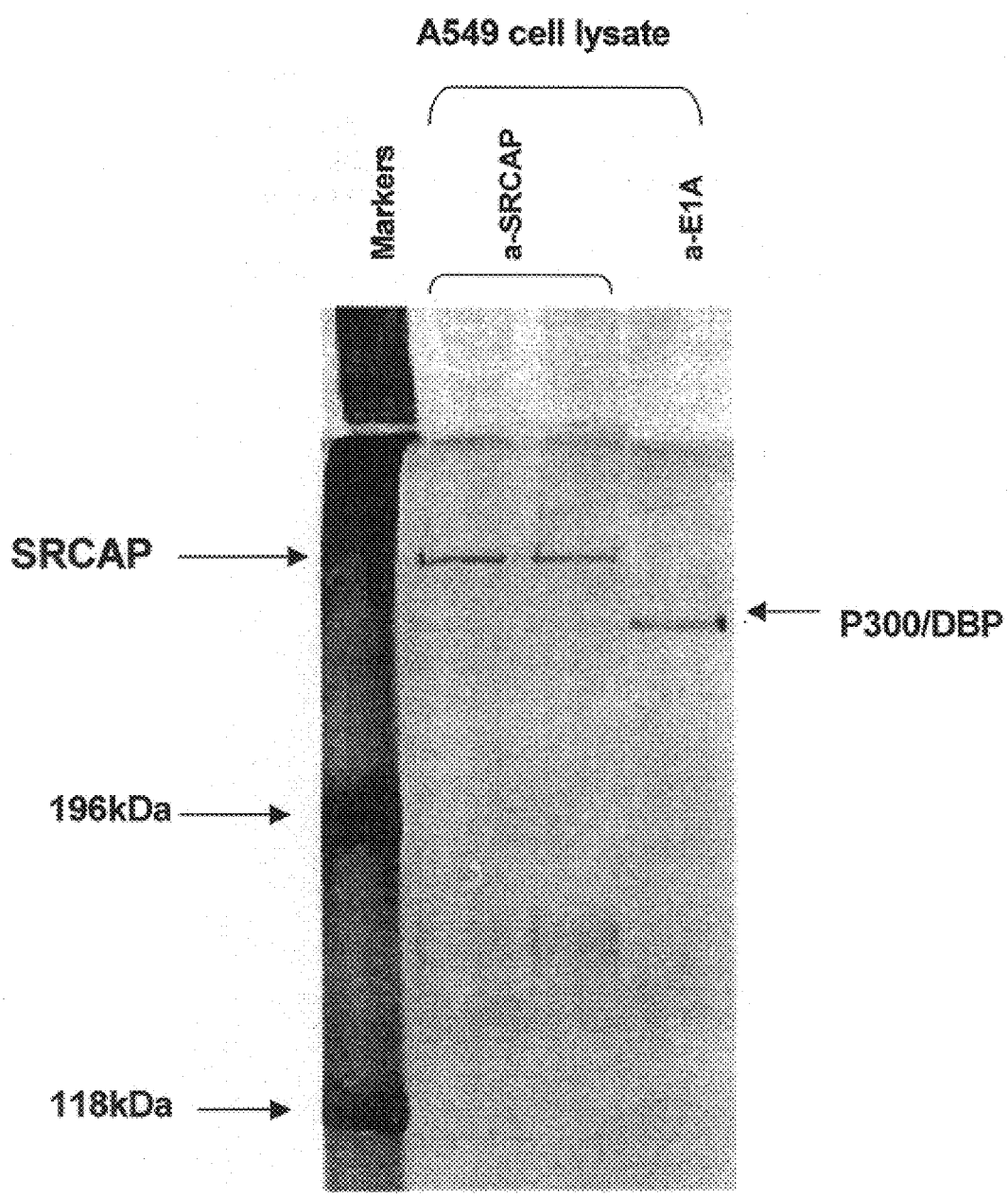
FIG. 4 is an autoradiograph demonstrating that anti-SRCAP antibodies immunoprecipitate a protein larger than CBP. Monoclonal antibodies raised against either the C-terminal end of SRCAP (amino acids 2733–2971) or against E1A (M73 antibody, reference 18) were used to precipitate radiolabeled proteins from extracts made from 293 cells which were grown in the presence of $^{35}$[S]-methionine/cysteine. Precipitated proteins were analyzed by SDS-PAGE and visualized using a PhosphorImager. The antibody against E1A has been previously shown to co-precipitate CBP/p300 with E1A. The position of CBP/p300 is indicated by the arrow on the right. The antibody against SRCAP precipitates a protein that migrates slower than CBP/p300. The position of the SRCAP protein is indicated by the arrow on the left.

Based on the above results we decided to clone the remainder of the AB0002307 cDNA. Using a combination of approaches (PCR and plasmid library screening), a 9.1 kb cDNA was obtained (FIG. 2A). This included the 5 kb of the AB0002307 cDNA and an additional 4.1 kb of new sequence at the 5' end of the molecule. Within the AB0002307 sequence, we found several differences with the reported sequences including an additional 111 base pair insertion at nucleotide 4128. The 9.1 kb composite sequence contains a continuous open reading frame. It, however, does not contain a termination codon (in the coding frame) raising uncertainty as to whether the cDNA clones obtained encode the full length protein. The presumptive initiator ATG is positioned at nucleotide 217 and is the first ATG in the open reading that occurs in the context of a consensus Kozak sequence (Kozak, 1989, *J. Cell Biol*. 108, 229–241). Using this ATG as a translational start site a protein of 2971 amino acids with a predicted molecular weight of 315 Kd is obtained. This size is consistent with immunoprecipitation studies in which anti-AB0002307 antibodies detect a protein that migrates slower in SDS-PAGE gels than CBP (predicted molecular weight of 265 Kd) (FIG. 4).

A search of the NCBI database with the AB0002307 sequence indicated that it contains a complete ATPase domain that consists of seven highly conserved regions (I, Ia–VI) which are dispersed over the length of the protein. Based on the homology to Snf2 family members and, as described below, on the ability to enhance CBP-mediated transcription, we named this protein SRCAP Snf2 Related CBP Activator Protein). A comparison of the amino acid sequence of the SRCAP ATPase domain to the amino acid sequence of the ATPase domains found in other members of the Snf2 family is shown in FIG. 2B.

Figure 5A:
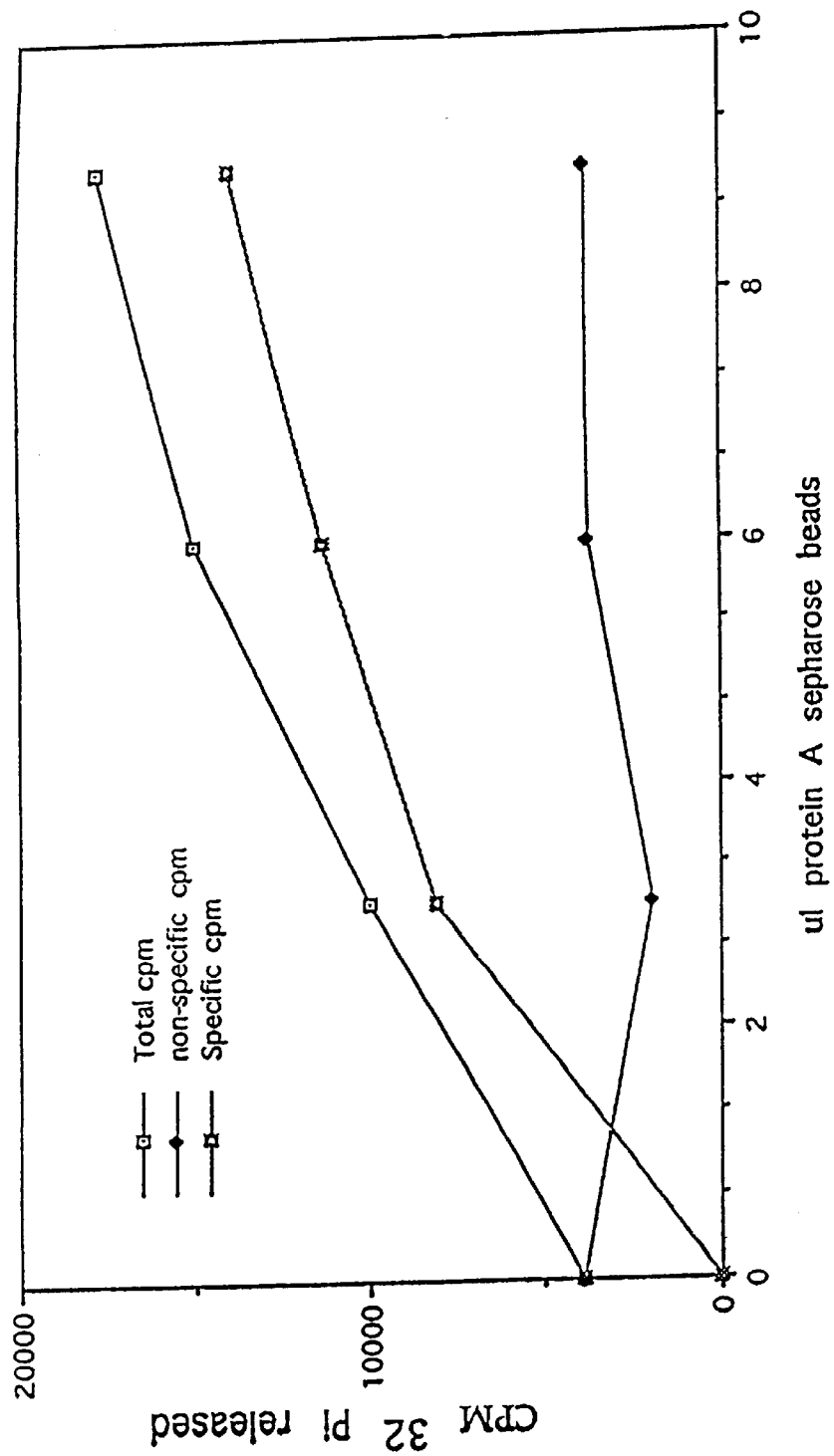
In FIG. 5A, increasing amounts of immunoprecipitated SRCAP (bound to protein sepharose A beads) or protein A beads (used in mock immunoprecipitation in the absence of antibody) were incubated with ATPase buffer containing 100 μM cold ATP and 1 μCi $^{32}$P-γ-ATP and the amount of Pi released due to hydrolysis of ATP measured. Shown are three curves representing the total Pi released by the SRCAP-proteinA sepharose beads (upper), the non-specific Pi released by the mock immunopreciptated protein A beads (lower) and the specific counts derived by subtracting the non-specific from the total Pi released (middle).
Figure 5B:
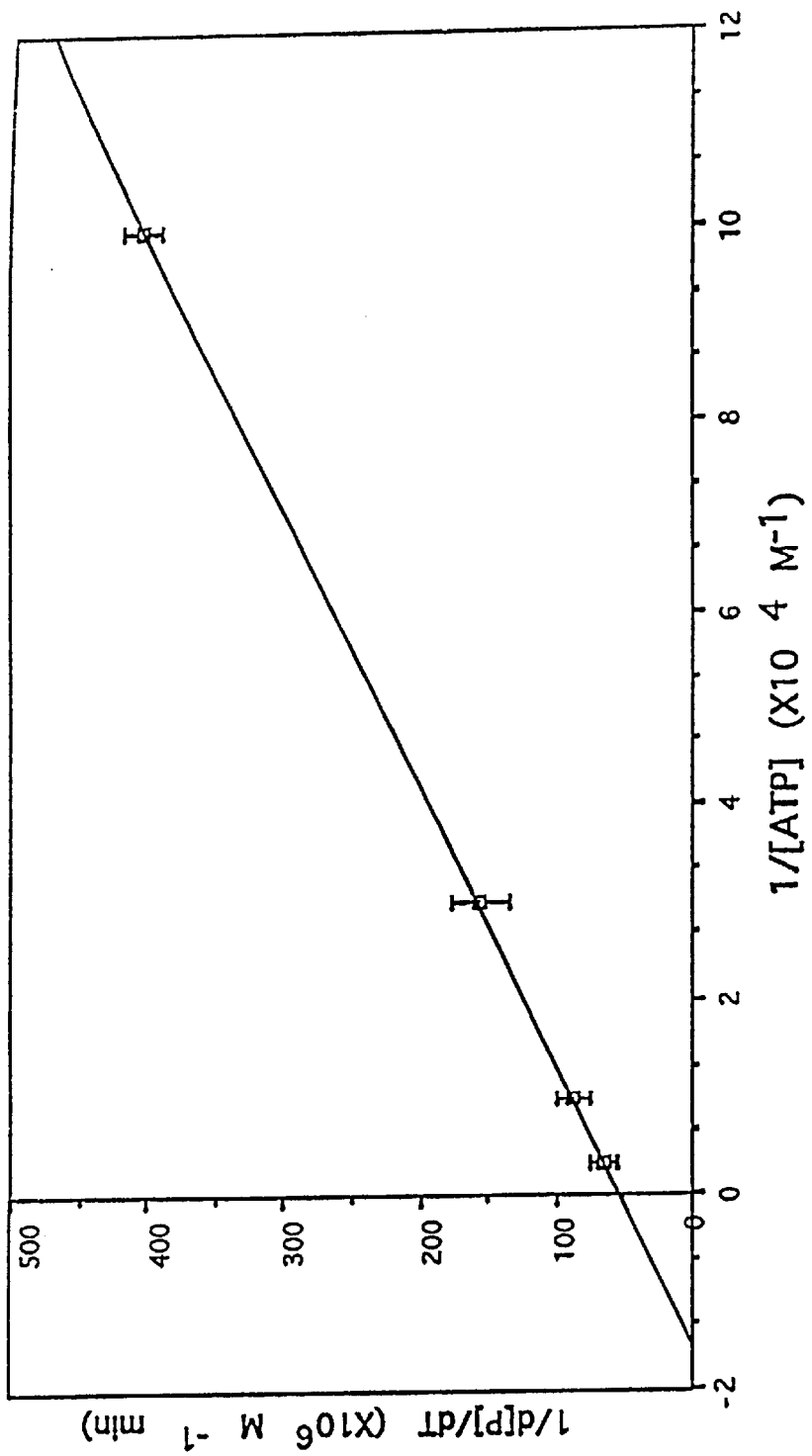
In FIG. 5B, the Km for hydrolysis of ATP by SRCAP was measured by determining hydrolysis of ATP by 2 μl of the SRCAP-protein A sepahose beads incubated with 1 μCi $^{32}$P-γ-ATP and either 10 μM, 30 μM, 100 μM, or 300 μM cold ATP. A plot of 1/[ATP] versus 1/d[Pi]/dT (1/ the change in Pi concentration over time) obtained at each concentration is shown. Values are the means and S.E. from three separate experiments and gives SRCAP a Km value for hydrolysis of ATP of 66 μM.

To test whether SRCAP, like other members of the Snf2 family, functions as an ATPase, we immunoprecipated SRCAP protein from nuclear extracts of A549 cells using the anti-AB0002307 monoclonal antibody and protein A sepharose beads. Shown in FIG. 5A incubation of the SRCAP-protein A beads in ATPase buffer containing 100 pM cold ATP and 1 $\mu$Ci $^{32}$P-$\gamma$-ATP resulted in the release of $^{32}$Pi indicating the hydrolysis of ATP was occurring. The specific ATPase activity due to SRCAP was determined by subtracting out the non-specific ATPase activity which bound to protein A in the absence of the anti-AB0002307 antibody. As shown, a linear increase in the specific ATPase activity was observed with increasing amounts of SRCAP-protein A beads. To determine the Km for the hydrolysis of ATP by SRCAP, 2 $\mu$l of SRCAP-protein A beads were incubated with 1 $\mu$Ci $^{32}$P-$\gamma$-ATP and either 10 $\mu$M, 30 M, 100 $\mu$M or 300 $\mu$M cold ATP. A plot of 1/d[Pi]/dT versus 1/[ATP] for three experiment is shown in FIG. 4B and indicated SRCAP has a Km for hydrolysis of ATP of 66 $\mu$M.

Figure 6:
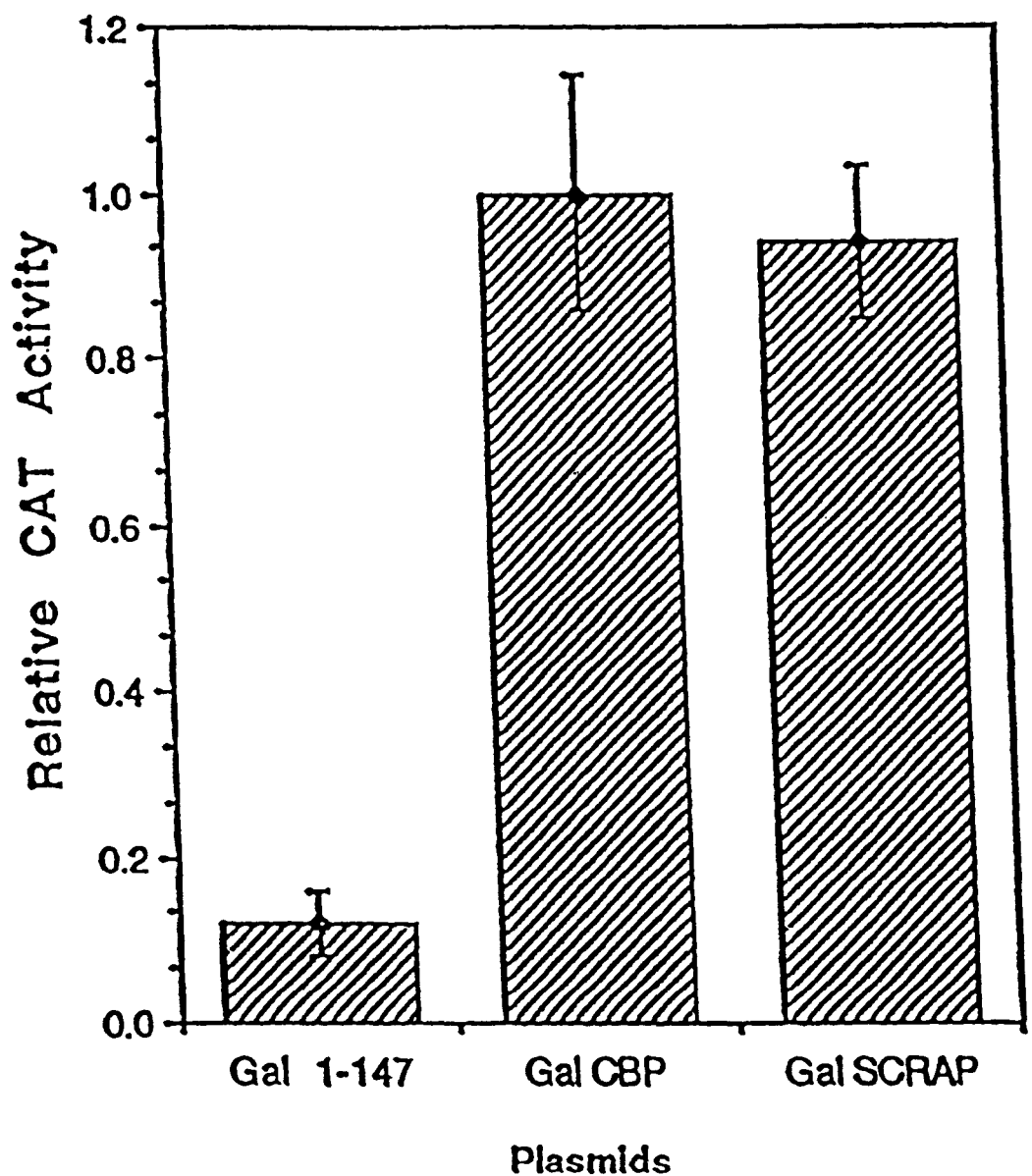
FIG. 6 is a graph of measurements of the activation of transcription by a Gal-SRCAP chimera. The ability of SRCAP to activate transcription was assessed by transient transfection assay. HeLa cells were transfected with 300 ng of the plasmid encoding the pGal-CAT reporter gene and equal molar amounts of either pGal CBP$_{1-2441}$ (700 ng), pGal SRCAP$_{1275-2971}$ (592 ng plus 108 ng pcDNA 3.1), or pGal$_{1-147}$ (323 ng plus 377 ng pcDNA 3.1). The relative CAT enzymatic activity was determined by dividing CAT enzymatic activity of each sample by the transcriptional activity induced by the Gal-CBP$_{1-2441}$ chimera. Values are the means and S.E. from three separate experiments in which each point was performed in triplicate.

Several members of the Snf2 gene family have been found to regulate transcription when tethered to a promoter by a heterologous DNA binding domain. This prompted us to ask whether SRCAP was a transcriptional activator. For these studies, we tested the ability of a plasmid encoding a Gal-SRCAP$_{1275-2971}$ chimera to activate transcription of the Gal-CAT reporter gene in HeLa cells. As shown in FIG. 6, this chimera activated transcription about 12-fold over the level of transcription induced by Gal$_{1-147}$, and to about the same level as that observed with the Gal-CBP$_{1-2441}$ chimera.

Figure 7:
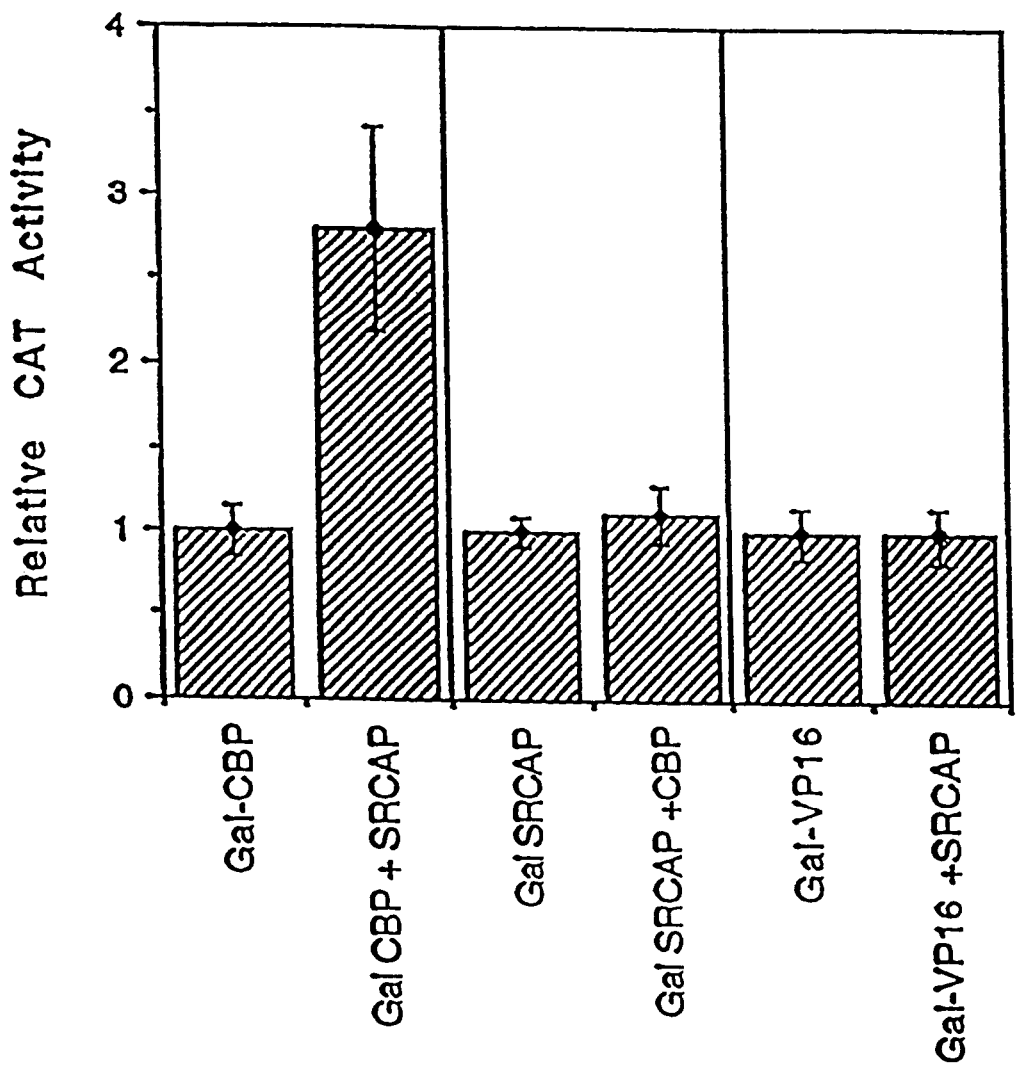
FIG. 7 is a graph that demonstrates that SRCAP enhances transcription mediated by CBP. The ability of SRCAP to activate transcription of a Gal CBP chimera was assessed by transient transfection. HeLa cells were transiently transfected with 300 ng of the reporter gene pGal-CAT in the following combinations of plasmids: pGal CBP$_{1-2441}$ (700 ng plus 592 ng of pcDNA 3.1), pGal CBP$_{1-2441}$ (700 ng) and SRCAP$_{1275-2971}$ (592 ng), pGal SRCAP$_{1275-2971}$ (592 ng plus 592 ng pcDNA 3.1), pGal SRCAP$_{1275-2971}$ (592 ng), and pCBP$_{1-244}$, (592 ng), pGal VP16 (50 ng plus 592 ng of pcDNA 3.1), or pGal VP16 (50 ng) and SRCAP$_{1275-2971}$ (592 ng). The relative CAT enzymatic activity was determined by dividing CAT enzymatic activity of each sample by the transcriptional activity induced by pGal CBP$_{1-2441}$ in the left panel, by the transcriptional activity induced by pGal SRCAP$_{1275-2971}$ in the middle panel, and by the transcriptional activity induced by pGal VP 16 in the right panel. Values are the means and S.E. from three separate experiments in which each point was performed in triplicate.

To test whether SRCAP influenced the ability of CBP to activate transcription, we co-transfected the plasmid encoding SRCAP amino acids 1275–2971 with the plasmid encoding Gal-CBP$_{1-2441}$. As shown in FIG. 7, SRCAP enhanced the ability of the Gal-CBP to activate transcription about 2.5 fold. This enhancement of transcription was specific since SRCAP did not enhance the ability of Gal-VP16 to activate transcription. Co-transfection of the plasmid encoding the CBP$_{1-2441}$ along with the plasmid encoding the Gal-SRCAP$_{1275-2971}$ chimera did not result in a further increase in transcription (data not shown). The inability of exogenously introduced CBP to activate SRCAP transcription activity suggests that CBP is either not limiting in HeLa cells or that SRCAP does not function to activate transcription by recruitment of CBP. Consistent with this latter hypothesis, we have found that a Gal-clone 11 chimera that encodes the CBP binding domain of SRCAP does not activate transcription in either HeLa or F-9 cells (data not shown).

Figure 8:
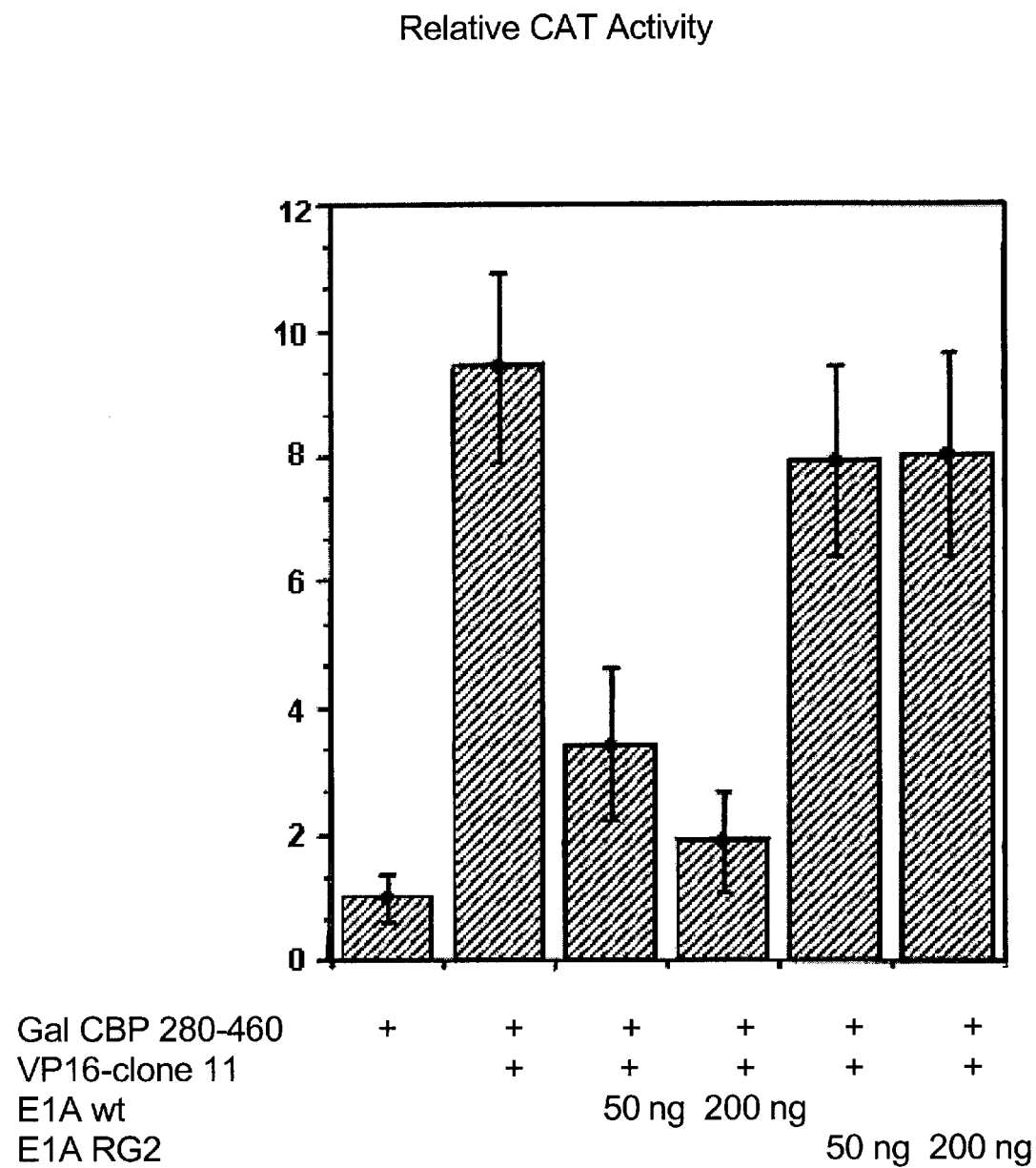
FIG. 8 is a graph that demonstrates that the adenoviral protein E1A disrupts interaction of CBP and SRCAP. The ability of E1A to disrupt CBP-SRCAP interaction was assessed by transient transfection. HeLa cells were transiently transfected with 300 ng of the reporter gene pGal-CAT, 600 ng of pGal CBP$_{280-460}$, 600 ng of pVP 16-clone 11 and either 50 or 200 ng of pE1A or pE1A RG2. Values are the means and S.E. from two separate experiments in which each point was performed in triplicate.

Recent studies indicate that the adenoviral protein E1A binds to the amino terminal end of CBP and inhibits the ability of a Gal-CBP$_{1-450}$ chimera to activate transcription prompted us to determine whether E1A inhibits binding of SRCAP to CBP (Kurokawa et al., 1998, *Science* 279, 700–702). As shown in FIG. 8, transfection of plasmids encoding wild type E1A decreased transcription stimulated by interaction of the Gal-CBP$_{280-460}$ with the VP16-clone 11 chimera. In contrast, co-transfection with a plasmid encoding an E1A mutant (RG2) which does not bind CBP did not disrupt SRCAP and CBP interaction.

Discussion

In this example, we disclose the cloning of SRCAP, a novel member of the Snf2 gene family. As previously discussed, the Snf2 domain, having ATPase activity, consists of seven highly conserved motifs interspersed with variable spacers of non-conserved sequences. The entire Snf2 domain is contained in about 400 amino acids in most Snf2 family members (Snf2, Iswi, Chd1, Rad16, and Mot-1) and is contained in about 670 amino acids in others (113 and Hip 116) (Zhang et al., 1997, Gene 202, 31–37). The Snf2 domain of SRCAP is unique in that the ATPase domain is dispersed in a much larger region of about 1465 amino acids (FIG. 2B). Despite the unique spacing between the conserved motifs, the conservation of residues within the ATPase domain is striking. Consistent with this homology we have found that SRCAP functions as an ATPase with a Km for ATP hydrolysis of 66 p which is similar to the reported Km for hydrolysis of ATP by yeast Snf2 of 45 μM (Cote et al., 1994, Science 265, 53–60). The ATPase activity of recombinant yeast Snf2 protein (purified from bacteria) has been reported to be stimulated five-fold by DNA (Laurent et al., 1993, Genes Dev. 7, 583–591). In contrast, the ATPase activity of SRCAP (purified from A549 cells) was not stimulated by DNA (data not shown). This result suggests that the regulation of the ATPase activity of SRCAP and yeast Snf2 may occur through distinct mechanisms. However, we cannot rule out the possibility that the lack of DNA dependence observed for the ATPase activity of SRCAP is due to differences in the protein purification protocols used e.g. which may allow DNA to co-purify with SRCAP but not yeast Snf2.

The ATPase domain has been shown to be critical for the function of several Snf2 family members. The yeast Snf2 protein is the prototype of this family. It functions as part of a multiple subunit SWI/SNF complex that appears to alleviate the repression of transcription of some promoters induced by chromatin through a process termed chromatin remodeling (reviewed in Peterson et al., 1995, TIBS 20, 143–147). Although the specific mechanisms for chromatin remodeling are not completely known, it allows the binding of transcription factors to sites previously inaccessible due to the presence of nucleosomes. Mutant yeast Snf2 molecules in which the ATPase function has been deleted neither function in chromatin remodeling assays or are able to activate transcription (Laurent et al., supra). ATPase activity is also required for transcriptional repression mediated by the Snf2 family member MOT-1 (Auble et al., 1997, Mol. Cell. Biol. 17, 4842–4841) which utilizes ATP to dissociate TBP from DNA. However, as discussed below, the ATPase activity of SRCAP is not needed for SRCAP mediated transcriptional activation. While this result differs from that obtained for the yeast Snf2, an analogous finding has been reported for the human Snf2 protein (hSnf2α)(Muchardt et al., 1993, EMBO J. 12, 4279–4290). Similar to our studies with SRCAP, when human Snf2α is tethered to DNA by a heterologous DNA binding domain, the ATPase function is not required for activation of transcription. However, the ATPase function is essential for hSnf2α potentiation of glucocorticoid receptor mediated transcription (Id.). These findings suggest that activation of transcription by human Snf2 (and perhaps SRCAP) occurs through several distinct mechanisms, one requiring the ATPase function and one which does not.

It is believed that the highly charged C-terminal end of SRCAP contributes to the ability of SRCAP to activate transcription since, in the case of hSnf2α, deletion of the analogous highly charged domain results in loss of transcriptional activity (Id.).

Examination of the primary structure of the SRCAP indicates that in addition to binding CBP, it also apparently binds to DNA. Shown in FIG. 2A, the C-terminal domain contains four copies of the motif KR(R/K)RGRP(P/R) of which multiple copies are also found in DNA binding proteins (chromosomal protein D1 and HMG-1), where it is thought to mediate the binding of these proteins to A-T rich regions by contacts in the minor groove of DNA (Ashley et al., 1989, J. Biol. Chem. 264, 8394–8401; Churchill et al, 1991, TIBS 16, 92–97). A similar motif is found in the C-terminal end of human homologs of yeast Snf2 (hSnf2α and β) and within the DNA binding domain of the Snf2 gene family protein CHD1 (Chiba et al., 1994, Nucleic Acids Res. 22, 1815–1820; Stokes et al., 1995, Mol. Cell. Biol. 15, 2745–2753).

The adenoviral protein E1A exerts several biological activities including transformation of cells and activation or repression of cellular and viral genes (reviewed in Moran, 1994, Semin. Virol. 5, 237–240). E1A blocks the ability of CBP to function as a co-activator for a number of transcription factors and binds to three distinct sites within CBP: Amino acids 1–460, amino acids 1805–1891, and amino acids 2058–2163 (Kurokawa et al., 1998, Science 279, 700–702; Yang et al., 1996, Nature 382, 319–324; Lundblad et al., 1995, Nature 374, 85–88; Arany et al., 1995, Nature 374, 81–85). Understanding how association of E1A with CBP alters the ability of CBP to finction as a co-activator has come from studies that demonstrate that E1A binding competitively excludes binding of several proteins shown to be critical for CBP co-activator function. Binding of E1A to CBP amino acids 1805–1891 prevents binding of the histone acetyltransferase P/CAF while E1A binding to CBP amino acids 2058–2163 prevents binding of the co-activator P/CIP (Kurisawa et al, supra; Yang et al., supra). Although P/CAF also binds to amino acids 1–460 of CBP, competition between PICAS and E1A binding has not been demonstrated. In our studies, we have found that E1A binding to amino acids 280–460 of CBP excludes the binding of SRCAP to CBP suggesting that this represents an additional method by which E1A represses the co-activator fiction of CBP.

The primary structure of SRCAP indicates that it belongs to the Snf2 family of proteins, which finction to modify protein-DNA interactions suggesting that SRCAP plays a similar role. Consistent with this notion our results indicate that SRCAP interacts with CBP and influences its ability to activate transcription. Recent studies have indicated that different promoters that utilize CBP to activate transcription have different requirements for co-activators. For example, both P/CAF and P/CIP have been found to be required for activation of a CRE-reporter gene while P/CIP but not P/CAF is required for transcription of a GAS-reporter gene (Korzue et al., 19989, Science 279, 703–706). It, therefore, seems likely that SRCAP may function to enhance CBP-mediated transcription at some but not all promoters.

EXAMPLE 2

This example describes studies that reveal the interaction of SRCAP with the NS5A protein of hepatitis C virus (HCV). Hepatitis C virus (HCV) is an important cause of morbidity and mortality worldwide, causing a spectrum of liver disease ranging from an asymptomatic carrier state to end-stage liver disease (DiBisceglie, 1997, Hepatology 26,34S–38S; Purcell, R. H., 1994. Proc. Natl. Acad. Sci USA 91, 2401–2406). The HCV genome encodes a single polyprotein precursor that is cleaved by both host and viral proteases to generate structural and non-structural proteins. The non-structural protein 5A (NS5A) is generated as a mature protein by the action of NS3 protease in conjunction with NS4A (Grakoui et al., 1993, J. Virol. 67, 1385–1395; Tanji et al., 1995, J. Virol. 69, 3980–3986). NS5A is localized in the nuclear periplasmic membrane (Tanji et al., supra) and exists as phosphoproteins (p56 and p58), with the degree of phosphorylation accounting for the difference in size (Ide et al., 1997, *Gene* 201, 151–158; Kaneko et al., 1994, *Biochem. Biophys. Res. Comun.* 205,320–326; Reed et al., 1997, *J. Virol.* 71,7187–7197). Phosphorylation status of NS5A differs amongst HCV genotypes (Hirota et al., 1999, *Virology* 257, 130–137). NS5A is phosphorylated by a cellular serine/threonine kinase, and Ser$^{2321}$ represents a major phosphorylation site (Reed et al., 1999, *J. Biol. Chem.* 274, 28011–28018). However, this phosphorylation site is dispensable for interactions with NS4A and PKR. Sequence comparison of the regions surrounding the phosphorylation sites indicates an extremely high level of conservation between different strains of the HCV but the biological significance of phosphorylation is still undefined.

Recent studies suggest that HCV NS5A protein transcriptionally modulates cellular genes, promotes cell growth (Ghosh et al., 1999, *J. Gen. Virol.* 80, 1179–1183; Gale et al., 1999, *J. Virol.* 73, 6506–6516) and inhibits TNF-A mediated apoptotic cell death (A. K. Ghosh and R. B. Ray, unpublished observations). There is also evidence that two-thirds of the NS5A protein from the C-terminal fused with Gal4-DNA binding domain functions as a potent transcriptional activator (Tanimoto et al., 1997, *Biochem. Biophys. Res. Commun.* 236, 360–364; Kato et al., 1997, *J. Virol.* 71, 8856–8859). Viral proteins may influence cellular genes, which in turn may be involved in the regulation of oncogenes or tumor suppressor genes. Inactivation of these genes may be a mechanism for the disruption of normal cell growth. Host factors are important components for the modulation of virus replication. Viruses also produce proteins that may interact with host factors for viral persistence by disrupting normal cell cycle.

To further understand the functional role of HCV NS5A, the interaction of NS5A with cellular protein(s) by yeast two-hybrid screening was examined. Results from this study provided important information regarding the association of NS5A protein with SRCAP.

Experimental Procedures

Yeast two-hybrid screening. The entire cDNA coding region of HCV NS5A (genotype la, H strain) was fused in frame with the Gal4 DNA-binding domain into the pGBT9 plasmid vector (Clontech) at the EcoRI/SalI restriction sites (pGBT9-5A) and transformed into *Saccharomyces cerevisiae* yeast strain HF7c. The pGBT9-5A positive yeast colonies were grown in appropriate liquid medium lacking tryptophan and were subsequently transformed with library plasmids fused to the GAL4 activation domain, constructed in pGAD plasmid vector (Clontech) for screening of cellular partners. Colonies were selected on agar plates lacking histidine, tryptophan, and leucine over a 7-day period. Positive yeast transformants were picked up and replated for β-galactosidase assay by colony-lift filter procedure. A positive interaction was determined by the appearance of blue colonies. The β-gal positive colonies were grown on a selective medium for plasmid isolation. Isolated plasmids were transformed into *E. coli* KC8 strain and selected for the activation domain plasmids on M9-leu⁻ agar plates. The potential NS5A-interacting cDNA inserts were retransformed into the yeast strain HF7c bearing the pGBT9-5A fusion gene, and were grown on an appropriate selective medium for β-gal assay. Positive interacting cDNA clones were analyzed by nucleotide sequencing using an automated sequencer (ABI). Using Blast analysis, nucleotide and predicted amino acid sequences were compared with known protein sequences in GenBank.

Mammalian two-hybrid analysis. A mammalian expression plasmid encoding VP16, a hybrid polypeptide containing the transactivation domain of herpesvirus VP16 (Yu et al., 1998, *J. Biol. Chem.* 273, 25388–25592), was fused to NS5A (VP16-5A). Gal-SRCAP expression plasmid DNA (Johnston et al., supra) was used in this study. HepG2 and NIH3T3 cells were cotransfected with 1 μg of Gal4 responsive reporter gene (G5E1b-CAT), 2 μg of VP 16-5A, and Gal-SRCAP or Gal-ΔSRCAP effector plasmids. CAT assay was performed as described in Ghosh et al., supra. In all the transfection experiments, the β-galactosidase gene was included to normalize the transfection efficiency.

In vitro pull-down experiment The NS5A genomic region was cloned in frame with histidine-tag (His-NS5A) into proExHTA plasmid vector (Life Technology, Inc), and expressed in *E. coli* BL21 cells. Bacterial extracts were immobilized onto Ni-beads and incubated with in vitro translated $^{35}$S-methionine labeled CNW-SRCAP. Beads were washed and proteins were analyzed by SDS-polyacrylamide gel electrophoresis, followed by autoradiography (Ghosh et al., 1999, *Biochem. Biophys. Res. Commun.* 260, 405–409). His-MBP-1 (an unrelated protein) was used similarly as a negative control.

Coimmunoprecipitation. HepG2 cells grown in 35 mm plates were transfected with 1 μg of the CMV-NS5A or pcDNA3 control plasmid using lipofectamine (Life Technologies, Inc). Cell lysates were prepared after 48 h of transfection in 0.3 ml of low stringency lysis buffer (150 mm NaCl, 10 mM Hepes, pH 7.6, 0.1% Nonidet P-40, 5 mM EDTA) containing protease inhibitors (2 μg/ml aprotinin, 2 μg/ml leupeptin, 1 μg/ml pepstatin, and 1 mM phenylmethylsulfonylfluoride). Each of the cell lysates were incubated with monoclonal antibody to SRCAP and immobilized on staphylococcal ProteinA-Sepharose CL-4B beads (Pharmacia). Immunoprecipitates were separated by SDS-PAGE, followed by Western blot analysis using NS5A or SRCAP specific antibody.

Immunofluorescence study. HepG2 cells were grown on glass cover slips in DMEM-10% FBS. Cells grown overnight were transfected with CMV-NS5A using lipofectamine for immunofluorescence and colocalization studies using a method similar to that described in Taylor et al., 1999, *Science* 285, 107–110. Cells were washed after 48 h of transfection and fixed with 3.7% formaldehyde in PBS for 30 min. After fixing, cells were washed twice with PBS and permeabilized with 0.2% Triton X-100 in PBS for 5 min. Cells were incubated with a murine monoclonal antibody to SRCAP, anti-NS5A rabbit polyclonal antibody or both the antibodies for 1 h at room temperature. Cells were washed and incubated with fluorochrome-conjugated secondary antibodies for 30 min at room temperature. Finally, washed cells were mounted for confocal microscopy using Bio-Rad 1024 Confocal Microscope. Fluorescence images were superimposed digitally to allow fine comparison. Colocalization of green (FITC) and red (TRITC) signals in a single pixel produces yellow color while separated signals remain green or red.

Quantitative RT-PCR. Cytoplasmic RNA was isolated from NIH3T3 cells transfected with various plasmid DNAs, stable NIH3T3neo and NIH3T3NS5A cells (Gale et al., 1999, *J. Virol.* 73, 6506–6516) using PUREscript kit (Gentra System). RNA (2 μg) was used for reverse transcription-PCR (RT-PCR) as described previously (Ray et al., 1995, *Cancer Res.* 55, 3747–3751; Ghosh et al., 1999, *Gene* 235, 85–91). RT-PCR reaction was performed using specific primers for p21 cDNA (forward primer: 5'TGTCCGTCAGAACCCATGCG-3' [SEQ ID NO:12];

reverse primer: 5'AGGGCTTCCTCTGGAGA3' [SEQ ID NO:13]), luciferase cDNA (forward primer: 5'TTCGCAGCCTACCGTAGTGT-3' [SEQ ID NO:14]; reverse primer: 5'CCCTGGAAGATGGAAGCGTT-3 [SEQ ID NO:15]) or glyceraldehyde 3-phosphate dehydrogenase (GAPDH) cDNA (forward primer: 5' AGAACATCATCC CTGCCTCTACTG-3' [SEQ ID NO:16]; reverse primer: 5'CATGTGGGCCATGAGGTCCACCAC-3' [SEQ ID NO:17]). Reaction was carried out at 48° C. for 45 min for reverse transcription, followed by PCR at 94° C. for denaturing, 55° C. for annealing, and 72° C. for extension. For quantitative evaluation, we initially performed the RT-PCR reaction over a range of cycles (20, 25, 30, 35 and 40) and 25–30 cycles was observed to be within the logarithmic phase of amplification. GAPDH was used in the quantitative RT-PCR analysis as an internal control.

Luciferase assay. HepG2 cells were transfected with 4 μg of a reporter plasmid (WWP-luc, p21 promoter linked with luciferase gene), 2 μg of CMV-NS5A (suboptimal dose) and 1 μg of CMVSRCAP using lipofectamine. 48 h after transfection, luciferase activity was measured as previously described in Ghosh et al., 1999, *J. Gen. Virol.* 80, 1179–1183. Briefly, cells were treated with lysis buffer (Promega), and luciferase activity in the lysates was assayed by integrating the total light emission over 10 seconds using a luminometer (Optocomp II, MGM Instruments). The luciferase activity was normalized based on protein concentration.

Results and Discussion

It was previously demonstrated that the NS5A protein of HCV transcriptionally modulates cellular genes and promotes murine fibroblast cell growth into a tumorigenic phenotype (Ghosh et al., 1999, *J. Gen. Virol.* 80, 1179–1183). Since the predicted amino acid sequence of NS5A does not possess a known DNA binding motif, it appears that NS5A transcriptionally regulates these cellular genes either by direct interaction with general transcriptional factor(s) or through a cofactor. To explore the potential targets of NS5A protein, a yeast two-hybrid screen was performed. Yeast strain HF7c was transformed with pGBT9-5A and colonies were selected on dropout agar medium lacking tryptophan. A few randomly picked colonies were grown and extracted proteins were subjected to SDS-PAGE followed by Western blot analysis using a monoclonal antibody to the Gal4 DNA binding domain. Results indicated pGBT9-5A fusion protein was expressed in all the yeast transformants (data not shown). The expression was also confirmed with a monoclonal antibody to NS5A. For the yeast two-hybrid screening, HF7c yeast cells expressing NS5A were transformed with library plasmid DNAs and selected the candidate colonies on the basis of their ability to grow in the appropriate selection medium and turning on the LacZ gene. Yeast transformants, positive for the activation of two reporter genes, were identified from $2 \times 10^5$ independent transformants. We initially identified 30 β-gal positive clones grown in histidine deficient selective medium. Plasmid DNA was isolated from 17 clones, amplified in bacteria and retransformed into HF7c yeast cells expressing pGBT9-5A gene for confirmation of the positive interaction. Six clones indicated positive growth on selective medium and in the β-gal assay following retransformation. Upon further testing of these clones for interaction with a battery of heterologous baits in yeast, three clones were found to specifically interact with pGBT9-5A and not with other heterologous protein baits. All three clones were sequenced and analyzed by the Blast program. Sequence analysis revealed that these isolates represent an independent overlapping cDNA with homology to a recently identified co-activator SRCAP (Johnston et al, supra).

Figure 9:
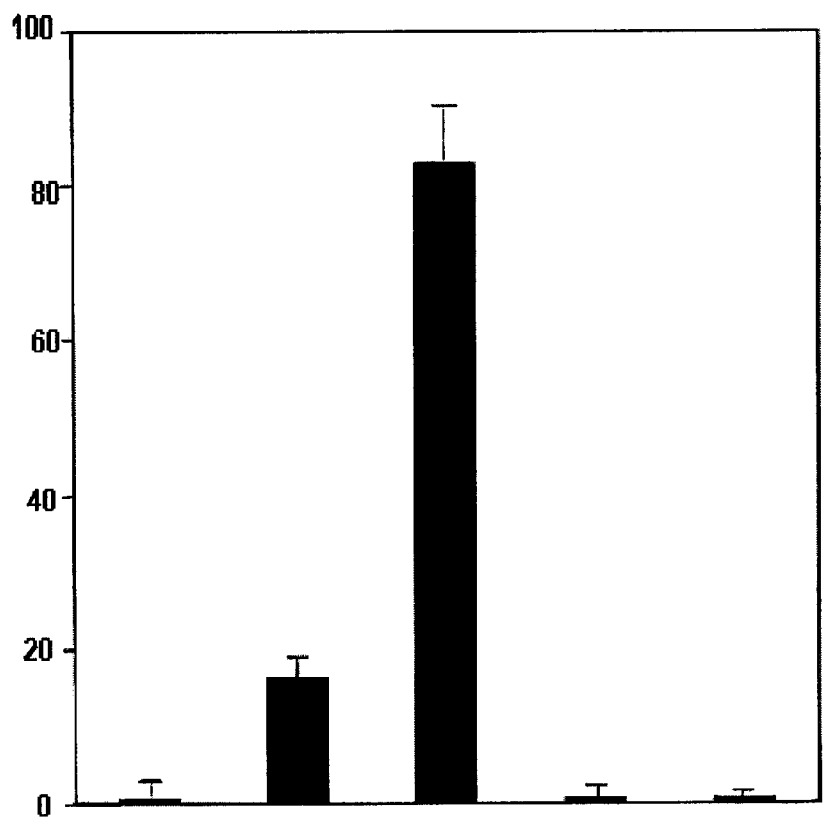
FIG. 9 is a graph demonstrating the interaction of NS5A with SRCAP in a mammalian two hybrid system. HepG2 cells were transfected with 1 μg of G5E1 b-CAT reporter gene, 2 μg of VP16-5A and 2 μg of Gal-SRCAP or Gal-ΔSRCAP. A CAT assay was performed 48 h post transfection. The amount of DNA was kept constant in each transfection by adding the empty vector DNA. SRCAP-NS5A hybrid shows high level of CAT activity as compared to Gal-SRCAP or NS5A alone.

The mammalian version of the conventional two-hybrid assay was used to ascertain whether the candidate NS5A-interacting protein associates with NS5A in mammalian cells. For this purpose, we constructed mammalian expression plasmid vectors that encode a VP16-5A and Gal-SRCAP fusion proteins. The mammalian two-hybrid assay was performed by transfecting HepG2 or NIH3T3 cells with a Gal4-responsive reporter gene (G5E1b-CAT) and pairwise combinations of the appropriate expression vectors. Reporter gene activity was determined by measuring CAT activity in cell lysates from each transfected culture. A significant increase in CAT activity was observed following co-expression of VPI6-5A and Gal-SRCAP hybrids (FIG. 9). However, CAT activity was not enhanced by co-expression of the VP-16-5A and Gal4 vector. CAT activity was detected in Gal-SRCAP and VP-16 vector transfected cells, although the level of CAT expression was much lower as compared to hybrid. We obtained overlapping cDNAs of SRCAP interacting with NS5A from yeast two-hybrid assay. Initial mapping data suggests that NS5A associates with the C-terminal 62 amino acids of SRCAP. To confirm that the C-terminal region of SRCAP indeed interacts with NS5A, we used a C-terminal deletion mutant of SRCAP (Gal-ΔSRCAP) in the mammnalian two-hybrid assay. Results demonstrated that the C-terminal deletion mutant can no longer interact with NS5A under a similar condition (FIG. 9).

An in vitro binding assay was employed to verify the physical interaction between the viral protein NSSA and SRCAP. Histidine tagged NS5A (His-NS5A) was expressed in bacteria, immobilized onto Ni-beads and incubated with $^{35}$S-methionine labeled SRCAP generated by in vitro translation. The proteins binding onto beads was then subjected to SDS-PAGE, followed by autoradiography. Results of the in vitro binding assay exhibited a specific band of SRCAP retained by the His-tagged NS5A-Ni beads FIG. 10A). However, an unrelated cellular protein (His-MBP-1), when used as a negative control under similar experimental conditions, failed to pull-down the SRCAP protein. Results from this in vitro experiment demonstrated that NS5A physically associates with SRCAP.

Figure 10:
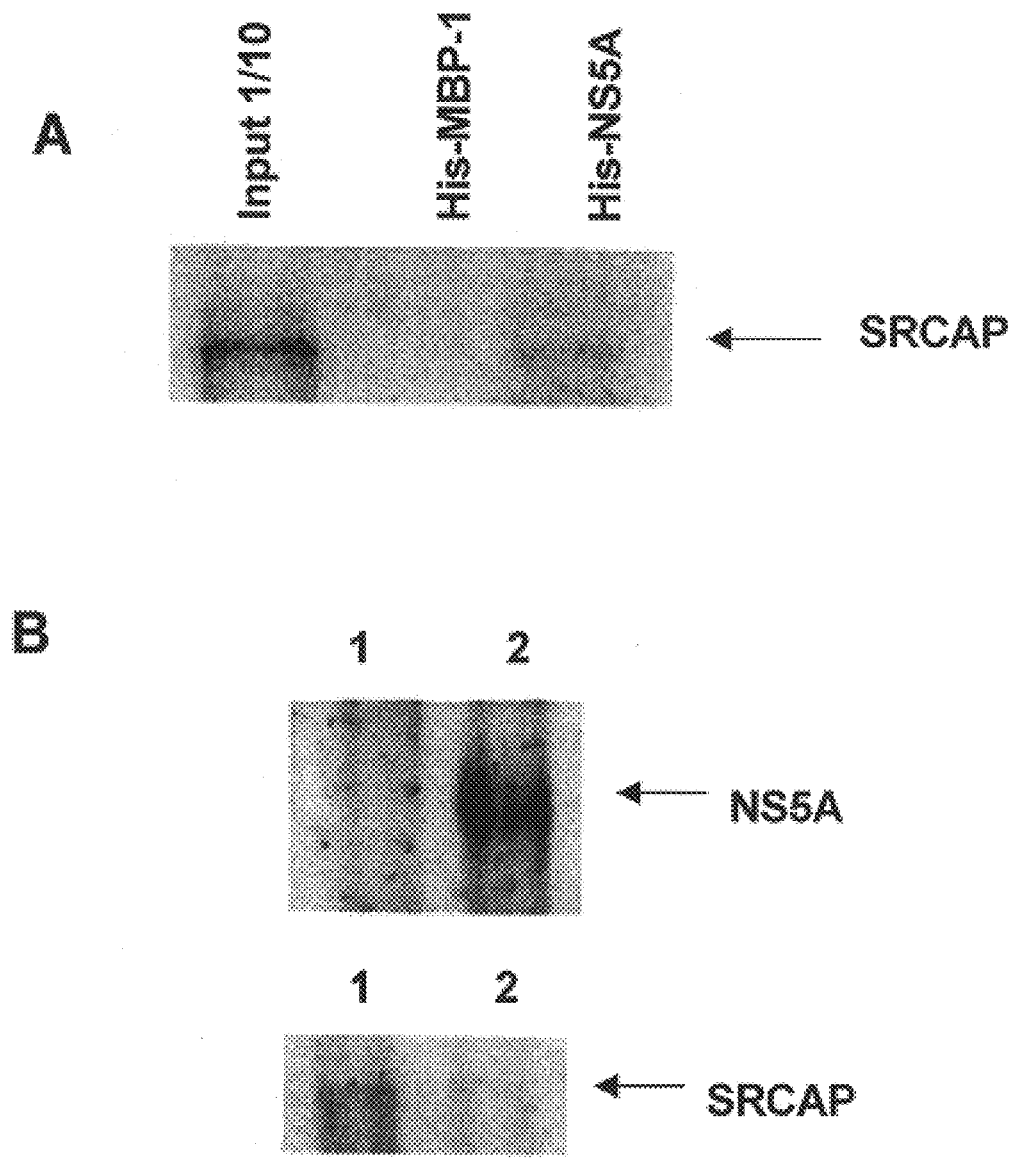
FIG. 10A depicts an autoradiograph.
FIG. 10B depicts immunoblots demonstrating that NS5A protein physically associates with SRCAP.

To investigate the ability of NS5A to associate with endogenous SRCAP in vivo, coimmunoprecipation experiment was performed with lysates of NS5A transfected HepG2 cells. SRCAP specific antibody was used to precipitate the protein complex, followed by Western blot analysis with a specific antibody to detect the NS5A protein (FIG. 10B). Interestingly, NS5A was coprecipitated with endogenous SRCAP, as evident from the specificity of the antibody and the size of the NS5A protein in the immunoblot Vector transfected control HepG2 cell lysates when analyzed similarly did not exhibit a NS5A specific band. The blot was stripped and reprobed with a specific antibody to SRCAP and an endogenous SRCAP band was detected in both the lanes. A similar experiment was performed using an unrelated monoclonal antibody of the same isotype as a negative control. This negative control antibody did not exhibit a detectable reactivity with either SRCAP or NS5A (data not shown). Results suggested that endogenous SRCAP form complex with HCV NS5A. Thus, specific association of SRCAP and NS5A in HepG2 cells was demonstrated using the mammalian two-hybrid system, in vitro pull-down assay and the coimmunoprecipitation analysis.

Figure 11:
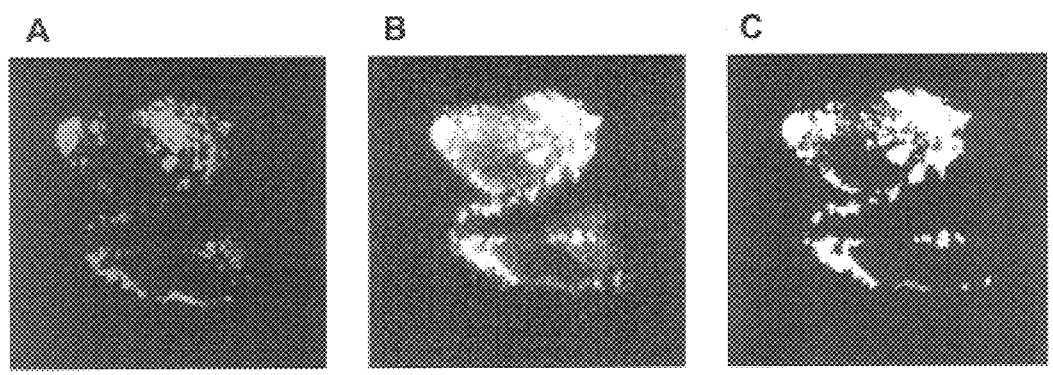
FIG. 11 illustrates the colocalization of transfected NS5A and endogenous SRCAP in HepG2 cells. Immunofluorescent staining was performed using a rabbit polyclonal antibody against NS5A (panel A) and a monoclonal antibody to SRCAP (panel B). Fluorescence images of panels A and B were superimposed digitally for fine comparison (panel C).
Figure 12:
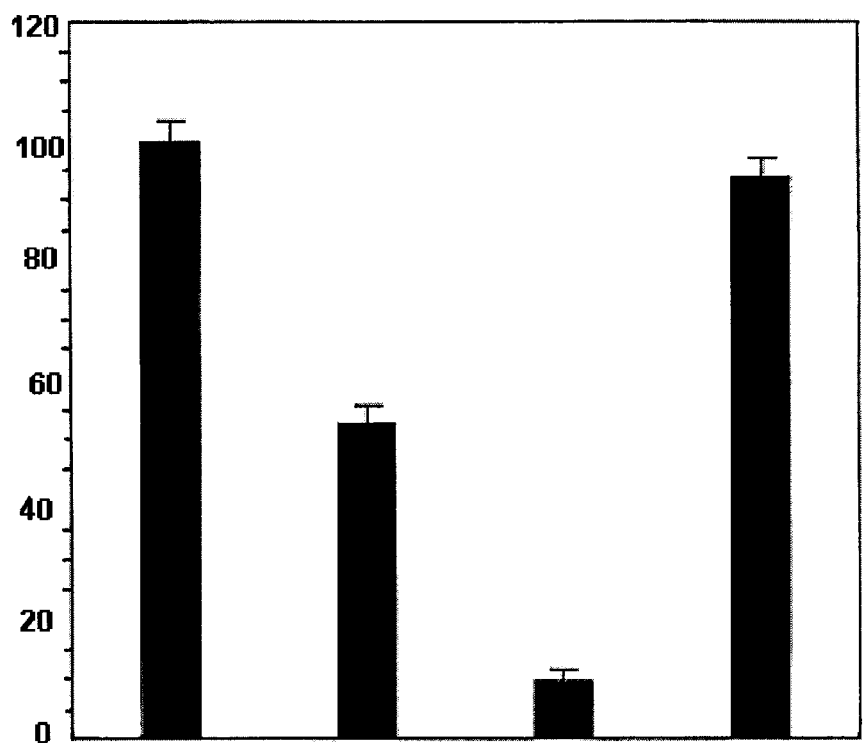
FIG. 12 is a graph of measurements of the transcriptional regulation of p21 promoter by NS5A and SRCAP. Effector plasmid (CMVSRCAP and/or CMV-NS5A) was cotransfected with 4 μg of WWP-luc as the reporter plasmid in HepG2 cells. The total amount of plasmid DNA (7 μg) was kept constant by the addition of empty vector in each transfection. Cell extracts were prepared 48 h post-transfection and luciferase activity was determined. In each set of experiments, triplicate transfections were performed and relative luciferase activity is presented. p21 promoter activity was suppressed when NS5A and SRCAP was coexpressed.
Figure 13:
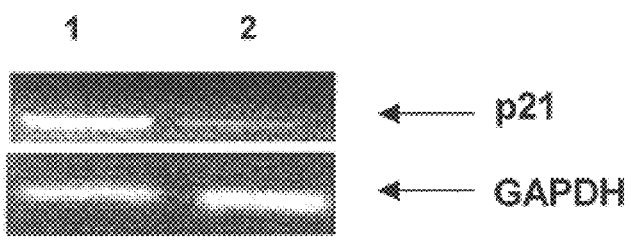
FIG. 13 depicts a RT-PCR analysis of the effect of NS5A and SRCAP on p21 mRNA levels. Panel A depicts a quantitative RT-PCR analysis for endogenous p21 or GAPDH mRNA from NIH3T3neo (lane 1) and NIH3T3NS5A (lane 2) cells. Panel B depicts the detection of luciferase mRNA by RT-PCR from transiently transfected p21-luciferase (lane 1), p21-luciferase with NS5A (lane 2), and p21-luciferase with NS5A and SRCAP (lane 3). GAPDH was used as an internal control.
Figure 13:
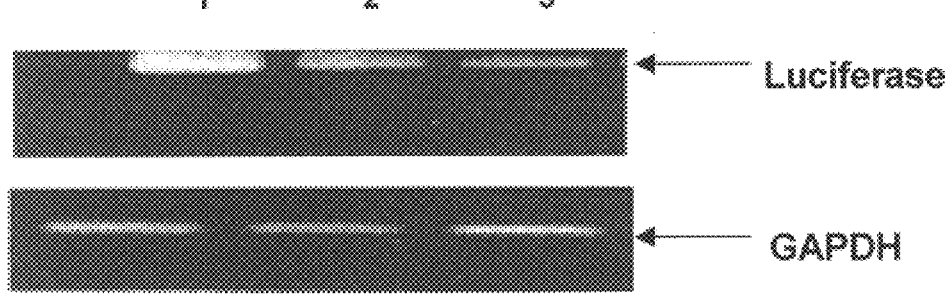

Further studies examined whether NS5A protein can colocalize with the endogenous SRCAP. We initially investigated the localization of endogenous SRCAP by indirect immunofluorescence in HepG2 cells using a monoclonal antibody to SRCAP. Immunofluorescent staining of the SRCAP protein showed a predominant perinuclear localization with occasional nuclear staining. Similarly, cells transfected with CMV-NS5A plasmid DNA, when stained with polyclonal antiserum, exhibits perinuclear staining (Tanji et al, 1995, *J. Virol.* 69, 3980–3986). To compare the subcellular localization of SRCAP with NS5A, HepG2 cells were transfected with CMV-NS5A and immunofluorescent staining was performed with antibodies to NS5A and SRCAP. Confocal microscopy showed a significant colocalization of the endogenous SRCAP with NS5A (FIG. 11). There was no detectable staining when normal control sera were used. HCV may benefit by regulation of cellular gene(s) leading to the disruption of normal cell growth Viral genes can override cellular control mechanisms which in untransformed cells regulates cell cycle progression in response to various antiproliferative signals. HCV often causes persistent infection and is a silent disease. In HCV persistently infected cells, the continued presence of viral gene products is likely to be detrimental for host cells, since HCV NS5A protein transcriptionally downregulates p21 activity (Ghosh et al., 1999, *J. Gen. Virol.* 80, 1179–1183). Cell cycle progression is driven by the sequential activation of cyclin-dependent kinases (CDKs) which are subject to regulation by positive (cyclins) and negative (CDK-inhibitory proteins) effectors (Morgan, 1995, *Nature* 374, 131–134). One such effector is the universal CDK inhibitor p21/waf 1 (Harper et al., 1993, *Cell* 75, 805–816; Yang et al., 1995, *Nature Med.* 1, 1052–1056). p21 may participate in apoptosis and increased p21 expression correlates with enhanced cell death under certain conditions (El-Deiry et al., 1993, *cell* 75, 817–825; Sheikh et al., 1995, *Oncogene* 11, 1899–1905). p21 protein binds and inhibits the activity of CDKs by preventing the phosphorylation of critical CDK substrates and by blocking cell cycle progression (Harper et al., 1993, *Cell* 75, 805–816; Xiong et al., supra). To further examine the effects of NS5A and SRCAP on a natural promoter, HepG2 or NIH3T3 cells were transfected with a reporter construct (p21 promoter linked with luciferase gene), CMV-NS5A and CMV-SRCAP as the effector plasmids. Results from the luciferase assay suggested that inhibition of p21 promoter activity by NS5A protein was higher in presence of SRCAP (FIG. 12). However, CMV-SRCAP alone at the same concentration did not show a significant effect on p21 promoter activity. A similar result was observed in NIH3T3 cells. To further examine the effect of NS5A on p21 promoter at the transcriptional level, a quantitative RT-PCR was performed using total RNA from stably or transiently transfected cells. This assay was designed to separately analyze the effect of NS5A and SRCAP directly on the p21 mRNA level or on the transcription of a tagged luciferase reporter gene. Results suggested downregulation of p21 promoter activity at the transcriptional level by NS5A alone or together with SRCAP (FIG. 13).

This example discloses that SRCAP physically associates with HCV NS5A protein. SRCAP was isolated in three independently derived cDNA clones in yeast two-hybrid screening. The interaction of HCV NS5A protein with SRCAP was confirmed by mammalian two-hybrid assay, pull-down experiment and from coirmnmunoprecipitation studies. HCV NS5A colocalizes with SRCAP at the perinuclear membrane of HepG2 cells. Preliminary mapping analysis suggests that the binding of NS5A occurs with SRCAP through the C-terminus (62 amino acids), which contains highly charged residues. HCV NS5A also possesses several acidic domains (Tanimoto et al., supra; Kato et al., 1997. *J. Virol.* 71, 8856–8859). Whether the SRCAP binding domain of NS5A resides within one of these acidic domains remains to be elucidated. NS5A is suggested as a potent transcriptional activator. However, it exerts a negative regulatory activity on the p21 promoter in favor of promoting cell growth. SRCAP alone increases the E1b promoter activity when brought closer by Gal4 DNA binding domain to the promoter sequences (Johnston et al., supra). Although SRCAP is defined as a co-activator, it behaves like a corepressor when it associates with NS5A to exert a negative effect on the p21 promoter. We propose NS5A may recruit endogenous SRCAP to repress the p21 promoter. Transcription factors that activate in one circumstance and repress in another have been documented and the molecular basis for these transitions are quite diverse (reviewed in Roberts et al., 1995, *Nature* 375, 105–106; McKnight, 1996, *Genes Dev.* 10, 367–381). NS5A has recently been demonstrated to bind with the cellular factor Grb2 at the SH3 domain, which perturbs the mitogenic signaling pathways (Tan et al., 1999, *Proc. Natl. Acad. Sci. USA* 96, 5533–5538). Interaction between HCV NS5A and a SNARE-like protein (hVAP33) has also recently been reported (Tu et al., 1999, *Virology* 263, 30–41). Our observations add a novel cellular protein SRCAP to the list of NS5A interacting cellular factors. To our knowledge, this is the first report dissecting the transregulatory activity of NS5A and implicating its relation with a cellular factor. We propose the recruitment of SRCAP by NS5A is one of the mechanisms for its transcription modulatory activity. This may also explain the growth promoting activity of HCV NS5A.

EXAMPLE 3

This example further characterizes SRCAP activities. SRCAP regulates transcription of the MMTV Promoter.

Figure 14:
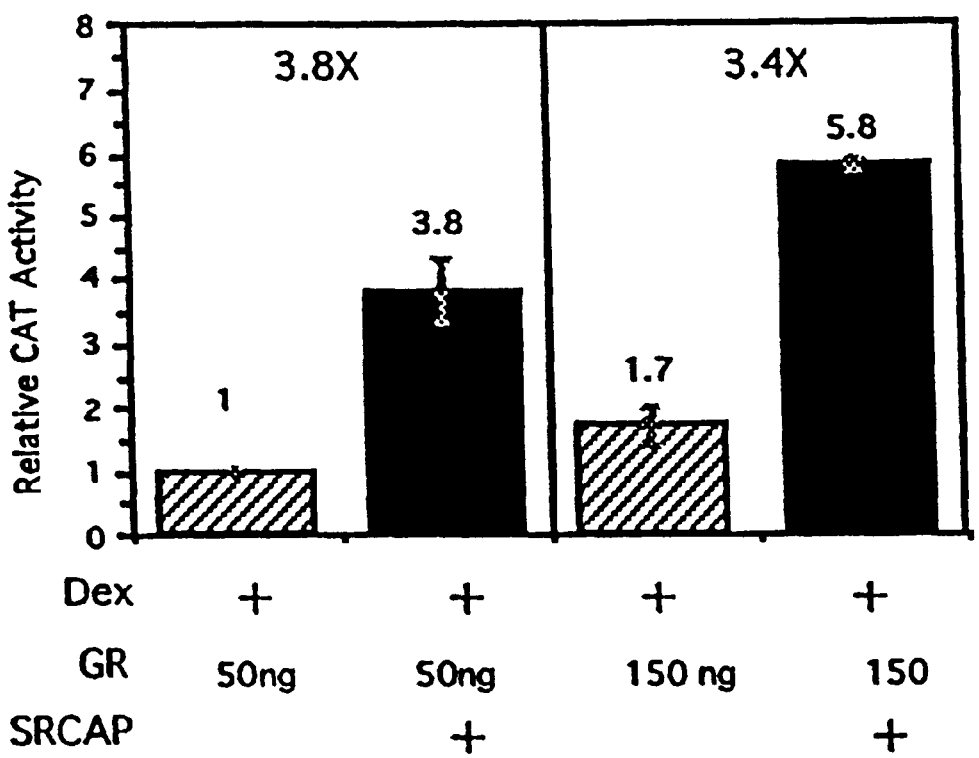
FIG. 14 is a graph demonstrating that SRCAP activates GR-mediated transcription. The ability of SRCAP to influence GR-mediated transcription of the MMTV promoter was tested by transient transfection. CHO cells were transiently transfected as indicated with 150 ng of the reporter gene MMTV CAT, 50 ng or 150 ng of GR, and 1200 ng of SRCAP. Eighteen hours post-transfection, dexamethasone was added to a concentration of $10^{-6}$ M and 24 hours later the cells were harvested and CAT enzyme activity measured. Values are the means and S.E. from two separate experiments in which each point was performed in triplicate.

Examination of the primary sequence of SRCAP indicated it contains several LXXLL motifs, which have been found in other proteins to mediate interaction with nuclear receptors (McInerney et al., 1998, *Genes Devel.* 12, 3357–3368). This prompted us to test whether SRCAP might regulate glucocorticoid receptor (GR) mediated transcription. For these studies we tested the ability of SRCAP to regulate GR-mediated transcription of the MMTV promoter. As shown in FIG. 14, we found that SRCAP enhanced GR-mediated transcriptional activation by 3 to 4-fold.

In experiments not shown, SRCAP in the absence of GR did not activate transcription of the MMTV promoter. This contrasts with our findings that SRCAP can directly activate transcription of the Vitellogenin A2 promoter. 35 SRCAP can be co-immuno recidiated with several proteins.

Figure 15:
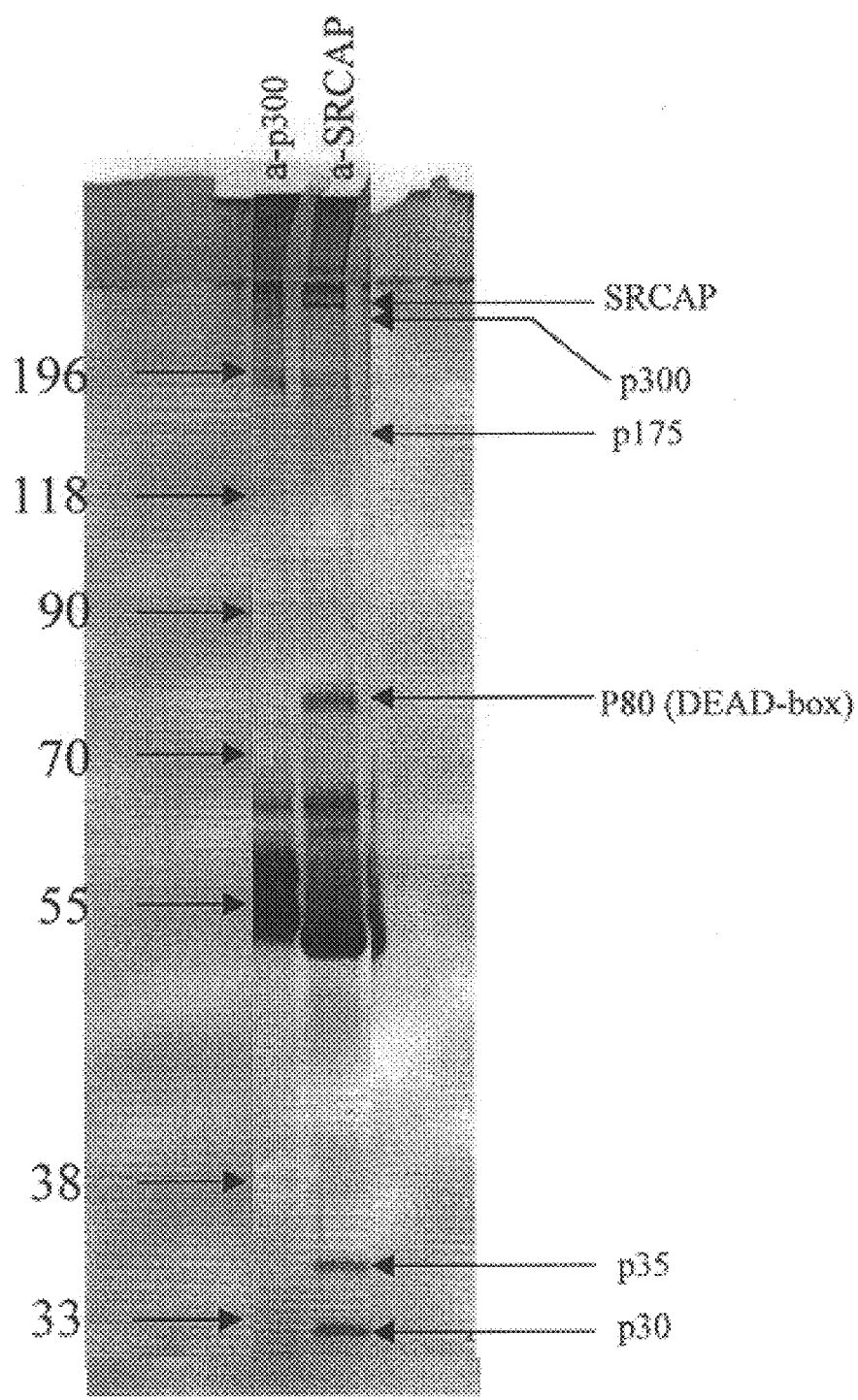
FIG. 15 is a stained PAGE gel demonstrating that an anti-SRCAP monoclonal antibody immunoprecipitates SRCAP with several other proteins. Monoclonal antibodies raised against either the C-terminal end of SRCAP (amino acids 2733–2971) or against p300/CBP were used to precipitate proteins from extracts of A549 cells. Immunoprecipitated proteins were analyzed by SDS-PAGE and visualized by silver staining.

To identify proteins that associate with SRCAP, we have developed a monoclonal antibody that recognizes the C-terminal end of SRCAP (amino acids 2733–2971). This was used to immunoprecipitate SRCAP from total cellular extract made by treating A549 cells with a low detergent lysis buffer that has been shown to maintain association of CBP with other cellular proteins (three-100 mm tissue dishes were used). Immunoprecipitated proteins were size fractionated on SDS-PAGE gels and proteins visualized by silver staining. Results are shown in FIG. 15. The position of the 80 kD, 35, and 30 kD proteins which co-precipitated with SRCAP are shown by the arrows. The heavily stained proteins are the monoclonal antibody heavy and light chains.

To rule out the possibility that the co-precipitated proteins were contaminating serum proteins from the FBS in the cell culture media rather than bona fide A549 cellular proteins, we have repeated the inimunoprecipitation using extracts made from cells metabolically labeled using $^{35}$S-methionine. In these experiments, SRCAP, CBP, the 160–180 kD proteins, the 80 kD, 38 kD and the 30 kD proteins are $^{35}$S-labeled indicating they are not serum proteins. We also wanted to rule out the possibility that these proteins are directly recognized by the anti-SRCAP monoclonal rather than being co-immunoprecipitated due to their association with SRCAP. To do this we have repeated the immunoprecipitation using cellular extracts made with lysis buffer having a high detergent content (RIPA buffer) which has been shown to disrupt binding of p300/CBP with other cellular proteins (Wang et al., 1995, *J. Virol.* 69, 7917–7924). In the high detergent extract the anti-SRCAP antibody recognized only SRCAP but not CBP, the 160–180 kD proteins, or the 80 kD, 38 kD and 30 kD proteins (data not shown).

Collectively, the results of our immunoprecipitation studies indicate that proteins associated with SRCAP can be purified using the anti-SRCAP antiserum. To identify these proteins we scaled up our purification protocol. Extracts from twenty 150 mm plates were incubated with the anti-SRCAP antibody and immunoprecipitated proteins were size fractionated by SDS-PAGE gels and proteins visualized by staining with Coomassie brilliant blue. The bands corresponding to the 80 kD, 38 kD and 30 kD bands were excised and sent for MALD-MS analysis at the HHMI Biopolymer/W.M. Keck Foundation Biotechnology Resource Laboratory at Yale University. The result of this analysis indicated that the 80 kD protein is the X isoform of human DEAD box RNA dependent helicase. Interestingly, studies by others have indicated that DEAD box protein functions as a transcriptional activator regulated by association with a hepatitis C core protein (You et al., 1999, *J. Virology* 73, 2841–2853). Characterization of the domains within SRCAP that activate transcription using Gal-SRCAP chimeras As discussed in Example 1, the Gal-SRCAP$_{1275-2971}$ chimera activates transcription of a Gal-CAT reporter gene in HeLa cells.

Figure 16:
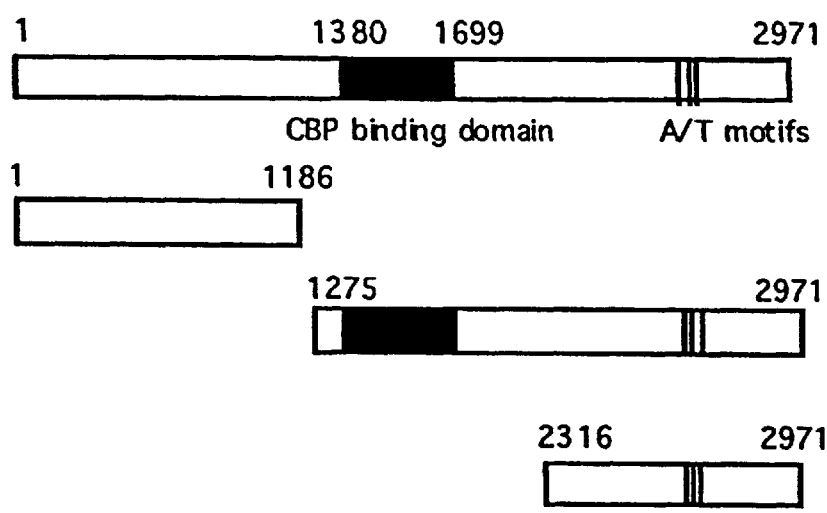
FIG. 16 is a schematic showing regions of SRCAP used to make Gal chimeras.
Figure 17:
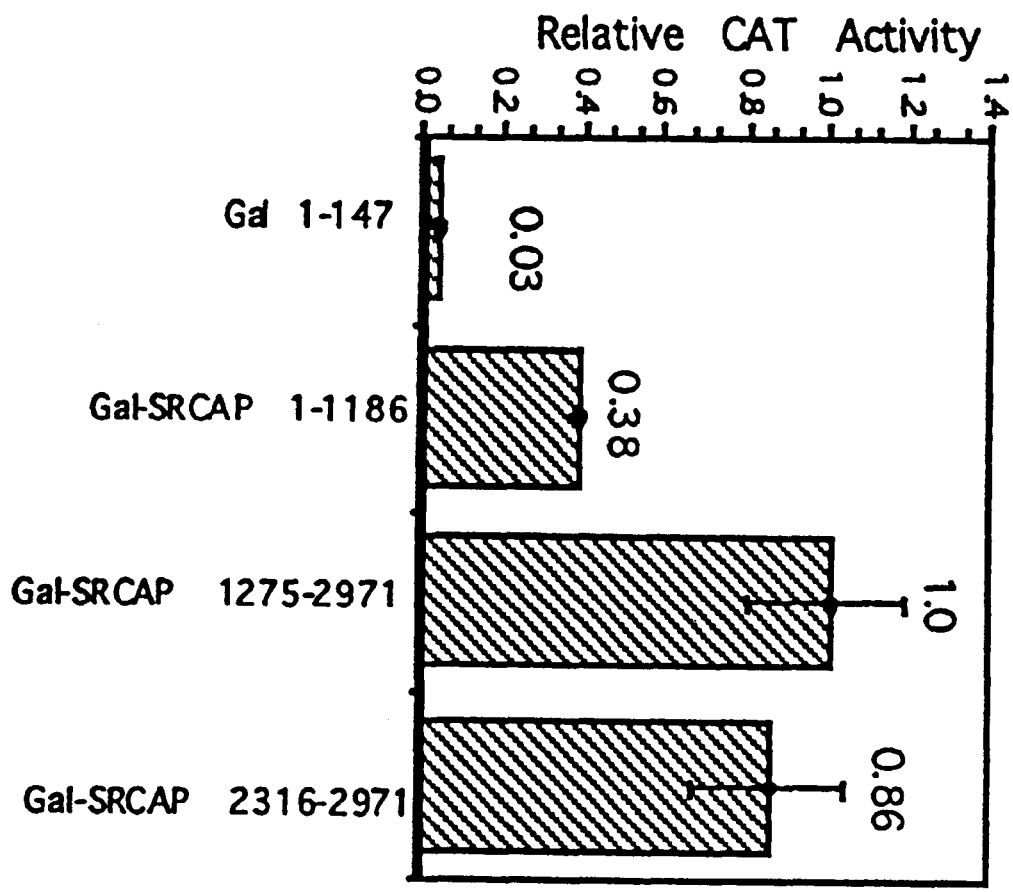
FIG. 17 is a graph demonstrating that multiple regions within SRCAP function as Gal chimeras to activate transcription. The ability of Gal-SRCAP$_{1-1186}$, Gal-SRCAP$_{2316-2971}$ and Gal$_{1-147}$ to activate transcription was compared to the activity of Gal-SRCAP$_{1275-2971}$. HeLa cells were transiently transfected with the reporter gene pGal-CAT and equal molar amounts of each Gal chimera. Values are the means and S.E. from two separate experiments in which each point was performed in triplicate.

To identify other regions within SRCAP that activate transcription, we generated and tested the transcriptional activity of two additional Gal-SRCAP chimeras. As shown in FIGS. 16 and 17, the Gal-SRCAP$_{1-1186}$ and Gal-SRCAP$_{2316-2971}$ chimeras also activate transcription. These results indicate SRCAP contains at least two domains involved in activation of transcription, One domain is located within SRCAP amino acids 1–1186 and the second domain is located within SRCAP amino acids 2316–2971. Since these regions of SRCAP activate transcription despite the lack of a CBP binding site, it indicates that SRCAP activates transcription at least in part through a CBP-independent mechanism.

Figure 18:
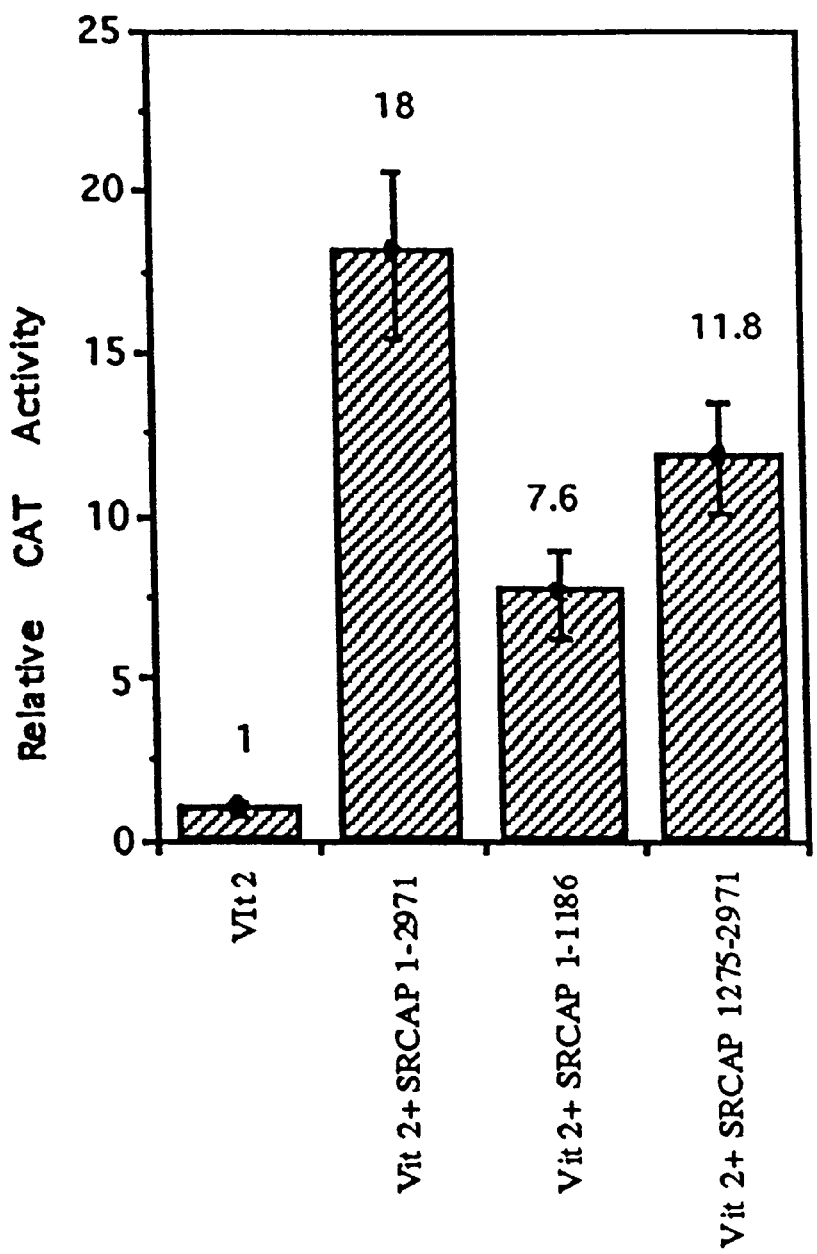
FIG. 18 is a graph demonstrating that SRCAP activates transcription of the Vitellogenin 2 promoter. A549 cells were transfected with the reporter gene Vitellogenin 2 CAT and equal molar amounts of plasmids encoding SRCAP 1–2971, SRCAP 1275–2971, or SRCAP 1–1186. The relative CAT activity is reported compared to the transcriptional activity of the Vitellogenin 2 CAT reporter gene alone. Values are the means and S.E. from two separate experiments in which each point was performed in triplicate.

We have also found that several SRCAP peptides (with no Gal$_{1-147}$ moiety attached) can activate transcription. As shown in FIG. 18, SRCAP$_{1-1186}$, SRCAP$_{1275-2971}$ and SRCAP$_{1-2971}$ proteins activated transcription of the Xenopus Vitellogenin A2 promoter. These same SRCAP peptides did not activate transcription of other reporter genes such as TK-CAT and SV-40-CAT. This result indicates that ability of the Gal-SRCAP$_{1-1186}$ and the Gal-SRCAP$_{1275-2971}$ to activate transcription due to presentation as a Gal chimera.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An isolated and purified SRCAP polypeptide, the polypeptide comprising the amino Ad acid sequence of SEQ ID NO:2, or a conservatively substituted variant thereof, wherein the polypeptide has ATPase activity and transcriptional activation acivity.

2. The polypeptide of claim 1, consisting essentiallly of SEQ ID NO:2.

3. An isolated and purified polypeptide comprising an amino acid sequence that has at least 80% sequence homology to SEQ ID NO:2, wherein the polypeptide has ATPase activity and transcriptional activation activity.

4. The polypeptide of claim 3, comprising an amino acid sequence that has at least about 90% sequence homology to SEQ ID NO:2.

5. A polypeptide comprising at least 15 contiguous amino acids of the polypeptide of claim 3.

6. The polypeptide of claim 5, wherein the polypeptide has a SRCAP activity selected from the group consisting of ATPase, CREB binding protein (CBP) interaction and transcriptional co-activation, transcriptional activation without CBP, and DNA binding.

7. A SRCAP chimera comprising the polypeptide of claim 5 covalently attached to an amino acid sequence from a naturally occurring protein that is not SRCAP.

8. The chimera of claim 7, wherein the protein that is not SRCAP is a GAL4.

9. A polynucleotide comprising a nucleic acid encoding the polypeptide of claim 1.

10. The polynucleotide of claim 9, comprising SEQ ID NO:11.

11. A polynucleotide encoding the polypeptide of claim 3.

12. A polynucleotide encoding the polypeptide of claim 5.

13. A polynucleotide that comprises:

(a) SEQ ID NO:11;

(b) a sequence complementary to (a);

(c) a sequence capable of selectively hybridising to a sequence in either (a) or (b); or (d) a fragment of any of sequences (a) to (c) that at least 45 nucleotides long.

14. A vector comprising the polynucleotide of claim 11.

15. A recombinant cell comprising the vector of claim 14.

16. The polynucleotide of claim 13, wherein the polynucleotide is capable of hybridizing to a SRCAP mRNA.

17. A ribozyme which specifically cleaves the polynucleotide of claim 11.

18. A polynucleotide encoding the chimera of claim 7.

19. An antibody that specifically binds to the SRCAP polypeptide or portion of claim 3.

20. A method of activating transcription in a cell, comprising treating the cell with the SRCAP polypeptide of claim 3, or a polynucleotide encoding said polypeptide.

21. A method of detecting a SRCAP in a sample, comprising treating the sample with the antibody of claim 19, then determining whether the antibody specifically binds to a component of the sample, wherein specific binding indicates the presence of SRCAP in the sample.

22. A method of detecting the polynucleotide of claim 11 in a sample, comprising treating the sample with a second polynucleotide that specifically hybridizes with the polynucleotide of claim 11, then determining if the second polynucleotide specifically hybridized with a component of the sample.

23. A method of detecting the polynucleotide of claim 11 in a sample, comprising treating the sample with a second polynucleotide that specifically hybridizes with the polynucleotide of claim 13, then perform a polymerase amplification method.

24. A method of enhancing CREB binding protein (CBP)-mediated activation of transcription in a cell, comprising treating the cell with the polypeptide of claim 3 or a polynucleotide encoding said polypeptide.

25. A method for identifying a compound that modulates SRCAP protein finction comprising determining whether a candidate modulator compound alters the interaction of the SRCAP protein of claim 3 with CBP.

26. A method for identifying a compound that modulates SRCAP finction comprising assessing the effect of the compound on the activity of the SRCAP protein of claim 3 as an ATPase, in CBP interaction and transcriptional co-activation, in transcriptional activation without CBP, or in DNA binding.

27. A method for treating a patient having a disease involving a function affected by SRCAP protein comprising administering the polypeptide of claim 3, or a polynucleotide encoding said polypeptide, to the patient.

28. The method of claim 27, wherein the finction is insufficient transcription of a gene selected from the group consisting of a gene mediated by CBP co-activation, a DEAD box RNA dependent helicase, adenoviral DBP protein, β-actin, and a nuclear receptor.

29. A method for treating a patient having a disease mediated by SRCAP-activated transcription comprising administering to the patient a compound that decreases SRCAP activity in the patient.

30. The method of claim 29 wherein the disease is a virus infection.

* * * * *

SEQUENCE LISTING

```
<160> NUMBER OF SEQ ID NOS:  17

<210> SEQ ID NO 1
<211> LENGTH: 3118
<212> TYPE: PRT
<213> ORGANISM: Human

<400> SEQUENCE: 1

Ala Gln Asp Ser Ser Leu Asp Gly Pro Pro Gly Pro Pro Asp Gly Ala
  1               5                  10                  15

Thr Val Pro Leu Glu Gly Phe Ser Leu Ser Gln Ala Ala Asp Leu Ala
                 20                  25                  30

Asn Lys Gly Pro Lys Trp Glu Lys Ser His Ala Glu Ile Ala Glu Gln
             35                  40                  45

Ala Lys His Glu Ala Glu Ile Glu Thr Arg Ile Ala Glu Leu Arg Lys
         50                  55                  60

Glu Gly Phe Trp Ser Leu Lys Arg Leu Pro Lys Val Pro Glu Pro Pro
 65                  70                  75                  80

Arg Pro Lys Gly His Trp Asp Tyr Leu Cys Glu Glu Met Gln Trp Leu
                 85                  90                  95
```

-continued

```
Ser Ala Asp Phe Ala Gln Glu Arg Arg Trp Lys Arg Gly Val Ala Arg
            100                 105                 110
Lys Val Val Arg Met Val Ile Arg His His Glu Glu Gln Arg Gln Lys
            115                 120                 125
Glu Glu Arg Ala Arg Arg Glu Glu Gln Ala Lys Leu Arg Arg Ile Ala
            130                 135                 140
Ser Thr Met Ala Lys Asp Val Arg Gln Phe Trp Ser Asn Val Glu Lys
145                 150                 155                 160
Val Val Gln Phe Lys Gln Gln Ser Arg Leu Glu Glu Lys Arg Lys Lys
                    165                 170                 175
Ala Leu Asp Leu His Leu Asp Phe Ile Val Gly Gln Thr Glu Lys Tyr
                180                 185                 190
Ser Asp Leu Leu Ser Gln Ser Leu Asn Gln Pro Leu Thr Ser Ser Lys
            195                 200                 205
Ala Gly Ser Ser Pro Cys Leu Gly Ser Ser Ala Ala Ser Ser Pro
            210                 215                 220
Pro Pro Pro Ala Ser Arg Leu Asp Asp Glu Asp Gly Asp Phe Gln Pro
225                 230                 235                 240
Gln Glu Asp Glu Glu Asp Asp Glu Glu Thr Ile Glu Val Glu Glu
                    245                 250                 255
Gln Gln Glu Gly Asn Asp Ala Glu Ala Gln Arg Arg Glu Ile Glu Leu
                260                 265                 270
Leu Arg Arg Glu Gly Glu Leu Pro Leu Glu Glu Leu Leu Arg Ser Leu
            275                 280                 285
Pro Pro Gln Leu Leu Glu Gly Pro Ser Ser Pro Ser Gln Thr Pro Ser
        290                 295                 300
Ser His Asp Ser Asp Thr Arg Asp Gly Pro Glu Glu Gly Ala Glu Glu
305                 310                 315                 320
Glu Pro Pro Gln Val Leu Glu Ile Lys Pro Pro Ser Ala Val Thr
                    325                 330                 335
Gln Arg Asn Lys Gln Pro Trp His Pro Asp Glu Asp Glu Glu Phe
                340                 345                 350
Thr Ala Asn Glu Glu Glu Ala Glu Asp Glu Glu Asp Thr Ile Ala Ala
            355                 360                 365
Glu Glu Gln Leu Glu Gly Glu Val Asp His Ala Met Glu Leu Ser Glu
        370                 375                 380
Leu Ala Arg Glu Gly Glu Leu Ser Met Glu Glu Leu Leu Gln Gln Tyr
385                 390                 395                 400
Ala Gly Ala Tyr Ala Pro Gly Ser Gly Ser Ser Glu Asp Glu Asp Glu
                    405                 410                 415
Asp Glu Val Asp Ala Asn Ser Ser Asp Cys Glu Pro Glu Gly Pro Val
                420                 425                 430
Glu Ala Glu Pro Pro Gln Glu Asp Ser Ser Gln Ser Asp Ser
            435                 440                 445
Val Glu Asp Arg Ser Glu Asp Glu Glu Asp Glu His Ser Glu Glu Glu
            450                 455                 460
Glu Thr Ser Gly Ser Ser Ala Ser Glu Glu Ser Glu Ser Glu Glu Ser
465                 470                 475                 480
Glu Asp Ala Gln Ser Gln Ser Gln Ala Asp Glu Glu Glu Asp Asp
                    485                 490                 495
Asp Phe Gly Val Glu Tyr Leu Leu Ala Arg Asp Glu Glu Gln Ser Glu
            500                 505                 510
Ala Asp Ala Gly Ser Gly Pro Pro Thr Pro Gly Pro Thr Thr Leu Gly
```

-continued

```
          515                 520                 525
Pro Lys Lys Glu Ile Thr Asp Ile Ala Ala Ala Glu Ser Leu Gln
        530                 535                 540
Pro Lys Gly Tyr Thr Leu Ala Thr Thr Gln Val Lys Thr Pro Ile Pro
545                 550                 555                 560
Leu Leu Leu Arg Gly Gln Leu Arg Glu Tyr Gln His Ile Gly Leu Asp
                565                 570                 575
Trp Leu Val Thr Met Tyr Glu Lys Lys Leu Asn Gly Ile Leu Ala Asp
                580                 585                 590
Glu Met Gly Leu Gly Lys Thr Ile Gln Thr Ile Ser Leu Leu Ala His
            595                 600                 605
Leu Ala Cys Glu Lys Gly Asn Trp Gly Pro His Leu Ile Ile Val Pro
        610                 615                 620
Thr Ser Val Met Leu Asn Trp Glu Met Glu Leu Lys Arg Trp Cys Pro
625                 630                 635                 640
Ser Phe Lys Ile Leu Thr Tyr Tyr Gly Ala Gln Lys Glu Arg Lys Leu
                645                 650                 655
Lys Arg Gln Gly Trp Thr Lys Pro Asn Ala Phe His Val Cys Ile Thr
                660                 665                 670
Ser Tyr Lys Leu Val Leu Gln Asp His Gln Ala Phe Arg Arg Lys Asn
            675                 680                 685
Trp Arg Tyr Leu Ile Leu Asp Glu Ala Gln Asn Ile Lys Asn Phe Lys
        690                 695                 700
Ser Gln Arg Trp Gln Ser Leu Leu Asn Phe Asn Ser Gln Arg Arg Leu
705                 710                 715                 720
Leu Leu Thr Gly Thr Pro Leu Gln Asn Ser Leu Met Glu Leu Trp Ser
                725                 730                 735
Leu Met His Phe Leu Met Pro His Val Phe Gln Ser His Arg Glu Phe
                740                 745                 750
Lys Glu Trp Phe Ser Asn Pro Leu Thr Gly Met Ile Glu Gly Ser Gln
            755                 760                 765
Glu Tyr Asn Glu Gly Leu Val Lys Arg Leu His Lys Val Leu Arg Pro
        770                 775                 780
Phe Leu Leu Arg Arg Val Lys Val Asp Val Glu Lys Gln Met Pro Lys
785                 790                 795                 800
Lys Tyr Glu His Val Ile Arg Cys Arg Leu Ser Lys Arg Gln Arg Cys
                805                 810                 815
Leu Tyr Asp Asp Phe Met Ala Gln Thr Thr Lys Glu Thr Leu Ala
                820                 825                 830
Thr Gly His Phe Met Ser Val Ile Asn Ile Leu Met Gln Leu Arg Lys
            835                 840                 845
Val Cys Asn His Pro Asn Leu Phe Asp Pro Arg Pro Val Thr Ser Pro
        850                 855                 860
Phe Ile Thr Pro Gly Ile Cys Phe Ser Thr Ala Ser Leu Val Leu Arg
865                 870                 875                 880
Ala Thr Asp Val His Pro Leu Gln Arg Ile Asp Met Gly Arg Phe Asp
                885                 890                 895
Leu Ile Gly Leu Glu Gly Arg Val Ser Arg Tyr Glu Ala Asp Thr Phe
                900                 905                 910
Leu Pro Arg His Arg Leu Ser Arg Arg Val Leu Leu Glu Val Ala Thr
            915                 920                 925
Ala Pro Asp Pro Pro Arg Pro Lys Pro Val Lys Met Lys Val Asn
        930                 935                 940
```

-continued

```
Arg Met Leu Gln Pro Val Pro Lys Gln Glu Gly Arg Thr Val Val Val
945                 950                 955                 960

Val Asn Asn Pro Arg Ala Pro Leu Gly Pro Val Pro Val Arg Pro Pro
            965                 970                 975

Pro Gly Pro Glu Leu Ser Ala Gln Pro Thr Pro Gly Pro Val Pro Gln
        980                 985                 990

Val Leu Pro Ala Ser Leu Met Val Ser Ala Ser Pro Ala Gly Pro Pro
    995                 1000                1005

Leu Ile Pro Ala Ser Arg Pro Pro Gly Pro Val Leu Leu Pro Pro Leu
    1010                1015                1020

Gln Pro Asn Ser Gly Ser Leu Pro Gln Val Leu Pro Ser Pro Leu Gly
1025                1030                1035                1040

Val Leu Ser Gly Thr Ser Arg Pro Pro Thr Pro Thr Leu Ser Leu Lys
            1045                1050                1055

Pro Thr Pro Pro Ala Pro Val Arg Leu Ser Pro Ala Pro Pro Pro Gly
            1060                1065                1070

Ser Ser Ser Leu Leu Lys Pro Leu Thr Val Pro Pro Gly Tyr Thr Phe
        1075                1080                1085

Pro Pro Ala Ala Ala Thr Thr Thr Ser Thr Thr Thr Ala Thr Ala Thr
        1090                1095                1100

Thr Thr Ala Val Pro Ala Pro Thr Pro Ala Pro Gln Arg Leu Ile Leu
1105                1110                1115                1120

Ser Pro Asp Met Gln Ala Arg Leu Pro Ser Gly Glu Val Val Ser Ile
            1125                1130                1135

Gly Gln Leu Ala Ser Leu Ala Gln Arg Pro Val Ala Asn Ala Gly Gly
            1140                1145                1150

Ser Lys Pro Leu Thr Phe Gln Ile Gln Gly Asn Lys Leu Thr Leu Thr
            1155                1160                1165

Gly Ala Gln Val Arg Gln Leu Ala Val Gly Gln Pro Arg Pro Leu Gln
    1170                1175                1180

Met Pro Pro Thr Met Val Asn Asn Thr Gly Val Val Lys Ile Val Val
1185                1190                1195                1200

Arg Gln Ala Pro Arg Asp Gly Leu Thr Pro Val Pro Pro Leu Ala Pro
            1205                1210                1215

Ala Pro Arg Pro Pro Ser Ser Gly Leu Pro Ala Val Leu Asn Pro Arg
            1220                1225                1230

Pro Thr Leu Thr Pro Gly Arg Leu Pro Thr Pro Thr Leu Gly Thr Ala
        1235                1240                1245

Arg Ala Pro Met Pro Thr Pro Thr Leu Val Arg Pro Leu Leu Lys Leu
    1250                1255                1260

Val His Ser Pro Ser Pro Glu Val Ser Ala Ser Ala Pro Gly Ala Ala
1265                1270                1275                1280

Pro Leu Thr Ile Ser Ser Pro Leu His Val Pro Ser Ser Leu Pro Gly
            1285                1290                1295

Pro Ala Ser Ser Pro Met Pro Ile Pro Asn Ser Ser Pro Leu Ala Ser
            1300                1305                1310

Pro Val Ser Ser Thr Val Ser Val Pro Leu Ser Ser Ser Leu Pro Ile
        1315                1320                1325

Ser Val Pro Thr Thr Leu Pro Ala Pro Ala Ser Ala Pro Leu Thr Ile
    1330                1335                1340

Pro Ile Ser Ala Pro Leu Thr Val Ser Ala Ser Gly Pro Ala Leu Leu
1345                1350                1355                1360
```

```
Thr Ser Val Thr Pro Pro Leu Ala Pro Val Pro Ala Ala Pro Gly
            1365                1370                1375

Pro Pro Ser Leu Gln Pro Ser Gly Ala Ser Pro Ser Ala Ser Ala Leu
        1380                1385                1390

Thr Leu Gly Leu Ala Thr Ala Pro Ser Leu Ser Ser Ser Gln Thr Pro
        1395                1400                1405

Gly His Pro Leu Leu Ala Pro Thr Ser Ser His Val Pro Gly Leu
        1410                1415                1420

Asn Ser Thr Val Ala Pro Ala Cys Ser Pro Val Leu Val Pro Ala Ser
1425                1430                1435                1440

Ala Leu Ala Ser Pro Phe Pro Ser Ala Pro Asn Pro Ala Pro Ala Gln
            1445                1450                1455

Ala Ser Leu Leu Ala Pro Ala Ser Ser Ala Ser Gln Ala Leu Ala Thr
            1460                1465                1470

Pro Leu Ala Pro Met Ala Ala Pro Gln Thr Ala Ile Leu Ala Pro Ser
        1475                1480                1485

Pro Ala Pro Pro Leu Ala Pro Leu Pro Val Leu Ala Pro Ser Pro Gly
            1490                1495                1500

Ala Ala Pro Val Leu Ala Ser Ser Gln Thr Pro Val Pro Val Met Ala
1505                1510                1515                1520

Pro Ser Ser Thr Pro Gly Thr Ser Leu Ala Ser Ala Ser Pro Val Pro
            1525                1530                1535

Ala Pro Thr Pro Val Leu Ala Pro Ser Ser Thr Gln Thr Met Leu Pro
        1540                1545                1550

Ala Pro Val Pro Ser Pro Leu Pro Ser Pro Ala Ser Thr Gln Thr Leu
            1555                1560                1565

Ala Leu Ala Pro Ala Leu Ala Pro Thr Leu Gly Gly Ser Ser Pro Ser
        1570                1575                1580

Gln Thr Leu Ser Leu Gly Thr Gly Asn Pro Gln Gly Pro Phe Pro Thr
1585                1590                1595                1600

Gln Thr Leu Ser Leu Thr Pro Ala Ser Ser Leu Val Pro Thr Pro Ala
            1605                1610                1615

Gln Thr Leu Ser Leu Ala Pro Gly Pro Pro Leu Gly Pro Thr Gln Thr
        1620                1625                1630

Leu Ser Leu Ala Pro Ala Pro Pro Leu Ala Pro Ala Ser Pro Val Gly
        1635                1640                1645

Pro Ala Pro Ala His Thr Leu Thr Leu Ala Pro Ala Ser Ser Ser Ala
    1650                1655                1660

Ser Leu Leu Ala Pro Ala Ser Val Gln Thr Leu Thr Leu Ser Pro Ala
1665                1670                1675                1680

Pro Val Pro Thr Leu Gly Pro Ala Ala Ala Gln Thr Leu Ala Leu Ala
            1685                1690                1695

Pro Ala Ser Thr Gln Ser Pro Ala Ser Gln Ala Ser Ser Leu Val Val
            1700                1705                1710

Ser Ala Ser Gly Ala Ala Pro Leu Pro Val Thr Met Val Ser Arg Leu
        1715                1720                1725

Pro Val Ser Lys Asp Glu Pro Asp Thr Leu Thr Leu Arg Ser Gly Pro
        1730                1735                1740

Pro Ser Pro Pro Ser Thr Ala Ser Phe Gly Gly Pro Arg Pro Arg
1745                1750                1755                1760

Arg Gln Pro Pro Pro Pro Arg Ser Pro Phe Tyr Leu Asp Ser Leu
            1765                1770                1775

Glu Glu Lys Arg Lys Arg Gln Arg Ser Glu Arg Leu Glu Arg Ile Phe
```

-continued

```
                    1780              1785              1790

Gln Leu Ser Glu Ala His Gly Ala Leu Ala Pro Val Tyr Gly Thr Glu
            1795              1800              1805

Val Leu Asp Phe Cys Thr Leu Pro Gln Pro Val Ala Ser Pro Ile Gly
1810              1815              1820

Pro Arg Ser Pro Gly Pro Ser His Pro Thr Phe Trp Thr Tyr Thr Glu
1825              1830              1835              1840

Ala Ala His Arg Ala Val Leu Phe Pro Gln Gln Arg Leu Asp Gln Leu
            1845              1850              1855

Ser Glu Ile Ile Glu Arg Phe Ile Phe Val Met Pro Pro Val Glu Ala
            1860              1865              1870

Pro Pro Pro Ser Leu His Ala Cys His Pro Pro Trp Leu Ala Pro
        1875              1880              1885

Arg Gln Ala Ala Phe Gln Glu Gln Leu Ala Ser Glu Leu Trp Pro Arg
        1890              1895              1900

Ala Arg Pro Leu His Arg Ile Val Cys Asn Met Arg Thr Gln Phe Pro
1905              1910              1915              1920

Asp Leu Arg Leu Ile Gln Tyr Asp Cys Gly Lys Leu Gln Thr Leu Ala
            1925              1930              1935

Val Leu Leu Arg Gln Leu Lys Ala Glu Gly His Arg Val Leu Ile Phe
            1940              1945              1950

Thr Gln Met Thr Arg Met Leu Asp Val Leu Glu Gln Phe Leu Thr Tyr
            1955              1960              1965

His Gly His Leu Tyr Leu Arg Leu Asp Gly Ser Thr Arg Val Glu Gln
        1970              1975              1980

Arg Gln Ala Leu Met Glu Arg Phe Asn Ala Asp Lys Arg Ile Phe Cys
1985              1990              1995              2000

Phe Ile Leu Ser Thr Arg Ser Gly Gly Val Gly Val Asn Leu Thr Gly
            2005              2010              2015

Ala Asp Thr Val Val Phe Tyr Asp Ser Asp Trp Asn Pro Thr Met Asp
            2020              2025              2030

Ala Gln Ala Gln Asp Arg Cys His Arg Ile Gly Gln Thr Arg Asp Val
            2035              2040              2045

His Ile Tyr Arg Leu Ile Ser Glu Arg Thr Val Glu Glu Asn Ile Leu
        2050              2055              2060

Lys Lys Ala Asn Gln Lys Arg Met Leu Gly Asp Met Ala Ile Glu Gly
2065              2070              2075              2080

Gly Asn Phe Thr Thr Ala Tyr Phe Lys Gln Gln Thr Ile Arg Glu Leu
            2085              2090              2095

Phe Asp Met Pro Leu Glu Glu Pro Ser Ser Ser Val Pro Ser Ala
        2100              2105              2110

Pro Glu Glu Glu Glu Thr Val Ala Ser Lys Gln Thr His Ile Leu
        2115              2120              2125

Glu Gln Ala Leu Cys Arg Ala Glu Asp Glu Glu Asp Ile Arg Ala Ala
        2130              2135              2140

Thr Gln Ala Lys Ala Glu Gln Val Ala Glu Leu Ala Glu Phe Asn Glu
2145              2150              2155              2160

Asn Asp Gly Phe Pro Ala Gly Glu Gly Glu Glu Ala Gly Arg Pro Gly
            2165              2170              2175

Ala Glu Asp Glu Glu Met Ser Arg Ala Glu Gln Glu Ile Ala Ala Leu
            2180              2185              2190

Val Glu Gln Leu Thr Pro Ile Glu Arg Tyr Ala Met Lys Phe Leu Glu
            2195              2200              2205
```

```
Ala Ser Leu Glu Glu Val Ser Arg Glu Glu Leu Lys Gln Ala Glu Glu
    2210                2215                2220

Gln Val Glu Ala Ala Arg Lys Asp Leu Asp Gln Ala Lys Glu Glu Val
2225                2230                2235                2240

Phe Arg Leu Pro Gln Glu Glu Glu Gly Pro Gly Ala Gly Asp Glu
                2245                2250                2255

Ser Ser Cys Gly Thr Gly Gly Thr His Arg Arg Ser Lys Lys Ala
            2260                2265                2270

Lys Ala Pro Glu Arg Pro Gly Thr Arg Val Ser Glu Arg Leu Arg Gly
            2275                2280                2285

Ala Arg Ala Glu Thr Gln Gly Ala Asn His Thr Pro Val Ile Ser Ala
            2290                2295                2300

His Gln Thr Arg Ser Thr Thr Thr Pro Pro Arg Cys Ser Pro Ala Arg
2305                2310                2315                2320

Glu Arg Val Pro Arg Pro Ala Pro Arg Pro Arg Pro Thr Pro Ala Ser
                2325                2330                2335

Ala Pro Ala Ala Ile Pro Ala Leu Val Pro Val Pro Val Ser Ala Pro
            2340                2345                2350

Val Pro Ile Ser Ala Pro Asn Pro Ile Thr Ile Leu Pro Val His Ile
            2355                2360                2365

Leu Pro Ser Pro Pro Pro Ser Gln Ile Pro Pro Cys Ser Ser Pro
    2370                2375                2380

Ala Cys Thr Pro Pro Ala Cys Thr Pro Pro Ala His Thr Pro
2385                2390                2395                2400

Pro Pro Ala Gln Thr Cys Leu Val Thr Pro Ser Ser Pro Leu Leu Leu
                2405                2410                2415

Gly Pro Pro Ser Val Pro Ile Ser Ala Ser Val Thr Asn Leu Pro Leu
            2420                2425                2430

Gly Leu Arg Pro Glu Ala Glu Leu Cys Ala Gln Ala Leu Ala Ser Pro
            2435                2440                2445

Glu Ser Leu Glu Leu Ala Ser Val Ala Ser Ser Glu Thr Ser Ser Leu
    2450                2455                2460

Ser Leu Val Pro Pro Lys Asp Leu Leu Pro Val Ala Val Glu Ile Leu
2465                2470                2475                2480

Pro Val Ser Glu Lys Asn Leu Ser Leu Thr Pro Ser Ala Pro Ser Leu
                2485                2490                2495

Thr Leu Glu Ala Gly Ser Ile Pro Asn Gly Gln Glu Gln Glu Ala Pro
                2500                2505                2510

Asp Ser Ala Glu Gly Thr Thr Leu Thr Val Leu Pro Glu Gly Glu Glu
            2515                2520                2525

Leu Pro Leu Cys Val Ser Glu Ser Asn Gly Leu Glu Leu Pro Pro Ser
    2530                2535                2540

Ala Ala Ser Asp Glu Pro Leu Gln Glu Pro Leu Glu Ala Asp Arg Thr
2545                2550                2555                2560

Ser Glu Glu Leu Thr Glu Ala Lys Thr Pro Thr Ser Ser Pro Glu Lys
                2565                2570                2575

Pro Gln Glu Leu Val Thr Ala Glu Val Ala Ala Pro Ser Thr Ser Ser
                2580                2585                2590

Ser Ala Thr Ser Ser Pro Glu Gly Pro Ser Pro Ala Arg Pro Pro Arg
            2595                2600                2605

Arg Arg Thr Ser Ala Asp Val Glu Ile Arg Gly Gln Gly Thr Gly Arg
            2610                2615                2620
```

-continued

```
Pro Gly Gln Pro Pro Gly Pro Lys Val Leu Arg Lys Leu Pro Gly Arg
2625                2630                2635                2640

Leu Val Thr Val Val Glu Glu Lys Glu Leu Val Gln Arg Arg Arg Gln
            2645                2650                2655

Gln Arg Gly Ala Ala Ser Thr Leu Val Pro Gly Val Ser Glu Thr Ser
        2660                2665                2670

Ala Ser Pro Gly Ser Pro Ser Val Arg Ser Met Ser Gly Pro Glu Ser
    2675                2680                2685

Ser Pro Pro Ile Gly Gly Pro Cys Glu Ala Ala Pro Ser Ser Ser Leu
2690                2695                2700

Pro Thr Pro Pro Gln Gln Pro Phe Ile Ala Arg Arg His Ile Glu Leu
2705                2710                2715                2720

Gly Val Thr Gly Gly Gly Ser Pro Glu Asn Gly Asp Gly Ala Leu Leu
            2725                2730                2735

Ala Ile Thr Pro Pro Ala Val Lys Arg Arg Arg Gly Arg Pro Pro Lys
        2740                2745                2750

Lys Asn Arg Ser Pro Ala Asp Ala Gly Arg Gly Val Asp Glu Ala Pro
    2755                2760                2765

Ser Ser Thr Leu Lys Gly Lys Thr Asn Gly Ala Asp Pro Val Pro Gly
2770                2775                2780

Pro Glu Thr Leu Ile Val Ala Asp Pro Val Leu Glu Pro Gln Leu Ile
2785                2790                2795                2800

Pro Gly Pro Gln Pro Leu Gly Pro Gln Pro Val His Arg Pro Asn Pro
            2805                2810                2815

Leu Leu Ser Pro Val Glu Lys Arg Arg Arg Gly Arg Pro Pro Lys Ala
        2820                2825                2830

Arg Asp Leu Pro Ile Pro Gly Thr Ile Ser Ser Ala Gly Asp Gly Asn
    2835                2840                2845

Ser Glu Ser Arg Thr Gln Pro Pro Pro His Pro Ser Pro Leu Thr Pro
2850                2855                2860

Leu Pro Pro Leu Leu Val Cys Pro Thr Ala Thr Val Ala Asn Thr Val
2865                2870                2875                2880

Thr Thr Val Thr Ile Ser Thr Ser Pro Pro Lys Arg Lys Arg Gly Arg
            2885                2890                2895

Pro Pro Lys Asn Pro Pro Ser Pro Arg Pro Ser Gln Leu Pro Val Leu
        2900                2905                2910

Asp Arg Asp Ser Thr Ser Val Leu Glu Ser Cys Gly Leu Gly Arg Arg
    2915                2920                2925

Arg Gln Pro Gln Gly Gln Gly Glu Ser Glu Gly Ser Ser Ser Asp Glu
2930                2935                2940

Asp Gly Ser Arg Pro Leu Thr Arg Leu Ala Arg Leu Arg Leu Glu Ala
2945                2950                2955                2960

Glu Gly Met Arg Gly Arg Lys Ser Gly Gly Ser Met Val Val Ala Val
            2965                2970                2975

Ile Gln Asp Asp Leu Asp Leu Ala Asp Ser Gly Pro Gly Gly Leu Glu
        2980                2985                2990

Leu Thr Pro Pro Val Val Ser Leu Thr Pro Lys Leu Arg Ser Thr Arg
    2995                3000                3005

Leu Arg Pro Gly Ser Leu Val Pro Pro Leu Glu Thr Glu Lys Leu Pro
3010                3015                3020

Arg Lys Arg Ala Gly Ala Pro Val Gly Gly Ser Pro Gly Leu Ala Lys
3025                3030                3035                3040

Arg Gly Arg Leu Gln Pro Pro Ser Pro Leu Gly Pro Glu Gly Ser Val
```

-continued

```
                    3045                3050                3055
Glu Glu Ser Glu Ala Glu Ala Ser Gly Glu Glu Glu Gly Asp Gly
            3060                3065                3070

Thr Pro Arg Arg Pro Gly Pro Arg Leu Val Gly Thr Thr Asn
        3075                3080                3085

Gln Gly Asp Gln Arg Ile Leu Arg Ser Ser Ala Pro Pro Ser Leu Ala
        3090                3095                3100

Gly Pro Ala Val Ser His Arg Gly Arg Lys Ala Lys Thr Glx
3105                3110                3115
```

<210> SEQ ID NO 2
<211> LENGTH: 2972
<212> TYPE: PRT
<213> ORGANISM: Human

<400> SEQUENCE: 2

```
Met Ala Lys Asp Val Arg Gln Phe Trp Ser Asn Val Glu Lys Val Val
1               5                   10                  15

Gln Phe Lys Gln Gln Ser Arg Leu Glu Glu Lys Arg Lys Lys Ala Leu
            20                  25                  30

Asp Leu His Leu Asp Phe Ile Val Gly Gln Thr Glu Lys Tyr Ser Asp
        35                  40                  45

Leu Leu Ser Gln Ser Leu Asn Gln Pro Leu Thr Ser Ser Lys Ala Gly
    50                  55                  60

Ser Ser Pro Cys Leu Gly Ser Ser Ala Ala Ser Ser Pro Pro Pro
65                  70                  75                  80

Pro Ala Ser Arg Leu Asp Asp Glu Asp Gly Asp Phe Gln Pro Gln Glu
            85                  90                  95

Asp Glu Glu Glu Asp Asp Glu Thr Ile Glu Val Glu Glu Gln Gln
        100                 105                 110

Glu Gly Asn Asp Ala Glu Ala Gln Arg Arg Glu Ile Glu Leu Leu Arg
    115                 120                 125

Arg Glu Gly Glu Leu Pro Leu Glu Glu Leu Leu Arg Ser Leu Pro Pro
130                 135                 140

Gln Leu Leu Glu Gly Pro Ser Ser Pro Ser Gln Thr Pro Ser Ser His
145                 150                 155                 160

Asp Ser Asp Thr Arg Asp Gly Pro Glu Glu Gly Ala Glu Glu Pro
            165                 170                 175

Pro Gln Val Leu Glu Ile Lys Pro Pro Ser Ala Val Thr Gln Arg
        180                 185                 190

Asn Lys Gln Pro Trp His Pro Asp Glu Asp Glu Glu Phe Thr Ala
        195                 200                 205

Asn Glu Glu Glu Ala Glu Asp Glu Asp Thr Ile Ala Ala Glu Glu
    210                 215                 220

Gln Leu Glu Gly Glu Val Asp His Ala Met Glu Leu Ser Glu Leu Ala
225                 230                 235                 240

Arg Glu Gly Glu Leu Ser Met Glu Glu Leu Leu Gln Gln Tyr Ala Gly
            245                 250                 255

Ala Tyr Ala Pro Gly Ser Gly Ser Ser Glu Asp Glu Asp Glu Asp Glu
        260                 265                 270

Val Asp Ala Asn Ser Ser Asp Cys Glu Pro Glu Gly Pro Val Glu Ala
        275                 280                 285

Glu Glu Pro Pro Gln Glu Asp Ser Ser Gln Ser Asp Ser Val Glu
    290                 295                 300
```

-continued

```
Asp Arg Ser Glu Asp Glu Glu Asp Glu His Ser Glu Glu Glu Thr
305                 310                 315                 320

Ser Gly Ser Ser Ala Ser Glu Ser Glu Ser Glu Ser Glu Ser Glu Asp
            325                 330                 335

Ala Gln Ser Gln Ser Gln Ala Asp Glu Glu Glu Asp Asp Asp Phe
            340                 345                 350

Gly Val Glu Tyr Leu Leu Ala Arg Asp Glu Glu Gln Ser Glu Ala Asp
            355                 360                 365

Ala Gly Ser Gly Pro Pro Thr Pro Gly Pro Thr Thr Leu Gly Pro Lys
370                 375                 380

Lys Glu Ile Thr Asp Ile Ala Ala Ala Glu Ser Leu Gln Pro Lys
385                 390                 395                 400

Gly Tyr Thr Leu Ala Thr Thr Gln Val Lys Thr Pro Ile Pro Leu Leu
                405                 410                 415

Leu Arg Gly Gln Leu Arg Glu Tyr Gln His Ile Gly Leu Asp Trp Leu
            420                 425                 430

Val Thr Met Tyr Glu Lys Lys Leu Asn Gly Ile Leu Ala Asp Glu Met
            435                 440                 445

Gly Leu Gly Lys Thr Ile Gln Thr Ile Ser Leu Leu Ala His Leu Ala
450                 455                 460

Cys Glu Lys Gly Asn Trp Gly Pro His Leu Ile Ile Val Pro Thr Ser
465                 470                 475                 480

Val Met Leu Asn Trp Glu Met Glu Leu Lys Arg Trp Cys Pro Ser Phe
            485                 490                 495

Lys Ile Leu Thr Tyr Tyr Gly Ala Gln Lys Glu Arg Lys Leu Lys Arg
            500                 505                 510

Gln Gly Trp Thr Lys Pro Asn Ala Phe His Val Cys Ile Thr Ser Tyr
            515                 520                 525

Lys Leu Val Leu Gln Asp His Gln Ala Phe Arg Arg Lys Asn Trp Arg
            530                 535                 540

Tyr Leu Ile Leu Asp Glu Ala Gln Asn Ile Lys Asn Phe Lys Ser Gln
545                 550                 555                 560

Arg Trp Gln Ser Leu Leu Asn Phe Asn Ser Gln Arg Arg Leu Leu Leu
            565                 570                 575

Thr Gly Thr Pro Leu Gln Asn Ser Leu Met Glu Leu Trp Ser Leu Met
            580                 585                 590

His Phe Leu Met Pro His Val Phe Gln Ser His Arg Glu Phe Lys Glu
            595                 600                 605

Trp Phe Ser Asn Pro Leu Thr Gly Met Ile Glu Gly Ser Gln Glu Tyr
610                 615                 620

Asn Glu Gly Leu Val Lys Arg Leu His Lys Val Leu Arg Pro Phe Leu
625                 630                 635                 640

Leu Arg Arg Val Lys Val Asp Val Glu Lys Gln Met Pro Lys Lys Tyr
            645                 650                 655

Glu His Val Ile Arg Cys Arg Leu Ser Lys Arg Gln Arg Cys Leu Tyr
            660                 665                 670

Asp Asp Phe Met Ala Gln Thr Thr Lys Glu Thr Leu Ala Thr Gly
            675                 680                 685

His Phe Met Ser Val Ile Asn Ile Leu Met Gln Leu Arg Lys Val Cys
            690                 695                 700

Asn His Pro Asn Leu Phe Asp Pro Arg Pro Val Thr Ser Pro Phe Ile
705                 710                 715                 720

Thr Pro Gly Ile Cys Phe Ser Thr Ala Ser Leu Val Leu Arg Ala Thr
```

```
                    725                 730                 735
Asp Val His Pro Leu Gln Arg Ile Asp Met Gly Arg Phe Asp Leu Ile
                740                 745                 750
Gly Leu Glu Gly Arg Val Ser Arg Tyr Glu Ala Asp Thr Phe Leu Pro
            755                 760                 765
Arg His Arg Leu Ser Arg Arg Val Leu Leu Glu Val Ala Thr Ala Pro
        770                 775                 780
Asp Pro Pro Arg Pro Lys Pro Val Lys Met Lys Val Asn Arg Met
785                 790                 795                 800
Leu Gln Pro Val Pro Lys Gln Glu Gly Arg Thr Val Val Val Asn
                805                 810                 815
Asn Pro Arg Ala Pro Leu Gly Pro Val Pro Val Arg Pro Pro Gly
            820                 825                 830
Pro Glu Leu Ser Ala Gln Pro Thr Pro Gly Pro Val Pro Gln Val Leu
        835                 840                 845
Pro Ala Ser Leu Met Val Ser Ala Ser Pro Ala Gly Pro Pro Leu Ile
850                 855                 860
Pro Ala Ser Arg Pro Pro Gly Pro Val Leu Leu Pro Pro Leu Gln Pro
865                 870                 875                 880
Asn Ser Gly Ser Leu Pro Gln Val Leu Pro Ser Pro Leu Gly Val Leu
                885                 890                 895
Ser Gly Thr Ser Arg Pro Pro Thr Pro Thr Leu Ser Leu Lys Pro Thr
            900                 905                 910
Pro Pro Ala Pro Val Arg Leu Ser Pro Ala Pro Pro Gly Ser Ser
        915                 920                 925
Ser Leu Leu Lys Pro Leu Thr Val Pro Pro Gly Tyr Thr Phe Pro Pro
    930                 935                 940
Ala Ala Ala Thr Thr Thr Ser Thr Thr Thr Ala Thr Ala Thr Thr
945                 950                 955                 960
Ala Val Pro Ala Pro Thr Pro Ala Pro Gln Arg Leu Ile Leu Ser Pro
                965                 970                 975
Asp Met Gln Ala Arg Leu Pro Ser Gly Glu Val Val Ser Ile Gly Gln
            980                 985                 990
Leu Ala Ser Leu Ala Gln Arg Pro Val Ala Asn Ala Gly Gly Ser Lys
        995                 1000                1005
Pro Leu Thr Phe Gln Ile Gln Gly Asn Lys Leu Thr Leu Thr Gly Ala
    1010                1015                1020
Gln Val Arg Gln Leu Ala Val Gly Gln Pro Arg Pro Leu Gln Met Pro
1025                1030                1035                1040
Pro Thr Met Val Asn Asn Thr Gly Val Val Lys Ile Val Val Arg Gln
                1045                1050                1055
Ala Pro Arg Asp Gly Leu Thr Pro Val Pro Leu Ala Pro Ala Pro
            1060                1065                1070
Arg Pro Pro Ser Ser Gly Leu Pro Ala Val Leu Asn Pro Arg Pro Thr
        1075                1080                1085
Leu Thr Pro Gly Arg Leu Pro Thr Pro Thr Leu Gly Thr Ala Arg Ala
    1090                1095                1100
Pro Met Pro Thr Pro Thr Leu Val Arg Pro Leu Leu Lys Leu Val His
1105                1110                1115                1120
Ser Pro Ser Pro Glu Val Ser Ala Ser Ala Pro Gly Ala Ala Pro Leu
                1125                1130                1135
Thr Ile Ser Ser Pro Leu His Val Pro Ser Ser Leu Pro Gly Pro Ala
            1140                1145                1150
```

```
Ser Ser Pro Met Pro Ile Pro Asn Ser Ser Pro Leu Ala Ser Pro Val
        1155                1160                1165

Ser Ser Thr Val Ser Val Pro Leu Ser Ser Leu Pro Ile Ser Val
    1170                1175                1180

Pro Thr Thr Leu Pro Ala Pro Ala Ser Ala Pro Leu Thr Ile Pro Ile
1185                1190                1195                1200

Ser Ala Pro Leu Thr Val Ser Ala Ser Gly Pro Ala Leu Leu Thr Ser
            1205                1210                1215

Val Thr Pro Pro Leu Ala Pro Val Val Pro Ala Ala Pro Gly Pro Pro
            1220                1225                1230

Ser Leu Gln Pro Ser Gly Ala Ser Pro Ser Ala Ser Ala Leu Thr Leu
        1235                1240                1245

Gly Leu Ala Thr Ala Pro Ser Leu Ser Ser Ser Gln Thr Pro Gly His
    1250                1255                1260

Pro Leu Leu Leu Ala Pro Thr Ser Ser His Val Pro Gly Leu Asn Ser
1265                1270                1275                1280

Thr Val Ala Pro Ala Cys Ser Pro Val Leu Val Pro Ala Ser Ala Leu
            1285                1290                1295

Ala Ser Pro Phe Pro Ser Ala Pro Asn Pro Ala Pro Ala Gln Ala Ser
        1300                1305                1310

Leu Leu Ala Pro Ala Ser Ser Ala Ser Gln Ala Leu Ala Thr Pro Leu
        1315                1320                1325

Ala Pro Met Ala Ala Pro Gln Thr Ala Ile Leu Ala Pro Ser Pro Ala
    1330                1335                1340

Pro Pro Leu Ala Pro Leu Pro Val Leu Ala Pro Ser Pro Gly Ala Ala
1345                1350                1355                1360

Pro Val Leu Ala Ser Ser Gln Thr Pro Val Pro Val Met Ala Pro Ser
            1365                1370                1375

Ser Thr Pro Gly Thr Ser Leu Ala Ser Ala Ser Pro Val Pro Ala Pro
            1380                1385                1390

Thr Pro Val Leu Ala Pro Ser Ser Thr Gln Thr Met Leu Pro Ala Pro
    1395                1400                1405

Val Pro Ser Pro Leu Pro Ser Pro Ala Ser Thr Gln Thr Leu Ala Leu
    1410                1415                1420

Ala Pro Ala Leu Ala Pro Thr Leu Gly Gly Ser Ser Pro Ser Gln Thr
1425                1430                1435                1440

Leu Ser Leu Gly Thr Gly Asn Pro Gln Gly Pro Phe Pro Thr Gln Thr
            1445                1450                1455

Leu Ser Leu Thr Pro Ala Ser Ser Leu Val Pro Thr Pro Ala Gln Thr
            1460                1465                1470

Leu Ser Leu Ala Pro Gly Pro Pro Leu Gly Pro Thr Gln Thr Leu Ser
        1475                1480                1485

Leu Ala Pro Ala Pro Pro Leu Ala Pro Ala Ser Pro Val Gly Pro Ala
    1490                1495                1500

Pro Ala His Thr Leu Thr Leu Ala Pro Ala Ser Ser Ser Ala Ser Leu
1505                1510                1515                1520

Leu Ala Pro Ala Ser Val Gln Thr Leu Thr Leu Ser Pro Ala Pro Val
            1525                1530                1535

Pro Thr Leu Gly Pro Ala Ala Ala Gln Thr Leu Ala Leu Ala Pro Ala
            1540                1545                1550

Ser Thr Gln Ser Pro Ala Ser Gln Ala Ser Ser Leu Val Val Ser Ala
        1555                1560                1565
```

-continued

```
Ser Gly Ala Ala Pro Leu Pro Val Thr Met Val Ser Arg Leu Pro Val
    1570                1575                1580

Ser Lys Asp Glu Pro Asp Thr Leu Thr Leu Arg Ser Gly Pro Pro Ser
1585                1590                1595                1600

Pro Pro Ser Thr Ala Thr Ser Phe Gly Gly Pro Arg Pro Arg Arg Gln
        1605                1610                1615

Pro Pro Pro Pro Pro Arg Ser Pro Phe Tyr Leu Asp Ser Leu Glu Glu
        1620                1625                1630

Lys Arg Lys Arg Gln Arg Ser Glu Arg Leu Glu Arg Ile Phe Gln Leu
        1635                1640                1645

Ser Glu Ala His Gly Ala Leu Ala Pro Val Tyr Gly Thr Glu Val Leu
        1650                1655                1660

Asp Phe Cys Thr Leu Pro Gln Pro Val Ala Ser Pro Ile Gly Pro Arg
1665                1670                1675                1680

Ser Pro Gly Pro Ser His Pro Thr Phe Trp Thr Tyr Thr Glu Ala Ala
        1685                1690                1695

His Arg Ala Val Leu Phe Pro Gln Gln Arg Leu Asp Gln Leu Ser Glu
        1700                1705                1710

Ile Ile Glu Arg Phe Ile Phe Val Met Pro Pro Val Glu Ala Pro Pro
        1715                1720                1725

Pro Ser Leu His Ala Cys His Pro Pro Trp Leu Ala Pro Arg Gln
    1730                1735                1740

Ala Ala Phe Gln Glu Gln Leu Ala Ser Glu Leu Trp Pro Arg Ala Arg
1745                1750                1755                1760

Pro Leu His Arg Ile Val Cys Asn Met Arg Thr Gln Phe Pro Asp Leu
        1765                1770                1775

Arg Leu Ile Gln Tyr Asp Cys Gly Lys Leu Gln Thr Leu Ala Val Leu
        1780                1785                1790

Leu Arg Gln Leu Lys Ala Glu Gly His Arg Val Leu Ile Phe Thr Gln
        1795                1800                1805

Met Thr Arg Met Leu Asp Val Leu Glu Gln Phe Leu Thr Tyr His Gly
    1810                1815                1820

His Leu Tyr Leu Arg Leu Asp Gly Ser Thr Arg Val Glu Gln Arg Gln
1825                1830                1835                1840

Ala Leu Met Glu Arg Phe Asn Ala Asp Lys Arg Ile Phe Cys Phe Ile
        1845                1850                1855

Leu Ser Thr Arg Ser Gly Gly Val Gly Val Asn Leu Thr Gly Ala Asp
        1860                1865                1870

Thr Val Val Phe Tyr Asp Ser Asp Trp Asn Pro Thr Met Asp Ala Gln
        1875                1880                1885

Ala Gln Asp Arg Cys His Arg Ile Gly Gln Thr Arg Asp Val His Ile
    1890                1895                1900

Tyr Arg Leu Ile Ser Glu Arg Thr Val Glu Glu Asn Ile Leu Lys Lys
1905                1910                1915                1920

Ala Asn Gln Lys Arg Met Leu Gly Asp Met Ala Ile Glu Gly Gly Asn
        1925                1930                1935

Phe Thr Thr Ala Tyr Phe Lys Gln Gln Thr Ile Arg Glu Leu Phe Asp
        1940                1945                1950

Met Pro Leu Glu Glu Pro Ser Ser Ser Val Pro Ser Ala Pro Glu
    1955                1960                1965

Glu Glu Glu Glu Thr Val Ala Ser Lys Gln Thr His Ile Leu Glu Gln
    1970                1975                1980

Ala Leu Cys Arg Ala Glu Asp Glu Glu Asp Ile Arg Ala Ala Thr Gln
```

-continued

```
1985                1990                1995                2000
Ala Lys Ala Glu Gln Val Ala Glu Leu Ala Glu Phe Asn Glu Asn Asp
            2005                2010                2015
Gly Phe Pro Ala Gly Glu Gly Glu Ala Gly Arg Pro Gly Ala Glu
        2020                2025                2030
Asp Glu Glu Met Ser Arg Ala Glu Gln Glu Ile Ala Ala Leu Val Glu
    2035                2040                2045
Gln Leu Thr Pro Ile Glu Arg Tyr Ala Met Lys Phe Leu Glu Ala Ser
  2050                2055                2060
Leu Glu Glu Val Ser Arg Glu Glu Leu Lys Gln Ala Glu Glu Gln Val
2065                2070                2075                2080
Glu Ala Ala Arg Lys Asp Leu Asp Gln Ala Lys Glu Glu Val Phe Arg
        2085                2090                2095
Leu Pro Gln Glu Glu Glu Glu Gly Pro Gly Ala Gly Asp Glu Ser Ser
            2100                2105                2110
Cys Gly Thr Gly Gly Thr His Arg Arg Ser Lys Lys Ala Lys Ala
        2115                2120                2125
Pro Glu Arg Pro Gly Thr Arg Val Ser Glu Arg Leu Arg Gly Ala Arg
    2130                2135                2140
Ala Glu Thr Gln Gly Ala Asn His Thr Pro Val Ile Ser Ala His Gln
2145                2150                2155                2160
Thr Arg Ser Thr Thr Thr Pro Pro Arg Cys Ser Pro Ala Arg Glu Arg
            2165                2170                2175
Val Pro Arg Pro Ala Pro Arg Pro Arg Pro Thr Pro Ala Ser Ala Pro
        2180                2185                2190
Ala Ala Ile Pro Ala Leu Val Pro Val Pro Val Ser Ala Pro Val Pro
    2195                2200                2205
Ile Ser Ala Pro Asn Pro Ile Thr Ile Leu Pro Val His Ile Leu Pro
        2210                2215                2220
Ser Pro Pro Pro Ser Gln Ile Pro Pro Cys Ser Ser Pro Ala Cys
2225                2230                2235                2240
Thr Pro Pro Pro Ala Cys Thr Pro Pro Pro Ala His Thr Pro Pro Pro
            2245                2250                2255
Ala Gln Thr Cys Leu Val Thr Pro Ser Ser Pro Leu Leu Leu Gly Pro
        2260                2265                2270
Pro Ser Val Pro Ile Ser Ala Ser Val Thr Asn Leu Pro Leu Gly Leu
    2275                2280                2285
Arg Pro Glu Ala Glu Leu Cys Ala Gln Ala Leu Ala Ser Pro Glu Ser
    2290                2295                2300
Leu Glu Leu Ala Ser Val Ala Ser Ser Glu Thr Ser Ser Leu Ser Leu
2305                2310                2315                2320
Val Pro Pro Lys Asp Leu Leu Pro Val Ala Val Glu Ile Leu Pro Val
            2325                2330                2335
Ser Glu Lys Asn Leu Ser Leu Thr Pro Ser Ala Pro Ser Leu Thr Leu
        2340                2345                2350
Glu Ala Gly Ser Ile Pro Asn Gly Gln Glu Gln Glu Ala Pro Asp Ser
    2355                2360                2365
Ala Glu Gly Thr Thr Leu Thr Val Leu Pro Glu Gly Glu Glu Leu Pro
    2370                2375                2380
Leu Cys Val Ser Glu Ser Asn Gly Leu Glu Leu Pro Pro Ser Ala Ala
2385                2390                2395                2400
Ser Asp Glu Pro Leu Gln Glu Pro Leu Glu Ala Asp Arg Thr Ser Glu
            2405                2410                2415
```

-continued

```
Glu Leu Thr Glu Ala Lys Thr Pro Thr Ser Ser Pro Glu Lys Pro Gln
        2420                2425                2430

Glu Leu Val Thr Ala Glu Val Ala Ala Pro Ser Thr Ser Ser Ser Ala
        2435                2440                2445

Thr Ser Ser Pro Glu Gly Pro Ser Pro Ala Arg Pro Pro Arg Arg Arg
        2450                2455                2460

Thr Ser Ala Asp Val Glu Ile Arg Gly Gln Gly Thr Gly Arg Pro Gly
2465                2470                2475                2480

Gln Pro Pro Gly Pro Lys Val Leu Arg Lys Leu Pro Gly Arg Leu Val
            2485                2490                2495

Thr Val Val Glu Glu Lys Glu Leu Val Gln Arg Arg Arg Gln Gln Arg
        2500                2505                2510

Gly Ala Ala Ser Thr Leu Val Pro Gly Val Ser Glu Thr Ser Ala Ser
        2515                2520                2525

Pro Gly Ser Pro Ser Val Arg Ser Met Ser Gly Pro Glu Ser Ser Pro
        2530                2535                2540

Pro Ile Gly Gly Pro Cys Glu Ala Ala Pro Ser Ser Ser Leu Pro Thr
2545                2550                2555                2560

Pro Pro Gln Gln Pro Phe Ile Ala Arg Arg His Ile Glu Leu Gly Val
            2565                2570                2575

Thr Gly Gly Gly Ser Pro Glu Asn Gly Asp Gly Ala Leu Leu Ala Ile
        2580                2585                2590

Thr Pro Pro Ala Val Lys Arg Arg Arg Gly Arg Pro Pro Lys Lys Asn
        2595                2600                2605

Arg Ser Pro Ala Asp Ala Gly Arg Gly Val Asp Glu Ala Pro Ser Ser
        2610                2615                2620

Thr Leu Lys Gly Lys Thr Asn Gly Ala Asp Pro Val Pro Gly Pro Glu
2625                2630                2635                2640

Thr Leu Ile Val Ala Asp Pro Val Leu Glu Pro Gln Leu Ile Pro Gly
            2645                2650                2655

Pro Gln Pro Leu Gly Pro Gln Pro Val His Arg Pro Asn Pro Leu Leu
        2660                2665                2670

Ser Pro Val Glu Lys Arg Arg Arg Gly Arg Pro Pro Lys Ala Arg Asp
        2675                2680                2685

Leu Pro Ile Pro Gly Thr Ile Ser Ser Ala Gly Asp Gly Asn Ser Glu
        2690                2695                2700

Ser Arg Thr Gln Pro Pro His Pro Ser Pro Leu Thr Pro Leu Pro
2705                2710                2715                2720

Pro Leu Leu Val Cys Pro Thr Ala Thr Val Ala Asn Thr Val Thr Thr
            2725                2730                2735

Val Thr Ile Ser Thr Ser Pro Lys Arg Lys Arg Gly Arg Pro Pro
        2740                2745                2750

Lys Asn Pro Pro Ser Pro Arg Pro Ser Gln Leu Pro Val Leu Asp Arg
        2755                2760                2765

Asp Ser Thr Ser Val Leu Glu Ser Cys Gly Leu Gly Arg Arg Arg Gln
        2770                2775                2780

Pro Gln Gly Gln Gly Glu Ser Glu Gly Ser Ser Ser Asp Glu Asp Gly
2785                2790                2795                2800

Ser Arg Pro Leu Thr Arg Leu Ala Arg Leu Arg Leu Glu Ala Glu Gly
            2805                2810                2815

Met Arg Gly Arg Lys Ser Gly Gly Ser Met Val Val Ala Val Ile Gln
        2820                2825                2830
```

-continued

```
Asp Asp Leu Asp Leu Ala Asp Ser Gly Pro Gly Gly Leu Glu Leu Thr
            2835                2840                2845
Pro Pro Val Val Ser Leu Thr Pro Lys Leu Arg Ser Thr Arg Leu Arg
        2850                2855                2860
Pro Gly Ser Leu Val Pro Leu Glu Thr Glu Lys Leu Pro Arg Lys
2865                2870                2875                2880
Arg Ala Gly Ala Pro Val Gly Gly Ser Pro Gly Leu Ala Lys Arg Gly
            2885                2890                2895
Arg Leu Gln Pro Pro Ser Pro Leu Gly Pro Glu Gly Ser Val Glu Glu
            2900                2905                2910
Ser Glu Ala Glu Ala Ser Gly Glu Glu Glu Glu Gly Asp Gly Thr Pro
            2915                2920                2925
Arg Arg Arg Pro Gly Pro Arg Arg Leu Val Gly Thr Thr Asn Gln Gly
    2930                2935                2940
Asp Gln Arg Ile Leu Arg Ser Ser Ala Pro Pro Ser Leu Ala Gly Pro
2945                2950                2955                2960
Ala Val Ser His Arg Gly Arg Lys Ala Lys Thr Glx
            2965                2970

<210> SEQ ID NO 3
<211> LENGTH: 12
<212> TYPE: PRT
<213> ORGANISM: Human

<400> SEQUENCE: 3

Gly Ile Leu Ala Asp Glu Met Gly Leu Gly Lys Thr
1               5                   10

<210> SEQ ID NO 4
<211> LENGTH: 12
<212> TYPE: PRT
<213> ORGANISM: Human

<400> SEQUENCE: 4

Leu Ile Ile Val Pro Thr Ser Val Met Leu Asn Trp
1               5                   10

<210> SEQ ID NO 5
<211> LENGTH: 14
<212> TYPE: PRT
<213> ORGANISM: Human

<400> SEQUENCE: 5

Trp Arg Tyr Leu Ile Leu Asp Glu Ala Gln Asn Ile Lys Asn
1               5                   10

<210> SEQ ID NO 6
<211> LENGTH: 22
<212> TYPE: PRT
<213> ORGANISM: Human

<400> SEQUENCE: 6

Arg Leu Leu Leu Thr Gly Thr Pro Leu Gln Asn Ser Leu Met Glu Leu
1               5                   10                  15
Trp Ser Leu Met His Phe
            20

<210> SEQ ID NO 7
<211> LENGTH: 11
<212> TYPE: PRT
<213> ORGANISM: Human
```

<400> SEQUENCE: 7

Phe Leu Leu Arg Arg Val Lys Val Asp Val Glu
 1               5                  10

<210> SEQ ID NO 8
<211> LENGTH: 29
<212> TYPE: PRT
<213> ORGANISM: Human

<400> SEQUENCE: 8

Phe Ile Leu Ser Thr Arg Ser Gly Val Gly Leu Asn Leu Thr Gly
 1               5                  10                  15

Ala Asp Thr Val Val Phe Tyr Asp Ser Asp Trp Asn Pro
            20                  25

<210> SEQ ID NO 9
<211> LENGTH: 22
<212> TYPE: PRT
<213> ORGANISM: Human

<400> SEQUENCE: 9

Asp Ala Gln Ala Gln Asp Arg Cys His Arg Ile Gly Gln Thr Arg Asp
 1               5                  10                  15

Val His Ile Tyr Arg Leu
            20

<210> SEQ ID NO 10
<211> LENGTH: 9354
<212> TYPE: DNA
<213> ORGANISM: Human

<400> SEQUENCE: 10

```
gctcaagatt cctcactgga tggacctcca ggcccccag  atggtgccac agtgcccctg       60
gaggggttca gcttatccca ggctgctgac ctggctaaca agggcccgaa gtgggagaag      120
agccatgccg aaattgcaga acaggccaag catgaggccg atcgagac  tcggattgct       180
gagctgcgga aggagggttt ctggtcactg aagaggctgc taaggtgcc  agagccccct      240
cgccccaaag gtcactggga ctatttgtgc gaagagatgc agtggctctc tgctgacttt      300
gctcaggagc gccgttggaa acggggtgtg gcccggaagg tggtgcgcat ggtgatccgg      360
caccacgagg agcagcggca gaaagaggaa cgggcccgga gggaggagca ggccaagctg      420
cgtcgaattg cttccaccat ggccaaggat gtcaggcagt tctggagcaa tgtggagaag      480
gtggtgcaat tcaagcaaca gtcccggctt gaggaaaagc gcaaaaaagc cctgaccctg      540
catttggact tcattgtggg gcaaactgaa agtactcgg  accttctgtc tcagagcctc      600
aaccagccat taacctccag caaagcaggc tcttcccctt gctcggctc  ttcctcagct      660
gcctccagtc ctccaccccc tgcttctcgc ctggatgatg aagatgggga ctttcaaccc      720
caagaggatg aggaagagga tgatgaggaa acgattgaag ttgaagaaca acaggaaggc      780
aatgatgcag aggcccagag gcgtgagatt gagctgcttc gccgtgaggg agaattgcca      840
ctggaagagc tgctccgttc ccttcccct  cagctgttgg aagggccttc cagccctct      900
caaaccccct catctcatga tagtgacacc cgagatgggc tgaagaagg  tgctgaagaa      960
gagccccctc aggtgttgga gataaagccc ccaccctctg ctgtcacaca gcgcaacaaa     1020
cagccttggc atccagatga agatgatgaa agttttacg  ccaacgaaga ggaagcggag     1080
gatgaagagg atactatagc agctgaggaa cagttggaag gggaggtgga tcatgccatg     1140
```

-continued

```
gagctgagcg agttggctcg agaaggtgag ctttccatgg aggagctatt gcagcagtat    1200
gcaggagcct atgccccagg ctctgggagc agtgaagatg aggatgaaga tgaggttgat    1260
gctaatagct ctgactgtga accagagggg cccgtggaag cggaagagcc tcctcaggag    1320
gatagtagca gtcagtcaga ctctgtggag gaccggagtg aggatgagga agatgaacat    1380
tcagaggagg aagaaacaag tggaagttca gcatcagagg aatctgagtc tgaagagtct    1440
gaggatgccc aatcacagag ccaagcagat gaagaggagg aagatgatga ttttggggtg    1500
gagtacttgc ttgccaggga tgaagagcag agtgaggcag atgcaggcag tgggcctcct    1560
actccagggc ccactactct aggtccaaag aaagaaatta ctgacattgc tgcagcagct    1620
gaaagtctcc agcccaaggg ttacacgctg ccacgaccc aggtaaagac gcccattccc     1680
ctgcttctgc ggggccagct ccgggagtac cagcacattg gctagactg ctggttacc      1740 atgtatgaga agaagcttaa tggcattctt gctgatgaga tggggcttgg aagaccatc     1800 cagaccatct ctctgcttgc ccacttggct tgtgagaaag gtaactgggg tccccattta    1860
atcattgttc ccaccagcgt gatgttgaac tgggagatga agttgaaacg ttggtgcccc    1920
agctttaaaa tcctcactta ctatggagcc cagaaagaga ggaagctcaa gcggcagggc    1980
tggaccaagc ccaatgcctt tcatgtgtgt atcacatctt acaagctggt gctgcaggac    2040
caccaggcct tccgtcgcaa gaactggcgc tatctcattc tggatgaggc gcagaacatc    2100
aagaacttca gtcacagcg ctggcagtca ctcctcaact tcaacagcca gagacgcctg     2160
ctcctgacag gaactccctt gcagaacagc ctcatggagc tgtggtcctt gatgcacttt    2220
ttgatgcccc atgtcttcca gtctcatcgc gagttcaagg agtggttctc taatcccta    2280 actggcatga ttgagggcag ccaagagtat aatgaaggtc tagtcaaacg cctccacaag    2340
gttttgaggc cttttttact gcgccgagtt aaggtggatg ttgagaagca gatgcccaaa    2400
aagtacgagc atgttatccg ctgcaggctc tccaagcgtc aacgctgtct ctatgatgac    2460
ttcatggcac agaccacaac taaggagaca ctagccacag gccatttcat gagcgtcatc    2520
aacattttga tgcagctgag aaaagtttgc aatcatccaa atctgttcga ccctcgaccg    2580
gttacctccc ctttcatcac cccaggcatc tgcttcagca ccgcctctct ggtgctaagg    2640
gccacggatg tccatcccct ccagcggata gacatgggtc gatttgacct tattggcctg    2700
gaaggtcgtg tctctcgata tgaggcagac acatttctgc cccggcaccg cctctctcgc    2760
cgggtactgt tagaagtggc tactgctcct gacccccac cccggcccaa gccagtcaag    2820
atgaaggtca acaggatgct gcagccagta cctaagcaag aaggccggac agtggtggtg    2880
gtgaacaacc cacgggcgcc cctgggccct gtcccagttc gacctcctcc aggtcctgag    2940
ctctcagccc agcccacccc tggcccagtc cccaagtgc tgccagcatc actgatggtt     3000
tcagcctcac ctgccgggcc cccgcttatt cctgcatctc ggcctcctgg ccctgtcctc    3060
ttgcctccac tgcagcccaa cagtggttct ctccccagg tgttgccatc ccccctgggg     3120
gtcctgagtg ggacctcacg gcctccacg ccaaccttgt ccctaaagcc aacaccacct     3180
gccccagttc gcctgagccc agccccacct ccaggctcct ctagcctgtt gaagcccctg    3240
acagtgccca caggctacac cttccctcct gctgctgcca ccaccttc taccaccacg      3300 gcaactgcta ccaccacagc agtgccagct ccgactcctg caccacagcg cctcattcta    3360
tctcccgata tgcaggctcg cctgccctca ggcgaagtgg tcagcatcgg gcagttagcc    3420
tcactggcac aacgtccagt ggctaatgca gggggaagca aacctctcac cttccaaatc    3480
```

```
caggqcaaca agctgacttt gactggtgcc caggtgcgcc agcttgctgt ggggcagccc    3540
cgcccgctgc aaatgccacc aaccatggtg aataatacag gcgtggtgaa gattgtagtg    3600
agacaagccc ctcgggatgg actgactcct gttcctccat ggccccagc accccggcct     3660
ccgagctctg ggcttccagc tgtgttgaat ccacgcccca cgttaacccc tggccggcta    3720
cccacaccta ctctgggtac tgctcgagcc cccatgccca cacccactct ggtgaggcct    3780
cttctcaagc tggtccacag tccttcacct gaagtcagtg cttcagcccc cggagctgcc    3840
cccttgacca tctcttctcc tctccacgtg ccatcctcac tccctgggcc agcctcttct    3900
ccaatgccaa ttcccaactc ctctcccctt gctagtcctg tgtcctctac agtctcagtt    3960
ccattgtcat cttcactccc catctctgtc cccaccacac ttcctgcccc agcctcggct    4020
ccactcacca tccccatctc agccccttg actgtttctg cttcgggccc agctctgttg     4080
accagtgtga ctccaccatt ggcacctgtt gtcccagcgg ctcctggacc tcctccttg     4140
cagccatctg gtgcttcccc gtcagcatca gccttgactc taggtttggc cacagctcca    4200
tccctgtctt catctcagac acctggtcac cctctgttgt tggctcccac ctcttcacat    4260
gttccagggt tgaactcaac cgtggcccca gcatgctcac ctgtcctggt gccagcttcg    4320
gctctggcca gtccttttcc gtcagcacca aatccagctc cagctcaggc ttcccttctg    4380
gctccagcat cttctgcatc tcaggctcta gccacccctc tggctcctat ggcggctcca    4440
cagacagcaa ttctggctcc ttctccagct cctcctctgg ctcctcttcc ggtcctggca    4500
ccatcgccag gtgctgctcc tgtcctggct tcatcacaga ctccggttcc agttatggct    4560
ccatcgtcta ctccaggaac ctctttagcc tcagcttcac cggtaccagc tccaacccct    4620
gtgttggctc catcatcaac tcaaactatg ctaccagccc cggttccgtc acctctcccg    4680
agcccggctt ctacgcagac actggcccta gccccagctt tagcacccac tcttggaggc    4740
tcatctccat ctcagacact ctctttggga acggggaacc cccagggacc ctttccaact    4800
cagacattgt cattaactcc agcatcatcc ctggtaccaa ctccagccca gacactgtct    4860
ttggcaccag gaccaccact gggtccaact cagacgctgt ctctggctcc agcacccct    4920
ctggctccag cttctccagt gggcccagcc ccagctcaca cgctgacttt ggctccagca    4980
tcgtcatctg cttcactcct ggccccagct tcagtgcaga cactgacctt gagccctgcc    5040
ccagttccta ccctgggccc ggccgcagct cagaccttgg cgctggcccc agcctccaca    5100
cagtccccag cttcccaggc atcttcccct tgtggtttcg gcatctggtgc cgctcccttg    5160
cctgtcacca tggtatcccg gctgcctgtt tccaaggatg agcctgacac actgacattg    5220
cgctctggtc cccccagccc tccctccact gctacctcgt ttggtggccc ccggcctcga    5280
cgccagcccc ccccaccacc tcgttcccct ttttatctgg actccctgga ggaaaagcgg    5340
aagcggcagc ggtctgaacg cctggaacgg attttccaac ttagtgaggc tcatggggcc    5400
ctggcacctg tgtatgggac tgaagtcctg gatttctgta ccctgcccca acctgttgcc    5460
agccccatcg gccctcgttc tcctggcccc agccaccccca ccttttggac ttataccgag    5520
gctgcccacc gggctgtact gtttccccag cagcgactag accagctgtc agaaatcatt    5580
gagaggttca tctttgtcat gcctcctgtg gaggcacctc ccccttccct gcatgcctgc    5640
cacccacctc cttggctggc cccacgtcag gcagccttcc aggagcaatt ggcctctgag    5700
ctctggcccc gggctcgtcc tttgcaccgt attgtgtgta acatgcgcac ccagttccct    5760
gacttaagac tcatccagta tgattgcgga aagttgcaga cgttggcagt gctgttgcgg    5820
cagctcaagg cagagggcca ccgagtgctc atcttcaccc agatgacccg aatgctggat    5880
```

```
gtattggagc agtttctcac ctaccatggc catctctacc tgcgcctgga tggatctact   5940
agagttgaac agagacaggc cttgatggaa cggttcaatg cagacaaacg catattctgc   6000
ttcatccttt caactcggag tgggggtgtg ggcgtgaacc tgacaggagc agacactgtt   6060
gttttttatg acagcgactg gaatcccacc atggatgctc aggcccagga ccgctgtcac   6120
cgaattggcc agacccggga tgtccacata tataggctta tcagtgaacg gacagtggag   6180
gagaacatcc taaaaaaggc aaatcagaag agaatgttgg gggacatggc cattgaggga   6240
ggcaacttca ccacagccta tttcaaacag cagaccatcc gagagctgtt tgatatgccc   6300
ctggaggaac cttctagctc atccgtgccc tctgcccctg aagaggagga agagactgtg   6360
gccagcaagc agactcatat tctggagcag gcattgtgtc gggcagaaga tgaagaggat   6420
atccgtgcag ccacccaggc caaggctgaa caggtggctg agcttgcaga atttaatgag   6480
aacgatgggt ttcctgctgg tgagggagag gaagctggcc ggcctgggc tgaggatgag   6540
gagatgtccc gggctgagca ggaaattgct gccctcgtag aacagctgac ccccattgag   6600
cgctatgcca tgaaattcct ggaggcctca ctggaggagg tgagccgaga ggagctcaaa   6660
caggcagaag agcaagtgga agctgcccgc aaagacctgg accaagccaa ggaggaggtg   6720
ttccgcctac cccaagagga ggaggagggg ccggggggctg gggatgagag ttcctgtggg   6780
actggtggag gcacccaccg gcgcagtaaa aaggccaaag cccctgagag gccggggact   6840
cgtgtcagtg agcgtcttcg tggagcccgg gctgagactc aagggggcaaa ccacactcct   6900
gtcatatccg cccatcaaac tcgcagcacc accacaccac cccgctgcag tcctgccagg   6960
gagcgagttc ccaggccagc acctaggcct cgacccactc cagcttcagc tccggctgca   7020
attcctgccc ttgttcctgt cccagtttct gccccagtac ccatttcagc cccaaatcca   7080
ataaccattc tccctgtcca tatcttgcct tctcctcccc ctccttcaca gattcctcct   7140
tgttcttctc ctgcctgcac ccctcctcct gcctgtaccc ctccaccagc tcatacaccg   7200
cctccagccc aaacctgtct tgtaactcct tcctctcctc tcttgcttgg tccaccttct   7260
gtgcccatct ctgcctcagt cactaatctc cccttgggct tgaggcctga ggcagagctg   7320
tgtgcccagg cattggcatc tccagagtcc ctggagctgg cttctgtggc cagttcagaa   7380
acctcctcac tttctcttgt gccccctaaa gatctgttgc cagttgctgt ggagatcctg   7440
cctgtgtcag agaagaacct ttctctcacc ccttctgcac ccagcctgac cttggaggct   7500
ggcagcatcc ccaatggtca agagcaggag gcaccagatt ctgctgaggg gaccacccct   7560
acagtgctgc ctgaaggtga ggagttgccc ctgtgtgtga gtgagagcaa tggcctggag   7620
ctcccaccct cagcagcatc tgatgagcca cttcaggagc cactggaggc tgacaggacc   7680
tcggaagagc tgacagaggc caagacccca acctccagcc cagagaagcc acaggaactc   7740
gttacagctg aggttgcagc tccatccacc tcatcttcag ccacttcctc gcctgagggt   7800
ccttcacctg cccgacctcc tcggcgtcgc accagtgctg atgtggaaat taggggtcaa   7860
gggactggtc ggccaggaca accaccaggc cccaaagtgc ttcgaaagct gccaggacgg   7920
ctggtaactg tggtagagga aaaggaactg gtgcagcggc ggcggcagca gcggggagct   7980
gccagcaccc tagtgcctgg ggtctctgag actagtgcca gccgggaag cccgtctgtc   8040
cgcagcatgt cagggccaga atcctcccct cccattggtg ggccctgtga agctgctcct   8100
tcatcctcac tgcccactcc accccagcag cccttcattg ctcgccgtca cattgagctg   8160
ggggtgactg gtggtggcag ccccgagaat ggagacggag cactgctcgc catcacccca   8220
```

-continued

| | |
|---|---|
| cctgctgtga aacgtcggag ggggaggccc cccaagaaga acaggtctcc agcagatgct | 8280 |
| gggagaggtg tggatgaggc accctcatcc accttgaagg gaaaaaccaa tggggctgac | 8340 |
| ccagtccctg ggcctgagac cctaattgtt gcagatcctg tcctggaacc acagcttatt | 8400 |
| cctgggcccc agcctcttgg accccagcca gttcacagac ccaatcccct cctgtcacct | 8460 |
| gtggagaaaa aaggcgagg acgacccct aaagcacgag atttgcccat ccctgggacc | 8520 |
| atttcctctg caggggatgg caactccgaa agtcggacac agccaccccc acacccatca | 8580 |
| cccctaaccc cactcccacc actgctagtt tgtcccactg ctactgttgc caacactgtc | 8640 |
| accactgtca ccatttcaac gtccccaccc aaacggaaga ggggccgacc tcccaagaat | 8700 |
| cctccatcac ctcggcccag ccagctcccc gtcttggacc gtgacagcac ttctgttctc | 8760 |
| gagagctgtg gattggggag gcgacggcaa ccccagggcc aaggggagag tgagggtagt | 8820 |
| tcctctgatg aggatggaag ccgcccctc acccgcctgg cccgccttcg gcttgaagca | 8880 |
| gaaggaatgc gaggacggaa gagtggaggg tccatggtgg tggctgtaat tcaggatgac | 8940 |
| ctggacttag cagatagcgg gccagccggg ttggaattga caccacctgt ggtctcacta | 9000 |
| acccccaaaac tgcgctcgac ccggctgcgt ccagggtctc tagtccccc actagagact | 9060 |
| gagaagttgc ctcgcaaacg agcagggccc ccagttggtg ggagtcctgg gctggcaaag | 9120 |
| cggggccgcc tacagccccc aagtcccctg gggcctgagg gttcagtaga ggagtctgag | 9180 |
| gctgaagcct caggtgagga ggaggaaggg gatgggaccc cacgccgacg tcctggcccc | 9240 |
| cgccggcttg ttgggaccac caaccaaggg gaccagcgca tcctgcgcag cagcgcccct | 9300 |
| ccctccctgg ctggccctgc tgttagtcac agaggccgca aggccaagac gtga | 9354 |

<210> SEQ ID NO 11
<211> LENGTH: 8916
<212> TYPE: DNA
<213> ORGANISM: Human

<400> SEQUENCE: 11

| | |
|---|---|
| atggccaagg atgtcaggca gttctggagc aatgtggaga aggtggtgca attcaagcaa | 60 |
| cagtcccggc ttgaggaaaa gcgcaaaaaa gccctggacc tgcatttgga cttcattgtg | 120 |
| gggcaaactg aaaagtactc ggaccttctg tctcagagcc tcaaccagcc attaacctcc | 180 |
| agcaaagcag gctcttcccc ttgcctcggc tcttcctcag ctgcctccag tcctccaccc | 240 |
| cctgcttctc gcctggatga tgaagatggg gactttcaac cccaagagga tgaggaagag | 300 |
| gatgatgagg aaacgattga agttgaagaa caacaggaag gcaatgatgc agaggcccag | 360 |
| aggcgtgaga ttgagctgct tcgccgtgag ggagaattgc cactggaaga gctgctccgt | 420 |
| tccccttccc ctcagctgtt ggaagggcct tccagcccct ctcaaacccc ctcatctcat | 480 |
| gatagtgaca cccgagatgg gcctgaagaa ggtgctgaag aagagccccc tcaggtgttg | 540 |
| gagataaagc ccccacccte tgctgtcaca cagcgcaaca acagccttg gcatccagat | 600 |
| gaagatgatg aagagtttac tgccaacgaa gaggaagcgg aggatgaaga ggatactata | 660 |
| gcagctgagg aacagttgga aggggaggtg gatcatgcca tggagctgag cgagttggct | 720 |
| cgagaaggtg agctttccat ggaggagcta ttgcagcagt atgcaggagc ctatgcccca | 780 |
| ggctctggga gcagtgaaga tgaggatgaa gatgaggttg atgctaatag ctctgactgt | 840 |
| gaaccagagg ggcccgtgga agcggaagag cctcctcagg aggatagtag cagtcagtca | 900 |
| gactctgtgg aggaccggag tgaggatgag gaagatgaac attcagagga ggaagaaaca | 960 |
| agtggaagtt cagcatcaga ggaatctgag tctgaagagt ctgaggatgc ccaatcacag | 1020 |

```
agccaagcag atgaagagga ggaagatgat gattttgggg tggagtactt gcttgccagg    1080
gatgaagagc agagtgaggc agatgcaggc agtgggcctc ctactccagg gcccactact    1140
ctaggtccaa agaaagaaat tactgacatt gctgcagcag ctgaaagtct ccagcccaag    1200
ggttacacgc tggccacgac ccaggtaaag acgcccattc ccctgcttct gcggggccag    1260
ctccgggagt accagcacat tgggctagac tggctggtta ccatgtatga aagaagctt    1320 aatggcattc ttgctgatga gatggggctt gggaagacca tccagaccat ctctctgctt    1380
gcccacttgg cttgtgagaa aggtaactgg ggtccccatt taatcattgt tcccaccagc    1440
gtgatgttga actgggagat ggagttgaaa cgttggtgcc ccagctttaa aatcctcact    1500
tactatggag cccagaaaga gaggaagctc aagcggcagg gctggaccaa gcccaatgcc    1560
tttcatgtgt gtatcacatc ttacaagctg gtgctgcagg accaccaggc cttccgtcgc    1620
aagaactggc gctatctcat tctggatgag gcgcagaaca tcaagaactt caagtcacag    1680
cgctggcagt cactcctcaa cttcaacagc cagagacgcc tgctcctgac aggaactccc    1740
ttgcagaaca gcctcatgga gctgtggtcc ttgatgcact ttttgatgcc ccatgtcttc    1800
cagtctcatc gcgagttcaa ggagtggttc tctaatcccc taactggcat gattgagggc    1860
agccaagagt ataatgaagg tctagtcaaa cgcctccaca aggttttgag gcctttttta    1920
ctgcgccgag ttaaggtgga tgttgagaag cagatgccca aaaagtacga gcatgttatc    1980
cgctgcaggc tctccaagcg tcaacgctgt ctctatgatg acttcatggc acagaccaca    2040
actaaggaga cactagccac aggccatttc atgagcgtca tcaacatttt gatgcagctg    2100
agaaaagttt gcaatcatcc aaatctgttc gaccctcgac cggttacctc ccctttcatc    2160 acccccaggca tctgcttcag caccgcctct ctggtgctaa gggccacgga tgtccatccc    2220
ctccagcgga tagacatggg tcgatttgac cttattggcc tggaaggtcg tgtctctcga    2280
tatgaggcag acacatttct gccccggcac cgcctctctc gccgggtact gttagaagtg    2340
gctactgctc ctgaccccccc accccggccc aagccagtca agatgaaggt caacaggatg    2400
ctgcagccag tacctaagca agaaggccgg acagtggtgg tggtgaacaa cccacgggcg    2460
cccctgggcc ctgtcccagt tcgacctcct ccaggtcctg agctctcagc ccagcccacc    2520
cctggcccag tcccccaagt gctgccagca tcactgatgg tttcagcctc acctgccggg    2580
ccccgcgtta ttcctgcatc tcggcctcct ggcctgtcc tcttgcctcc actgcagccc    2640
aacagtggtt ctctccccca ggtgttgcca tccccctgg gggtcctgag tgggacctca    2700
cggcctccca cgccaacctt gtccctaaag ccaacaccac ctgccccagt tcgcctgagc    2760 ccagcccac ctccaggctc ctctagcctg ttgaagcccc tgacagtgcc accaggctac    2820
accttccctc ctgctgctgc caccaccact tctaccacca cggcaactgc taccaccaca    2880
gcagtgccag ctccgactcc tgcaccacag cgcctcattc tatctcccga tatgcaggct    2940
cgcctgccct caggcgaagt ggtcagcatc gggcagttag cctcactggc acaacgtcca    3000
gtggctaatg caggggggaag caaacctctc accttccaaa tccagggcaa caagctgact    3060
ttgactggtg cccaggtgcg ccagcttgct gtggggcagc ccgcccgct gcaaatgcca    3120 ccaaccatgg tgaataatac aggcgtggtg aagattgtag tgagacaagc ccctcgggat    3180
ggactgactc ctgttcctcc attggcccca gcaccccggc ctccgagctc tgggcttcca    3240
gctgtgttga atccacgccc cacgttaacc cctggccggc tacccacacc tactctgggt    3300
actgctcgag cccccatgcc cacacccact ctggtgaggc ctcttctcaa gctggtccac    3360
```

-continued

```
agtccttcac ctgaagtcag tgcttcagcc cccggagctg cccccttgac catctcttct    3420
cctctccacg tgccatcctc actccctggg ccagcctctt ctccaatgcc aattcccaac    3480
tcctctcccc ttgctagtcc tgtgtcctct acagtctcag ttccattgtc atcttcactc    3540
cccatctctg tccccaccac acttcctgcc ccagcctcgg ctccactcac catccccatc    3600
tcagcccect tgactgtttc tgcttcgggc ccagctctgt tgaccagtgt gactccacca    3660
ttggcacctg ttgtcccagc ggctcctgga cctccctcct tgcagccatc tggtgcttcc    3720
ccgtcagcat cagccttgac tctaggtttg gccacagctc catccctgtc ttcatctcag    3780
acacctggtc accctctgtt gttggctccc acctcttcac atgttccagg gttgaactca    3840
accgtggccc cagcatgctc acctgtcctg gtgccagctt cggctctggc cagtccttt     3900
ccgtcagcac caaatccagc tccagctcag gcttcccttc tggctccagc atcttctgca    3960
tctcaggctc tagccacccc tctggctcct atggcggctc cacagacagc aattctggct    4020
ccttctccag ctcctcctct ggctcctctt ccggtcctgg caccatcgcc aggtgctgct    4080
cctgtcctgg cttcatcaca gactccggtt ccagttatgg ctccatcgtc tactccagga    4140
acctctttag cctcagcttc accggtacca gctccaaccc ctgtgttggc tccatcatca    4200
actcaaacta tgctaccagc cccggttccg tcacctctcc cgagcccggc ttctacgcag    4260
acactggccc tagcccagc tttagcaccc actcttggag gctcatctcc atctcagaca     4320
ctctctttgg gaacggggaa ccccagggga ccctttccaa ctcagacatt gtcattaact    4380
ccagcatcat ccctggtacc aactccagcc cagacactgt ctttggcacc aggaccacca    4440
ctgggtccaa ctcagacgct gtctctggct ccagcacccc ctctggctcc agcttctcca    4500
gtgggcccag ccccagctca cacgctgact ttggctccag catcgtcatc tgcttcactc    4560
ctggccccag cttcagtgca gacactgacc ttgagccctg ccccagttcc taccctgggc    4620
ccggccgcag ctcagacctt ggcgctggcc ccagcctcca cagtcccc agcttcccag      4680
gcatcttccc ttgtggtttc ggcatctggt gccgctccct tgcctgtcac catggtatcc    4740
cggctgcctg ttttccaagga tgagcctgac acactgacat tgcgctctgg tcccccagc    4800
cctccctcca ctgctacctc gtttggtggc cccggcctc gacgccagcc cccccacca     4860
cctcgttccc cttttatct ggactccctg gaggaaaagc ggaagcggca gcggtctgaa    4920
cgcctggaac ggattttcca acttagtgag gctcatgggg ccctggcacc tgtgtatggg    4980
actgaagtcc tggatttctg taccctgccc caacctgttg ccagcccat cggccctcgt     5040
tctcctggcc ccagccaccc cacctttttgg acttataccg aggctgccca ccgggctgta    5100
ctgtttcccc agcagcgact agaccagctg tcagaaatca ttgagaggtt catctttgtc    5160
atgcctcctg tggaggcacc tccccttcc ctgcatgcct gccacccacc tccttggctg     5220
gccccacgtc aggcagcctt ccaggagcaa ttggcctctg agctctggcc ccgggctcgt    5280
cctttgcacc gtattgtgtg taacatgcgc acccagttcc ctgacttaag actcatccag    5340
tatgattgcg gaaagttgca gacgttgca gtgctgttgc ggcagctcaa ggcagagggc     5400
caccgagtgc tcatcttcac ccagatgacc cgaatgctgg atgtattgga gcagtttctc    5460
acctaccatg gccatctcta cctgcgcctg gatggatcta ctagagttga acagagacag    5520
gccttgatgg aacggttcaa tgcagacaaa cgcatattct gcttcatcct ttcaactcgg    5580
agtggggtg tgggcgtgaa cctgacagga gcagacactg ttgttttta tgacagcgac    5640
tggaatccca ccatggatgc tcaggcccag gaccgctgtc accgaattgg ccagacccgg    5700
gatgtccaca tatataggct tatcagtgaa cggacagtgg aggagaacat cctaaaaaag    5760
```

-continued

```
gcaaatcaga agagaatgtt gggggacatg gccattgagg gaggcaactt caccacagcc    5820
tatttcaaac agcagaccat ccgagagctg tttgatatgc ccctggagga accttctagc    5880
tcatccgtgc cctctgcccc tgaagaggag gaagagactg tggccagcaa gcagactcat    5940
attctggagc aggcattgtg tcgggcagaa gatgaagagg atatccgtgc agccacccag    6000
gccaaggctg aacaggtggc tgagcttgca gaatttaatg agaacgatgg gtttcctgct    6060
ggtgagggag aggaagctgg ccggcctggg gctgaggatg aggagatgtc ccggctgag     6120 caggaaattg ctgccctcgt agaacagctg accccccattg agcgctatgc catgaaattc    6180
ctggaggcct cactggagga ggtgagccga gaggagctca acaggcaga agagcaagtg     6240 gaagctgccc gcaaagacct ggaccaagcc aaggaggagg tgttccgcct accccaagag    6300
gaggaggagg ggccgggggc tggggatgag agttcctgtg ggactggtgg aggcacccac    6360
cggcgcagta aaaaggccaa agcccctgag aggccgggga ctcgtgtcag tgagcgtctt    6420
cgtggagccc gggctgagac tcaaggggca aaccacactc ctgtcatatc cgcccatcaa    6480
actcgcagca ccaccacacc accccgctgc agtcctgcca gggagcgagt tcccaggcca    6540
gcacctaggc ctcgacccac tccagcttca gctccggctg caattcctgc ccttgttcct    6600
gtcccagttt ctgccccagt acccatttca gccccaaatc caataaccat tctccctgtc    6660
catatcttgc cttctcctcc ccctccttca cagattcctc cttgttcttc tcctgcctgc    6720 accccctcctc ctgcctgtac ccctccacca gctcatacac cgcctccagc ccaaacctgt    6780
cttgtaactc cttcctctcc tctcttgctt ggtccacctt ctgtgcccat ctctgcctca    6840
gtcactaatc tcccctttggg cttgaggcct gaggcagagc tgtgtgccca ggcattggca    6900
tctccagagt ccctggagct ggcttctgtg gccagttcag aaacctcctc actttctctt    6960
gtgcccccta aagatctgtt gccagttgct gtggagatcc tgcctgtgtc agagaagaac    7020 cttttctctca cccccttctgc acccagcctg accttggagg ctggcagcat ccccaatggt    7080
caagagcagg aggcaccaga ttctgctgag gggaccaccc ttacagtgct gcctgaaggt    7140
gaggagttgc ccctgtgtgt gagtgagagc aatggcctgg agctcccacc ctcagcagca    7200
tctgatgagc cacttcagga gccactggag gctgacagga cctcggaaga gctgacagag    7260
gccaagaccc caacctccag cccagagaag ccacaggaac tcgttacagc tgaggttgca    7320
gctccatcca cctcatcttc agccacttcc tcgcctgagg gtccttcacc tgcccgacct    7380
cctcggcgtc gcaccagtgc tgatgtggaa attaggggtc aagggactgg tcggccagga    7440
caaccaccag gccccaaagt gcttcgaaag ctgccaggac ggctggtaac tgtggtagag    7500
gaaaaggaac tggtgcagcg gcggcggcag cagcggggag ctgccagcac cctagtgcct    7560
ggggtctctg agactagtgc cagcccggga agcccgtctg tccgcagcat gtcagggcca    7620
gaatcctccc ctcccattgg tgggcccgtg aagctgctcc ttcatcctcc actgcccact    7680
ccaccccagc agcccttcat tgctcgccgt cacattgagc tgggggtgac tggtggtggc    7740
agccccgaga atggagacgg agcactgctc gccatcaccc cacctgctgt gaacgtcgg     7800 agggggaggc cccccaagaa gaacaggtct ccagcagatg ctgggagagg tgtggatgag    7860
gcaccctcat ccaccttgaa gggaaaaacc aatgggctg acccagtccc tgggcctgag    7920
accctaattg ttgcagatcc tgtcctggaa ccacagctta ttcctgggcc ccagcctctt    7980
ggaccccagc cagttcacag acccaatccc tcctgtcac ctgtggagaa agaaggcga     8040 ggacgacccc ctaaagcacg agatttgccc atccctggga ccatttcctc tgcagggat    8100
```

```
ggcaactccg aaagtcggac acagccaccc ccacacccat caccccctaac cccactccca    8160 ccactgctag tttgtcccac tgctactgtt gccaacactg tcaccactgt caccatttca    8220
acgtccccac ccaaacggaa gaggggccga cctcccaaga atcctccatc acctcggccc    8280
agccagctcc ccgtcttgga ccgtgacagc acttctgttc tcgagagctg tggattgggg    8340
aggcgacggc aacccagggg ccaaggggag agtgagggta gttcctctga tgaggatgga    8400
agccgccccc tcacccgcct ggcccgcctt cggcttgaag cagaaggaat gcgaggacgg    8460
aagagtggag ggtccatggt ggtggctgta attcaggatg acctggactt agcagatagc    8520
gggccaggcg ggttggaatt gacaccacct gtggtctcac taaccccaaa actgcgctcg    8580
acccggctgc gtccagggtc tctagtcccc ccactagaga ctgagaagtt gcctcgcaaa    8640
cgagcagggg ccccagttgg tgggagtcct gggctggcaa agcggggccg cctacagccc    8700
ccaagtcccc tggggcctga gggttcagta gaggagtctg aggctgaagc ctcaggtgag    8760
gaggaggaag gggatgggac cccacgccga cgtcctggcc cccgccggct tgttgggacc    8820
accaaccaag gggaccagcg catcctgcgc agcagcgccc ctccctccct ggctggccct    8880
gctgttagtc acagaggccg caaggccaag acgtga                              8916

<210> SEQ ID NO 12
<211> LENGTH: 20
<212> TYPE: DNA
<213> ORGANISM: Human

<400> SEQUENCE: 12
tgtccgtcag aacccatgcg                                                    20

<210> SEQ ID NO 13
<211> LENGTH: 18
<212> TYPE: DNA
<213> ORGANISM: Human

<400> SEQUENCE: 13
agggcttcct cttggaga                                                      18

<210> SEQ ID NO 14
<211> LENGTH: 20
<212> TYPE: DNA
<213> ORGANISM: Photinus pyralis

<400> SEQUENCE: 14
ttcgcagcct accgtagtgt                                                    20

<210> SEQ ID NO 15
<211> LENGTH: 19
<212> TYPE: DNA
<213> ORGANISM: Photinus pyralis

<400> SEQUENCE: 15
ccctggaaga tggaagcgt                                                     19

<210> SEQ ID NO 16
<211> LENGTH: 24
<212> TYPE: DNA
<213> ORGANISM: Human

<400> SEQUENCE: 16
agaacatcat ccctgcctct actg                                               24
```

-continued

```
<210> SEQ ID NO 17
<211> LENGTH: 24
<212> TYPE: DNA
<213> ORGANISM: Human

<400> SEQUENCE: 17
catgtgggcc atgaggtcca ccac                                              24
```